(12) United States Patent
Bennett et al.

(10) Patent No.: US 11,458,137 B2
(45) Date of Patent: *Oct. 4, 2022

(54) COMPOSITIONS AND METHODS OF USING TYROSINE KINASE INHIBITORS

(71) Applicant: YALE UNIVERSITY, New Haven, CT (US)

(72) Inventors: Anton Bennett, Wilton, CT (US); Jae-Sung Yi, Hamden, CT (US)

(73) Assignee: YALE UNIVERSITY, New Haven, CT (US)

( * ) Notice: Subject to any disclaimer, the term of this patent is extended or adjusted under 35 U.S.C. 154(b) by 296 days.

This patent is subject to a terminal disclaimer.

(21) Appl. No.: 16/575,637

(22) Filed: Sep. 19, 2019

(65) Prior Publication Data

US 2020/0009142 A1    Jan. 9, 2020

Related U.S. Application Data

(63) Continuation of application No. 15/544,401, filed as application No. PCT/US2016/014882 on Jan. 26, 2016, now Pat. No. 10,471,059.

(60) Provisional application No. 62/107,553, filed on Jan. 26, 2015, provisional application No. 62/250,052, filed on Nov. 3, 2015.

(51) Int. Cl.
*A61K 31/506*   (2006.01)
*A61P 9/00*    (2006.01)
*A61K 45/06*   (2006.01)

(52) U.S. Cl.
CPC ............. *A61K 31/506* (2013.01); *A61P 9/00* (2018.01)

(58) Field of Classification Search
CPC .......... A61K 31/506; A61K 45/06; A61P 9/00
USPC .................................................. 514/252.19
See application file for complete search history.

(56) References Cited

U.S. PATENT DOCUMENTS

| | | |
|---|---|---|
| 2006/0014932 A1 | 1/2006 | Zhao |
| 2007/0015777 A1 | 1/2007 | Bush et al. |
| 2007/0123539 A1 | 5/2007 | Wu et al. |
| 2009/0123550 A1 | 5/2009 | Phillips et al. |
| 2013/0150294 A1 | 6/2013 | Xie et al. |

FOREIGN PATENT DOCUMENTS

| | | |
|---|---|---|
| WO | 0134201 A2 | 5/2001 |
| WO | 2005037843 A1 | 4/2005 |
| WO | 2006029319 A2 | 3/2006 |
| WO | 2007135397 A1 | 11/2007 |
| WO | 2008054792 A2 | 5/2008 |
| WO | 2011095588 A1 | 8/2011 |
| WO | 2014110198 A2 | 7/2014 |
| WO | 2014110198 A3 | 7/2014 |
| WO | 2015006492 A1 | 1/2015 |

OTHER PUBLICATIONS

Luo et al Clinical Cancer Research, 2006, 12(23), 7180-7186 (Year: 2006).*
Extended European Search Report for European Patent Application No. 16743949.6 dated Aug. 24, 2018.
International Search Report and Written Opinion for PCT International Application No. PCT/US2016/014882 dated Apr. 21, 2016.
Pfizer Labs (Bosulif (bosutinib) tablet label), 2013.
Apperley, et al., "Dasatinib in the treatment of chronic myeloid leukemia in accelerated phase after imatinib failure the START a trial", J Clin Oncol. 27(21), 2009, 3472-3479.
Araki, et al., "Mouse model of Noonan syndrome reveals cell type- and gene dosage-dependent effects of Ptpn11 mutation", Nat Med. 10(8), 2004, 849-857 (abstract only).
Eminaga, et al., "Noonan syndrome-associated SHP-2/Ptpn11 mutants enhance SIRPalpha and PZR tyrosyl phosphorylation and promote adhesion-mediated ERK activation", J Biol Chem. 283(22), May 2008, 15328-15338.
Gelb, et al., "Noonan syndrome and related disorders: dysregulated RAS-mitogen activated protein kinase signal transduction", Hum Mol Genet. 15 Spec No. 2:, Oct. 2006, R220-226.
Hasinoff, et al., "The lack of target specificity of small molecule anticancer kinase inhibitors is correlated with their ability to damage myocytes in vitro", Toxicol Appl Pharmacol. 249(2), Dec. 2010, 132-139.
Jopling, et al., "Shp2 knockdown and Noonan/LEOPARD mutant Shp2-induced gastrulation defects", PLoS Genet. 3(12), 2007, e225.
Kantarjian, et al., "Dasatinib versus imatinib in newly diagnosed chronic-phase chronic myeloid leukemia", N Engl J Med. 362(24), 2010, 2260-2270.
Kontaridis, et al., "PTPN11 (Shp2) mutations in LEOPARD syndrome have dominant negative, not activating, effects", J Biol Chem. 281(10), 2006, 6785-6792.
Lee, "Src tyrosine kinase inhibitor PP2 markedly enhances Ras-independent activation of Raf-1 protein kinase by phorbol myristate acetate and H2O2", J Biol Chem. 279(47), Nov. 2004, 48692-48701.
Marin, et al., "Rapamycin reverses hypertrophic cardiomyopathy in a mouse model of LEOPARD syndrome-associated PTPN11 mutation", J Clin Invest. 121(3), Mar. 2011, 1026-1043.
Rikova, et al., "Global survey of phosphotyrosine signaling identifies oncogenic kinases in lung cancer", Cell. 131(6), 2007, 1190-1203.

(Continued)

*Primary Examiner* — Yevgeny Valenrod
(74) *Attorney, Agent, or Firm* — Saul Ewing Arnstein & Lehr LLP; Kathryn Doyle; Justin Crotty

(57) ABSTRACT

The present invention provides compositions and methods of inhibiting tyrosine phosphorylation. In one aspect, a composition comprising a low-dosage tyrosine kinase inhibitor, where the low-dosage tyrosine kinase inhibitor decreases tyrosine phosphorylation, is provided. In another aspect, a method for treating cardiovascular disease or condition associated with a RASopathy having aberrant protein tyrosine phosphorylation is described. Methods for treating congenital heart disease associated with Noonan or Noonan syndrome with multiple lentigines and decreasing aberrant levels of Protein Zero-Related (PZR) tyrosyl phosphorylation are also described.

8 Claims, 50 Drawing Sheets

Specification includes a Sequence Listing.

(56) References Cited

OTHER PUBLICATIONS

Schramm, et al., "New approaches to prevent LEOPARD syndrome-associated cardiac hypertrophy by specifically targeting Shp2-dependent signaling", J Biol Chem. 288(25), Jun. 2013, 18335-18344.

Shah, et al., "Overriding imatinib resistance with a novel ABL kinase inhibitor", Science. 305(5682), 2004, 399-401.

Uhlén, et al., "Gain-of-function/Noonan syndrome SHP-2/Ptpn11 mutants enhance calcium oscillations and impair NFAT signaling", Proc Natl Acad Sci U S A. 103(7), 2006, 2160-2165.

Xu, et al., "Primary culture of adult rat heart myocytes", J Vis Exp. (28), 2009, 1-3.

Yu, et al., "Phase II study of dasatinib in patients with metastatic castration-resistant prostate cancer", Clin Cancer Res. 15(23), 2009, 7421-7428.

Zhang, et al., "Shp2 regulates SRC family kinase activity and Ras/Erk activation by controlling Csk recruitment", Mol Cell. 13(3), 2004, 341-355.

Eng, et al., "Activity of rapamycin (AY-22,989) against transplanted tumors", J Antibiotics (Tokyo). 37(10), 1984, 1231-1237.

Lee, et al., "Rapamycin weekly maintenance dosing and the potential efficacy of combination sorafenib plus rapamycin but not atorvastatin or doxycycline in tuberous sclerosis preclinical models.", BMC Pharmacol. 9, Apr. 2009, 1-15.

Montero, et al., "Inhibition of Src Family Kinases and Receptor Tyrosine Kinases by Dasatinib: Possible Combinations in Solid Tumors", Clin Cancer Res. 17(17), Sep. 2011, 5546-5552.

Marin, Talita M. et al., "Rapamycin reverses hypertrophic cardiomyopathy in a mouse model of LEOPARD syndrome-associated PTPN11 mutation", J. Clin. Invest., Mar. 2011, vol. 121(3), pp. 1026-1043.

\* cited by examiner

| | | | | |
|---|---|---|---|---|
| H. sapiens | 224 | EGLVKSLPS-GSHQGPVIY | 241 AQLDHSGGHHSDKINKSESVVY | 263 ADIRKN 269 |
| M. musculus | 224 | EGLVKSPPSAGSHQGPVIY | 242 AQLDHSGGHHSGKINKSESVVY | 264 ADIRKD 270 |
| R. norvegicus | 224 | EGLVKSPPSAGSHQGPVIY | 242 AQLDHSGGHHSGKINKSESVVY | 264 ADIRKD 270 |
| B. taurus | 224 | EGLVKSLPS-GSHQGPVIY | 241 AQLDHSGGHHSDRINKSESVVY | 263 ADIRKN 269 |
| C. familiaris | 224 | EGLVKSLPS-GSHQGPVIY | 241 AQLDHSGGHHSDKINKSESVVY | 263 ADIRKN 269 |
| D. rerio | 219 | DNSRCSSPS-APVQGPVIY | 236 AQLDHSGSKNSSFHKMEPVVY | 258 ADIRKN 264 |
| G. gallus | 227 | EGLVNSVPA-RSHQGPVIY | 244 AQLDHSGGQHSDKINKSESVVY | 266 ADIRKN 272 |

ITIM (under AQLDHSGG... region) and ITIM (under ...SESVVY region)

Figure 1E

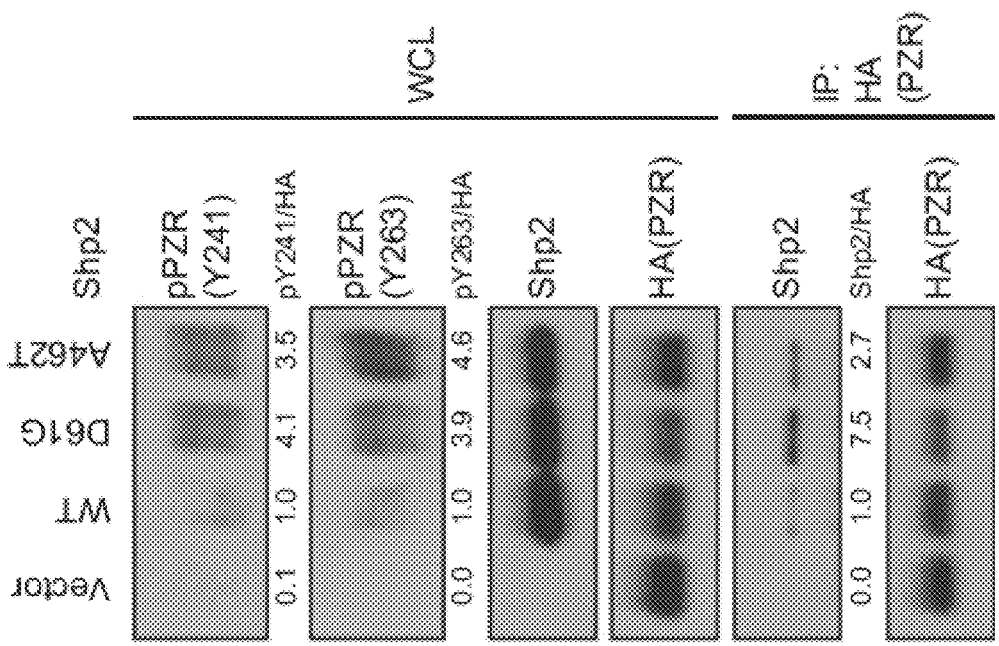
Figure 2E
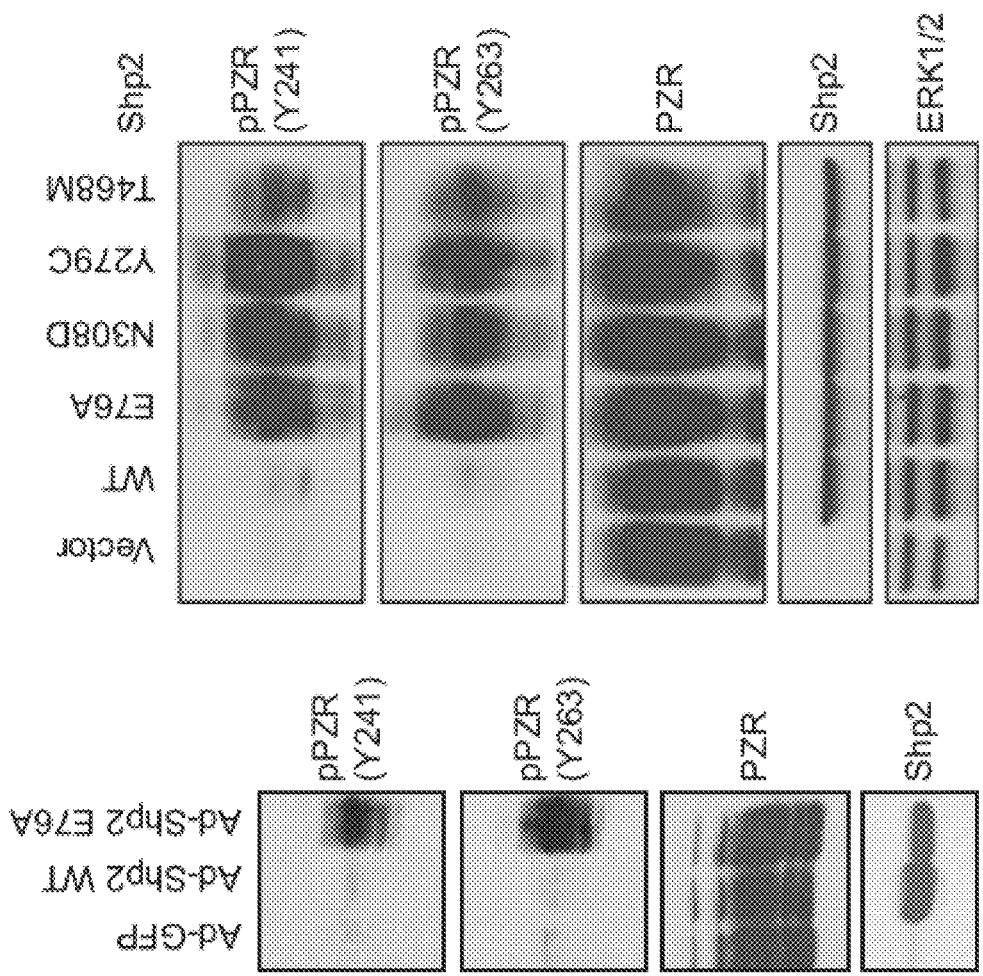
Figure 2D
Figure 2C

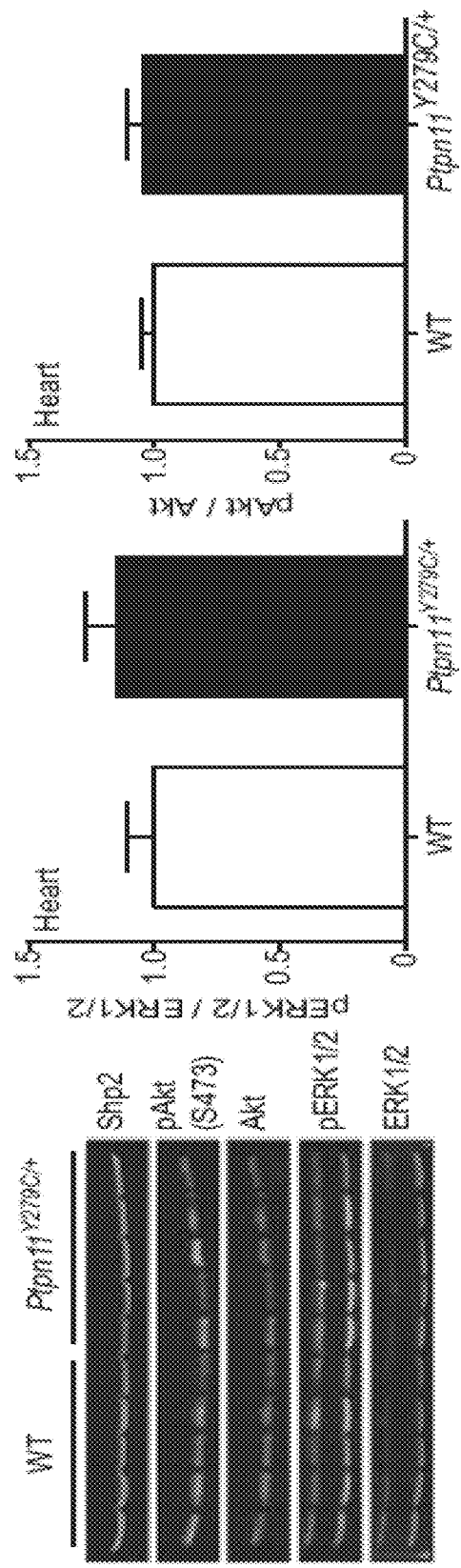
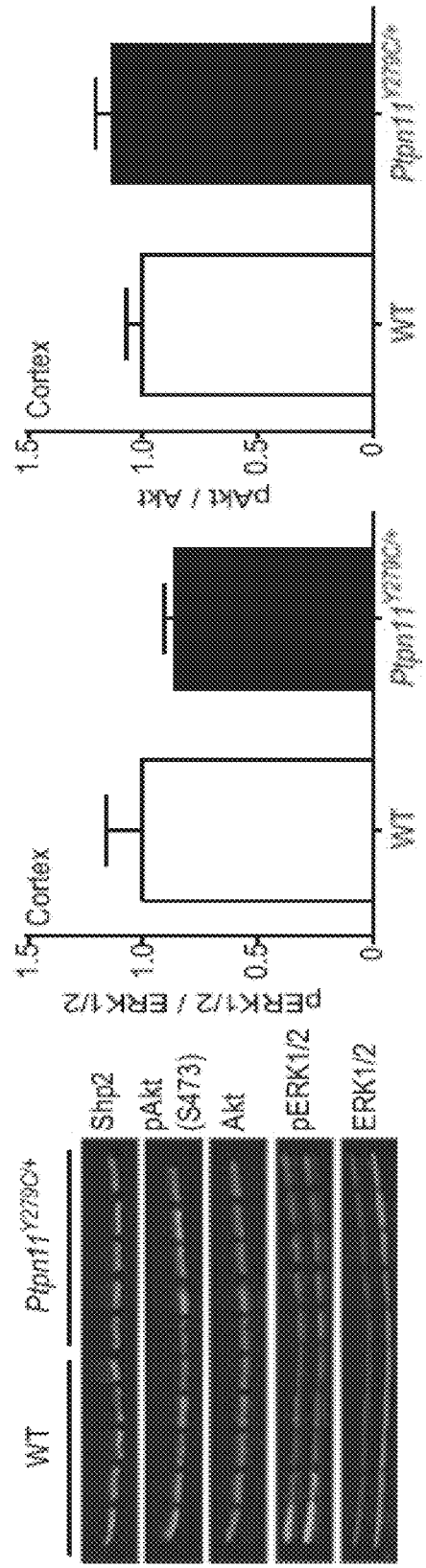
Figure 5C
Figure 5D

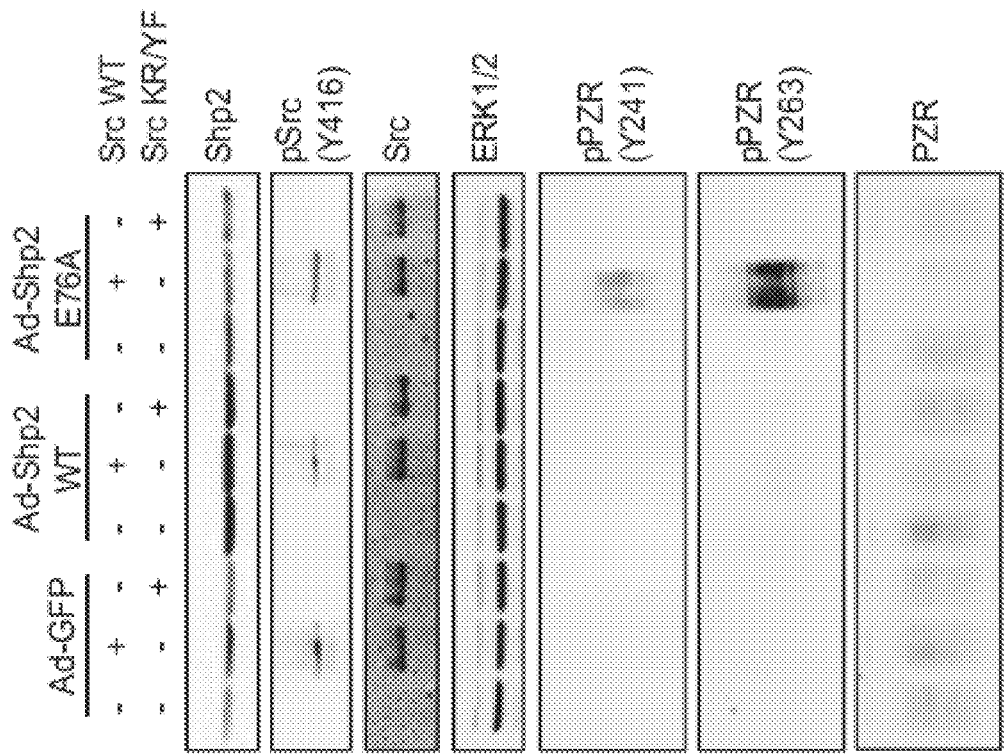
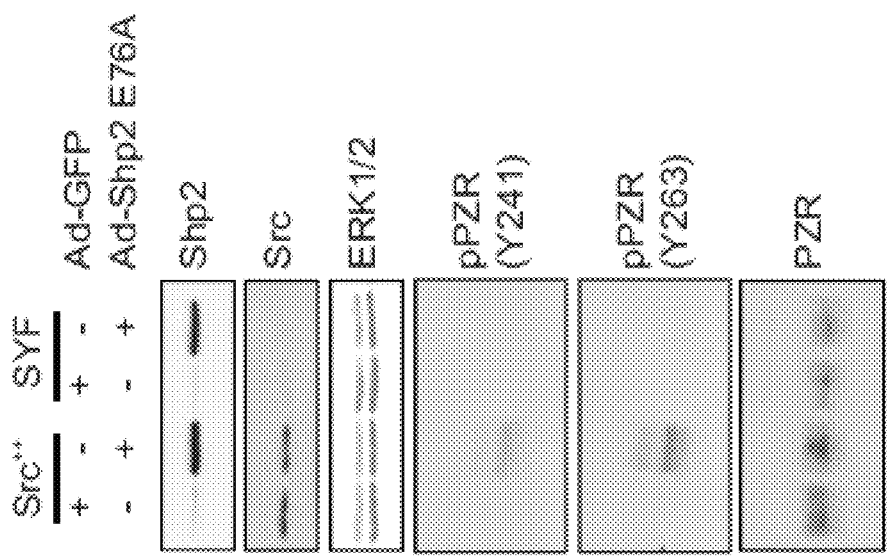
Figure 7B
Figure 7A

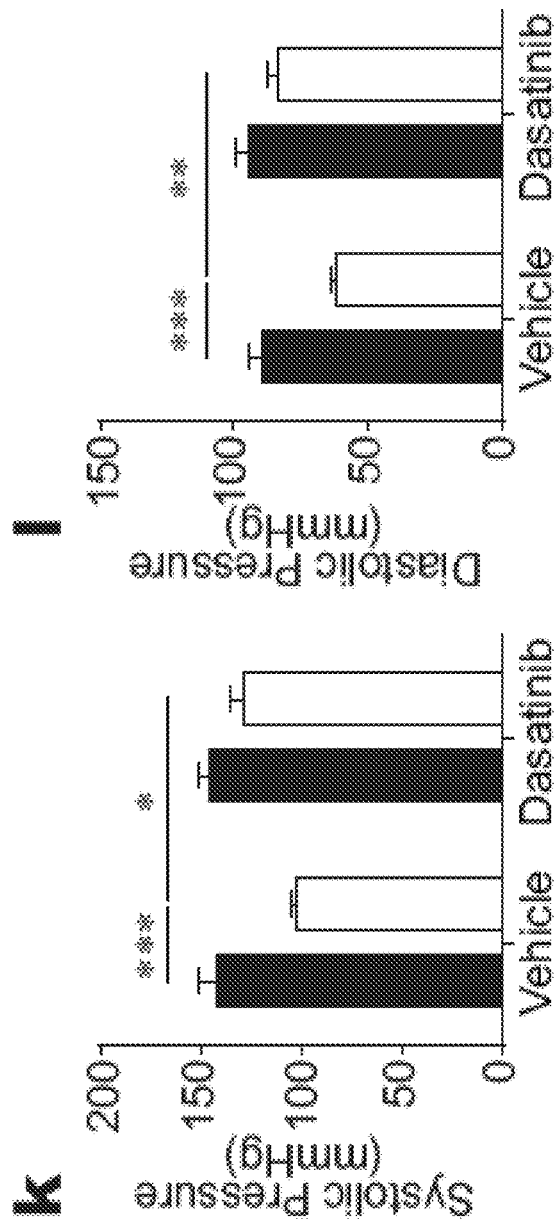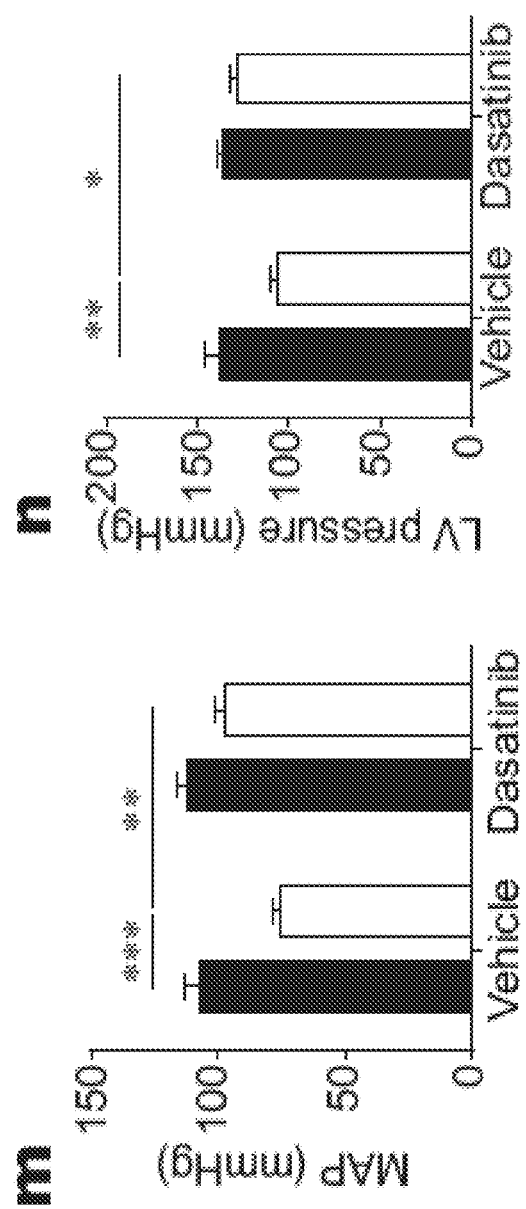
Figures 14k-14n

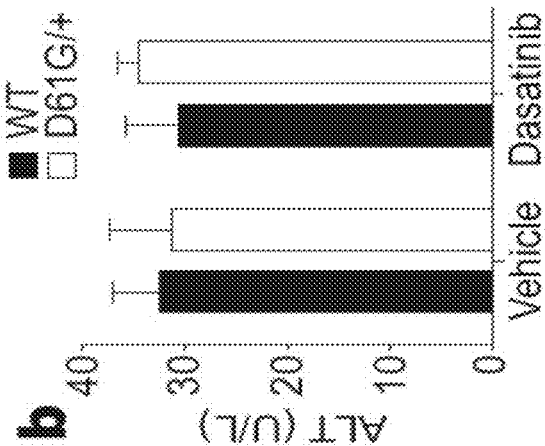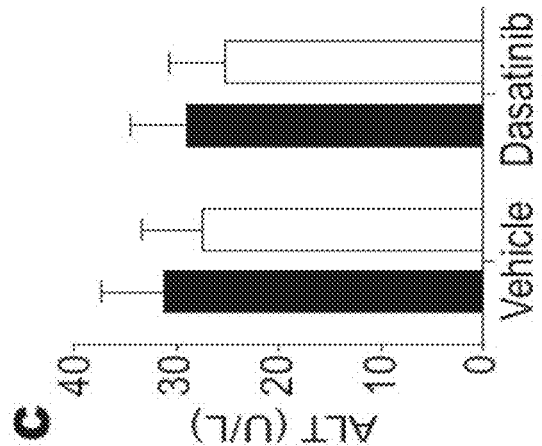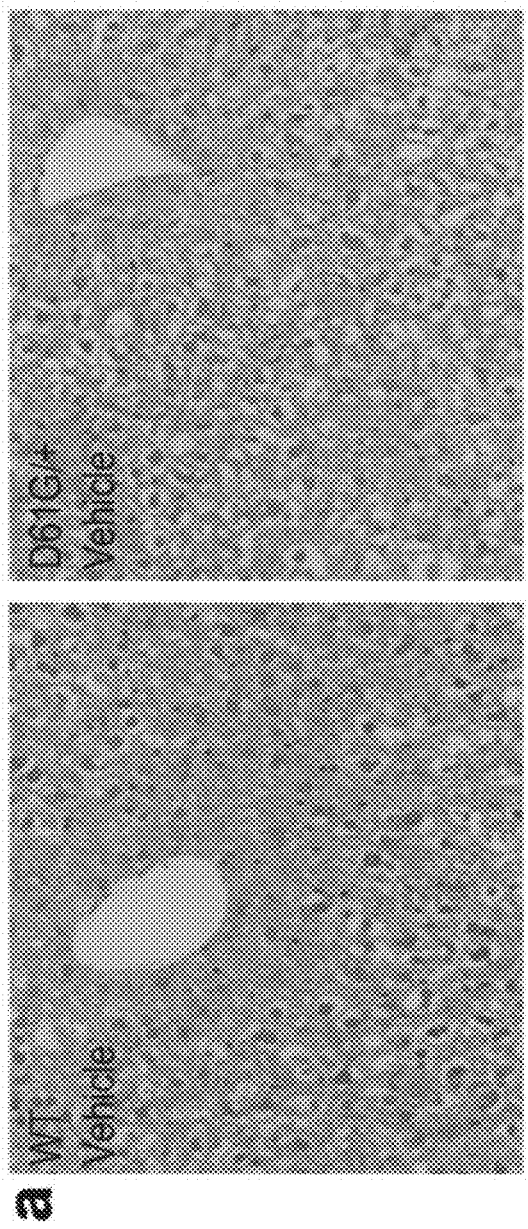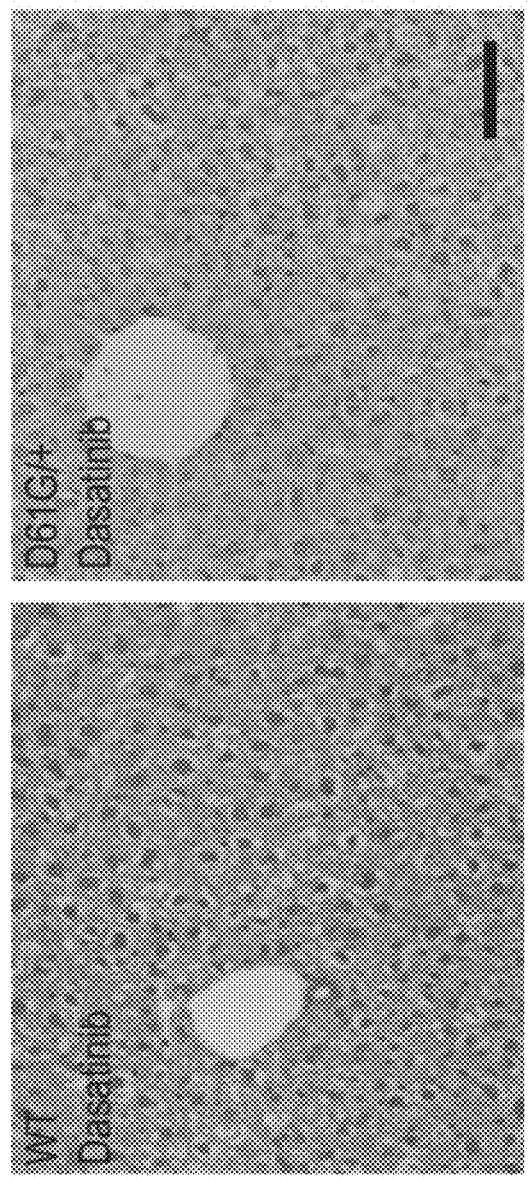
Figures 22a-22c

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1
accgcagcta ggaataatgg a                                        21

<210> SEQ ID NO 2
<211> LENGTH: 19
<212> TYPE: DNA
<213> ORGANISM: Artificial Sequence
<220> FEATURE:
<223> OTHER INFORMATION: Synthetic sequence

<400> SEQUENCE: 2
accaaaagcc ttgactccg                                           19

<210> SEQ ID NO 3
<211> LENGTH: 25
<212> TYPE: DNA
<213> ORGANISM: Artificial Sequence
<220> FEATURE:
<223> OTHER INFORMATION: Synthetic sequence

<400> SEQUENCE: 3
cctggaggag aagatgccgg tagaa                                    25

<210> SEQ ID NO 4
<211> LENGTH: 24
<212> TYPE: DNA
<213> ORGANISM: Artificial Sequence
```

-continued

```
<220> FEATURE:
<223> OTHER INFORMATION: Synthetic sequence

<400> SEQUENCE: 4
ccccagtcca gggaggcacc tcgg                                                 24

<210> SEQ ID NO 5
<211> LENGTH: 26
<212> TYPE: DNA
<213> ORGANISM: Artificial Sequence
<220> FEATURE:
<223> OTHER INFORMATION: Synthetic sequence

<400> SEQUENCE: 5
cacttcaaag gtggtcccag agctgc                                               26

<210> SEQ ID NO 6
<211> LENGTH: 23
<212> TYPE: DNA
<213> ORGANISM: Artificial Sequence
<220> FEATURE:
<223> OTHER INFORMATION: Synthetic sequence

<400> SEQUENCE: 6
gaccggatcg gatccgtcag tcg                                                  23

<210> SEQ ID NO 7
<211> LENGTH: 22
<212> TYPE: DNA
<213> ORGANISM: Artificial Sequence
<220> FEATURE:
<223> OTHER INFORMATION: Synthetic sequence

<400> SEQUENCE: 7
gtcccggaca ctggaccagg cc                                                   22

<210> SEQ ID NO 8
<211> LENGTH: 27
<212> TYPE: DNA
<213> ORGANISM: Artificial Sequence
<220> FEATURE:
<223> OTHER INFORMATION: Synthetic sequence

<400> SEQUENCE: 8
ctccttttct tccagttgcc tagccaa                                              27

<210> SEQ ID NO 9
<211> LENGTH: 25
<212> TYPE: DNA
<213> ORGANISM: Artificial Sequence
<220> FEATURE:
<223> OTHER INFORMATION: Synthetic sequence

<400> SEQUENCE: 9
gagcaaggcc gaggagacgc agcgt                                                25

<210> SEQ ID NO 10
<211> LENGTH: 26
<212> TYPE: DNA
<213> ORGANISM: Artificial Sequence
<220> FEATURE:
<223> OTHER INFORMATION: Synthetic sequence

<400> SEQUENCE: 10
gagcctcctt tcgtccagc tgccgg                                                26
```

```
<210> SEQ ID NO 11
<211> LENGTH: 20
<212> TYPE: DNA
<213> ORGANISM: Artificial Sequence
<220> FEATURE:
<223> OTHER INFORMATION: Synthetic sequence

<400> SEQUENCE: 11
aggtcttcct ggagctgatg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic sequence

<400> SEQUENCE: 12
acccacaggg ccttctttac                                              20

<210> SEQ ID NO 13
<211> LENGTH: 24
<212> TYPE: DNA
<213> ORGANISM: Artificial Sequence
<220> FEATURE:
<223> OTHER INFORMATION: Synthetic sequence

<400> SEQUENCE: 13
acagcaaatt cacttacaca gttc                                         24

<210> SEQ ID NO 14
<211> LENGTH: 19
<212> TYPE: DNA
<213> ORGANISM: Artificial Sequence
<220> FEATURE:
<223> OTHER INFORMATION: Synthetic sequence

<400> SEQUENCE: 14
ctcattgcct tgcgtgttt                                               19
```

COMPOSITIONS AND METHODS OF USING TYROSINE KINASE INHIBITORS

CROSS-REFERENCE TO RELATED APPLICATION

This application is a continuation of, and claim priority of, U.S. patent application Ser. No. 15/544,401, filed Jul. 18, 2017, now allowed, which is a 35 U.S.C. § 371 national phase application from, and claims priority to, International Application No. PCT/US2016/014882, filed Jan. 26, 2016, and published under PCT Article 21(2) in English, which claims priority under 35 U.S.C. § 119(e) to U.S. Provisional Application Ser. No. 62/250,052, filed Nov. 3, 2015, and U.S. Provisional Application Ser. No. 62/107,553, filed Jan. 26, 2015, the contents of which are incorporated by reference herein in their entireties.

STATEMENT REGARDING FEDERALLY SPONSORED RESEARCH OR DEVELOPMENT

This invention was made with government support under GM099801 awarded by the National Institute of Health. The government has certain rights in the invention.

BACKGROUND OF THE INVENTION

Cardiovasular disease is the leading cause of death for both men and women worldwide despite significant advances. According to a report by the World Health Organization (WHO), it is estimated that 23.6 million people will die from cardiovascular diseases annually by 2030.

The RAS-MAPK pathway is critical for human growth and development. Abnormalities at different steps of this signaling cascade result in neuro-cardio-facial-cutaneous syndromes, or the RASopathies, a group of disorders with overlapping yet distinct phenotypes. RASopathy patients have variable degrees of intellectual disability, poor growth, relative macrocephaly, ectodermal abnormalities, dysmorphic features, and increased risk for certain malignancies. Significant locus heterogeneity exists for many of the RASopathies.

Congenital heart disease (CHD) is the most common defect found in newborns, occurring in about 1% of live births. Over 1 million people in the United States have some form of CHD, most of whom require continual monitoring and treatment to prevent deterioration of cardiac function. AVCD includes different anomalies of atrioventricular valves and atrial and ventricular septa. In the complete form, a single common atrioventricular valve and an atrial septal defect (ostium primum) confluent with a posterior ventricular septal defect in the inlet portion of the ventricular septum are found. In the partial form, there are two separate right and left atrioventricular valves with a clefted mitral valve, an atrial septal defect (ostium primum), and no ventricular septal communication. Cleft mitral valve is considered the less severe form of AVCD. AVCD is also the most common CHD found in children with Down syndrome and one of the structural heart defects most frequently associated with extracardiac anomalies in the setting of chromosomal and mendelian disorders. Distinct anatomic features are found in AVCD associated with NS. In fact, in general this defect is of the partial type, eventually associated with subaortic stenosis, due to accessory fibrous tissue and/or anomalous insertion of the mitral valve with anomalous papillary muscle of the left ventricle.

Congenital heart disease (CHD) occurs in approximately 60-86% of patients affected by a RASopathy, a group of disorders with abnormalities in the RAS-MAPK pathway. Pulmonary valve stenosis (PVS) and hypertrophic cardiomyopathy are the most common defects displaying a distinct association with the RASopathies. The spectrum of CHDs in Noonan syndrome with multiple lentigines (NSML) is wider, and the family of atrioventricular canal defects (AVCD) is the third most common heart defect.

Most patients with cardiovascular disease and RASopathy-associated congenital heart disease need treatment for many years. In particular, RASopathy-associated congenital heart disease are usually associated with low mortality rates. Therefore a need exists to treat cardiovascular disease in patients with low risk therapies having maximal effect on heart disease.

SUMMARY OF THE INVENTION

As described below, the present invention includes compositions and methods to aberrant inhibit protein tyrosine phosphorylation, such as phosphorylation of Src family tyrosine kinases and their substrates.

In one aspect, the invention includes a method of treating a cardiovascular disease or condition having aberrant protein tyrosine phosphorylation in a subject, comprising administering a low-dosage of a tyrosine kinase inhibitor to a subject in need thereof, wherein the tyrosine kinase inhibitor decreases aberrant levels of tyrosine phosphorylation and improves at least one cardiac function in the subject.

In another aspect, the invention includes a method of treating congenital heart disease comprising administering a low-dosage of a tyrosine kinase inhibitor to a subject in need thereof, wherein the tyrosine kinase inhibitor decreases aberrant levels of tyrosine phosphorylation and improves at least one cardiac function in the subject.

In yet another aspect, the invention includes a method of treating a cardiovascular disease or condition associated with a RASopathy having aberrant protein tyrosine phosphorylation comprising administering a low-dosage of a tyrosine kinase inhibitor to a subject in need thereof, wherein the tyrosine kinase inhibitor decreases aberrant levels of tyrosine phosphorylation and improves at least one cardiac function in the subject.

In still another aspect, the invention includes a composition comprising a low-dosage tyrosine kinase inhibitor, wherein the low-dosage tyrosine kinase inhibitor is capable of decreasing tyrosine phosphorylation and improving at least one cardiac function in a subject in need thereof.

In another aspect, the invention includes a pharmaceutical composition comprising the composition as described herein and a pharmaceutically acceptable carrier.

In yet another aspect, the invention includes use of the composition as described herein in the manufacture of a medicament for the treatment of cardiovascular disease or condition in a subject.

In various embodiments of the above aspects or any other aspect of the invention delineated herein, the congenital heart disease is associated with a RASopathy, such as a RASopathy selected from the group consisting of Neurofibromatosis Type 1, Noonan syndrome, Noonan syndrome with multiple lentigines (Leopard syndrome), capillary malformation-arteriovenous malformation syndrome, Costello syndrome, cardio-facio-cutaneous syndrome, and Legius syndrome. In one embodiment, the cardiovascular disease or condition is congenital heart disease.

In another embodiment, the low-dosage is in the range of about 175 fold to about 250 fold lower than a chemotherapeutic dosage of the tyrosine kinase inhibitor.

In another embodiment, the cardiac function is selected from the group consisting of myofibrilar organization, cardiomyocyte contractility, SERCA2A expression, and cardiac fibrosis.

In another embodiment, the tyrosine kinase inhibitor is selected from the group consisting of afatinib, axitinib, bosutinib, cabozantinib, cediranib, ceritinib, crizotinib, dabrafenib, dasatinib, erlotinib, everolimus, gefitinib, ibrutinib, imatinib, lapatinib, lenvatinib, lestaurtinib, nilotinib, nintedanib, palbociclib, pazopanib, ponatinib, regorafenib, ruxolitinib, semananib, sirolimus, sorafenib, sunitinib, temsirolimus, tofacitinib, trametinib, vandetanib, and vemurafenib. In yet another embodiment, the tyrosine kinase inhibitor is a Src family tyrosine kinase inhibitor, such as a Src family tyrosine kinase inhibitor selected from the group consisting A419259, AP23451, AP23464, AP23485, AP23588, AZD0424, AZM475271, BMS354825, CGP77675, CU201, ENMD 2076, KB SRC 4, KX2361, KX2-391, MLR 1023, MNS, PCI-32765, PD166285, PD180970, PKC-412, PKI166, PP1, PP2, SRN 004, SU6656, TC-S7003, TG100435, TG100948, TX-1123, VAL 201, WH-4-023, XL 228, altenusin, bosutinib, damnacanthal, dasatinib, herbimycin A, indirubin, neratinib, lavendustin A, pelitinib, piceatannol, saracatinib, SrcI1, and analogs thereof.

In another embodiment, the subject is a pediatric patient, such as a pediatric subject less than 12 years of age. In yet another embodiment, the subject is greater than 18 years of age.

In another embodiment, the aberrant levels of tyrosine phosphorylation comprise aberrant levels of tyrosine phosphorylated Protein Zero-Related (PZR). In such an embodiment, the low-dosage tyrosine kinase inhibitor decreases PZR tyrosine phosphorylation. In yet another embodiment, the low-dosage tyrosine kinase inhibitor provides an anti-fibrotic effect in cardiac tissue to the subject. In still another embodiment, the low-dosage tyrosine kinase inhibitor decreases aberrant tyrosine phosphorylation of a transmembrane glycoprotein, such as the transmembrane glycoprotein Protein Zero-Related (PZR). In another embodiment, the low-dosage tyrosine kinase inhibitor provides an anti-fibrotic effect in cardiac tissue.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments, which are presently preferred. It should be understood, however, that the invention is not limited to the precise arrangements and instrumentalities of the embodiments shown in the drawings.

FIG. 1E shows amino acid sequences of the protein zero-related (PZR) C terminus in different vertebrates. Consensus sequences for immunoreceptor tyrosine-based inhibitory motif (ITIM; S/I/V/LXYXXI/V/L) are indicated in boldface, and tyrosine residues are marked with the appropriate amino acid numbering. Sequences are shown for the PZR C terminus from Homo sapiens, Mus musculus, Rattus norvegicus, Bos taurus, Canis lupus familiaris, Danio rerio, Gallus gallus.

FIG. 2C is a panel of blots showing the characterization of PZR tyrosyl phosphorylation. HUVECs were infected with adenoviruses expressing either GFP as a control, wild-type Shp2, or Shp2E76A. Cell lysates were immunoblotted with anti-pPZR (Y241 or Y263), anti-total PZR, and anti-Shp2 antibodies.

FIG. 2D is a panel of blots showing the characterization of PZR tyrosyl phosphorylation. HEK-293 cells were transiently transfected with empty vector, wild-type Shp2 (WT), or the indicated Shp2 mutants (activated Shp2, E76A; Noonan syndrome (NS) mutant, N308D; or Noonan syndrome with multiple lentigines (NSML) mutants, Y279C and T468M). Cell lysates were immunoblotted with anti-pPZR (Y241 or Y263), -PZR, and -Shp2 antibodies. ERK1/2 was used as a loading control.

FIG. 2E is a panel of blots showing the characterization of PZR tyrosyl phosphorylation. HEK-293T cells were transfected with HA-tagged zebrafish PZR with empty vector, wild-type Shp2, Shp2D61G (NS mutant), or Shp2A462T (NSML mutant). Cell lysates were immunoprecipitated with anti-HA antibodies, and immune complexes were immunoblotted with anti-Shp2 and anti-HA antibodies. Whole-cell lysates (WCL) were blotted with anti-pPZR (Y241 and Y263), -Shp2, and -HA antibodies.

FIG. 5C is a panel of images showing ERK and Akt phosphorylation in the heart of Ptpn11$^{Y279C/+}$ mice. The hearts were isolated from 8-week-old wild-type and Ptpn11$^{Y279C/+}$ mice. Tissue lysates were subjected to immunoblotting with anti-Shp2, -pERK1/2, -total ERK1/2, -pAkt, and -Akt antibodies. The results represent densitometric analyses of the means±SEM for pERK1/2 and pAkt from 5 mice per genotype.

FIG. 5D is a panel of images showing ERK and Akt phosphorylation in the cortex of Ptpn11$^{Y279C/+}$ mice. The cortex was isolated from 8-week-old wild-type and Ptpn11$^{Y279C/+}$ mice. Tissue lysates were subjected to immunoblotting with anti-Shp2, -pERK1/2, -total ERK1/2, -pAkt, and -Akt antibodies. The results represent densitometric analyses of the means±SEM for pERK1/2 and pAkt from 5 mice per genotype.

FIG. 7A is a blot showing that Src kinase mediated NS- or NSML-Shp2-induced PZR hyper-tyrosyl phosphorylation. SYF cells (Src$^{-/-}$ Fyn$^{-/-}$ Yes$^{-/-}$ MEFs) and Src$^{+/+}$ cells (SYF cells expressing wild-type Src) were infected with adenoviruses expressing either GFP or Shp2E76A. Cell lysates were immunoblotted with anti-Shp2, pSrc (Y416), pPZR (Y241 or Y263), PZR, and Src antibodies. ERK1/2 was used as a loading control.

FIG. 7B is a blot showing that Src kinase mediated NS- or NSML-Shp2-induced PZR hyper-tyrosyl phosphorylation. SYF cells were transiently transfected with wild-type c-Src or kinase-dead c-SrcK295R/Y527F (KR/YF) and infected with adenoviruses expressing either GFP, wild-type Shp2, or Shp2E76A. Cell lysates were immunoblotted with anti-Shp2, pSrc (Y416), pPZR (Y241 or Y263), PZR, and Src antibodies. ERK1/2 was used as a loading control.

Cell lysates were immunoblotted with anti-pPZR (Y241 or Y263) or Shp2 antibodies. ERK1/2 was used as a loading control. Immune complexes were immunoblotted with anti-Src, -Shp2, and -PZR antibodies.

Figure 9:
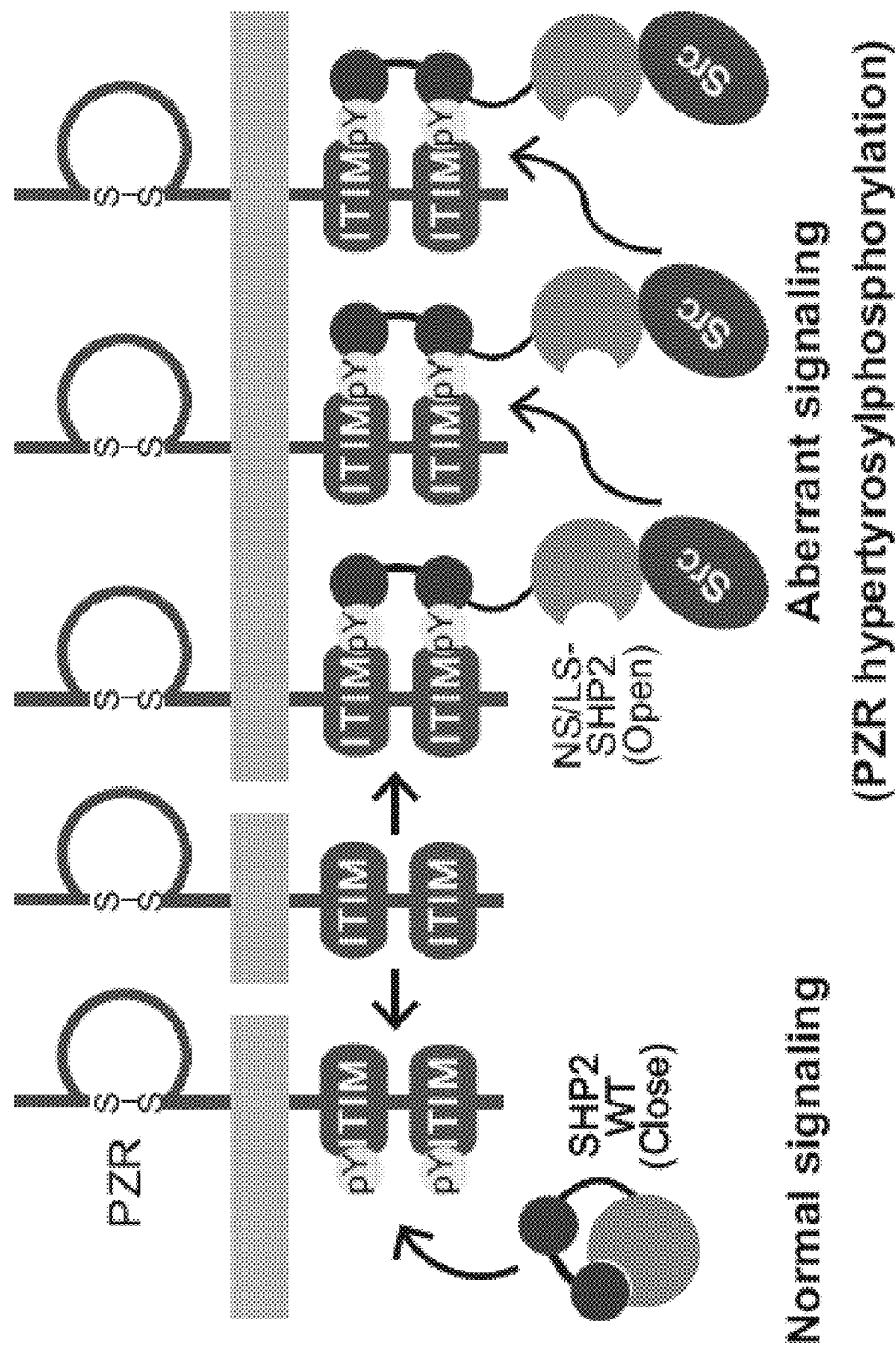

FIG. 9 is an illustration of the model for the effects of NS and NSML mutants on PZR tyrosyl phosphorylation.

Figure 10:
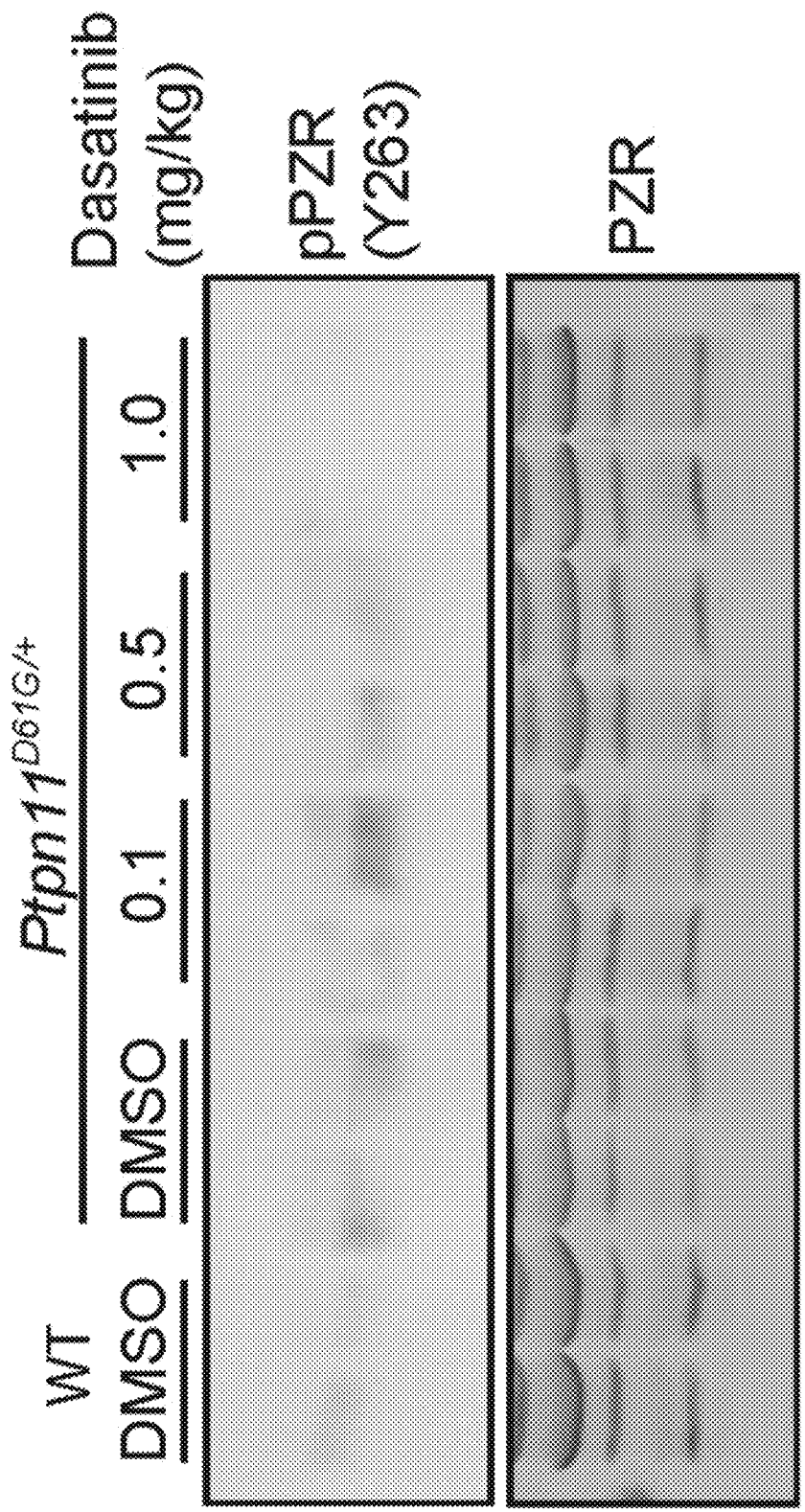

FIG. 10 is a panel of images showing dosing of dasatinib. Male Ptpn11D61G/+ mice were injected i.p. with dasatinib at the indicated dose or DMSO control, 24 h later mice were sacrificed, heart tissue harvested and immunoblotted using the indicated antibodies.

Figure 11A:
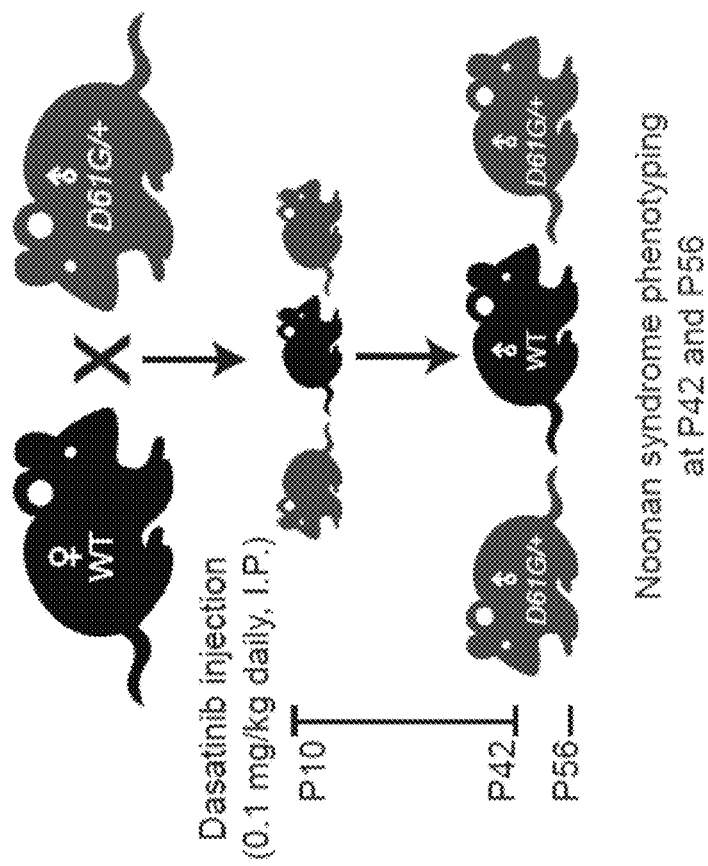

FIG. 11A is an illustration showing the pre-natal dosing regimen for dasatinib in NS mouse model. Dasatinib was administered daily to pregnant mothers between the time of when animals were in utero at E7.5 until 9 days after birth (P9). At post-natal day 10 (P10), mice received dasatinib directly by daily injections for 46 days (P56). Mice were evaluated for cardiac function at P42 and P56.

Figure 11B:
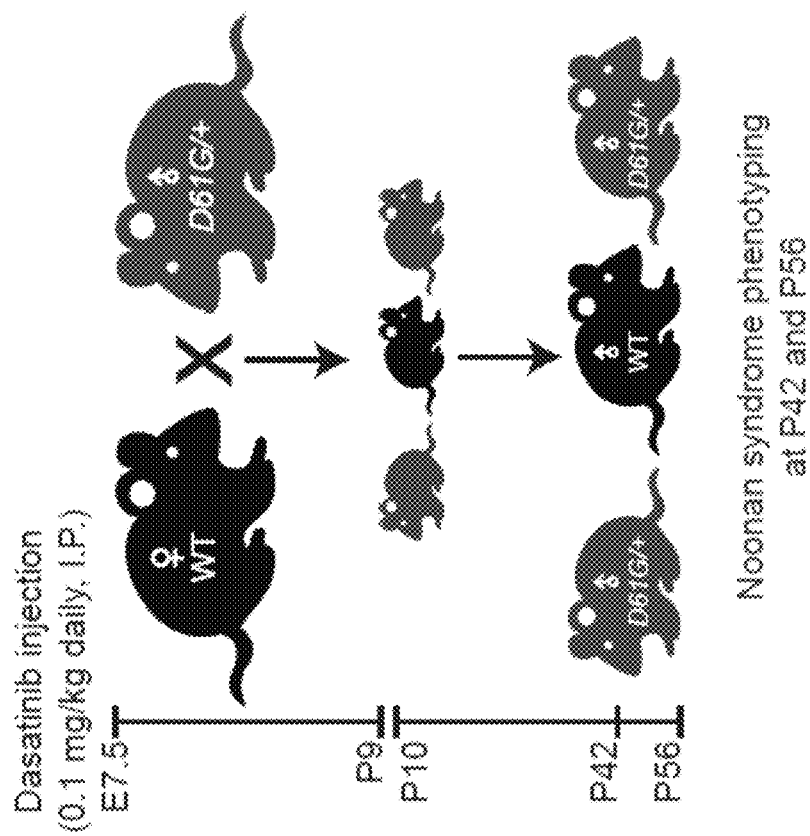

FIG. 11B is an illustration showing the post-natal dosing regimen for dasatinib in NS mouse model. Dasatinib was administered to mice starting at P10 daily for 32 days (P42) and discontinued for 14 days (P56). Mice were evaluated for cardiac function at P42 and P56.

Figure 12A:
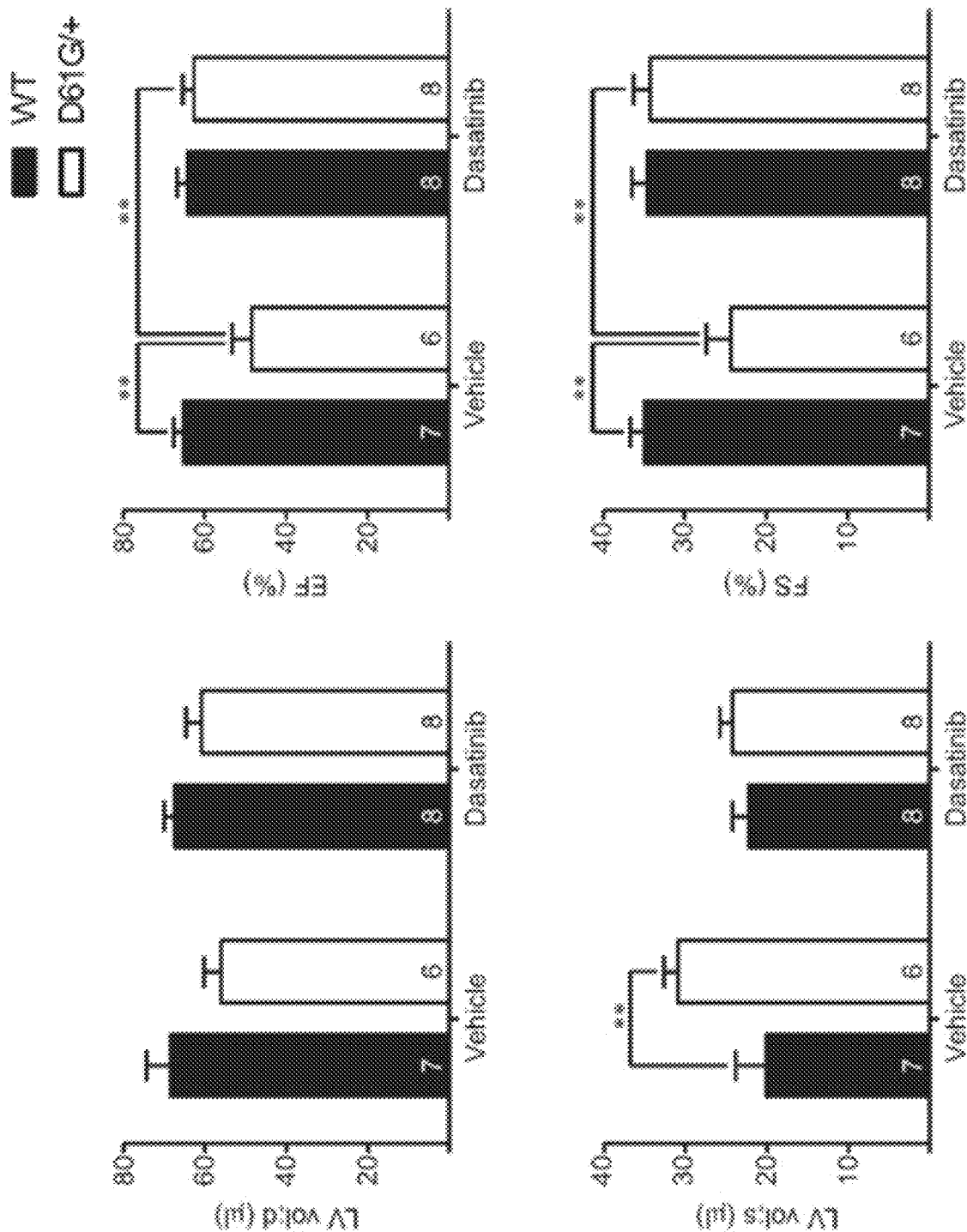

FIG. 12A is a panel of graphs showing dasatinib-treated pre-natally in NS mice improves cardiac function. Pregnant mice were injected i.p. with dasatinib (0.1 mg/kg) according to protocol described herein. The number of mice for each group is indicated. Statistical significance is indicated by; *; P<0.05, ; P<0.01, *; P<0.001 by two-way ANOVA test. LV vol;s—Left ventricular volume in systole, LV vol;d—Left ventricular volume in diastole, FS—Fractional shortening and EF—Ejection fraction.

Figure 12B:
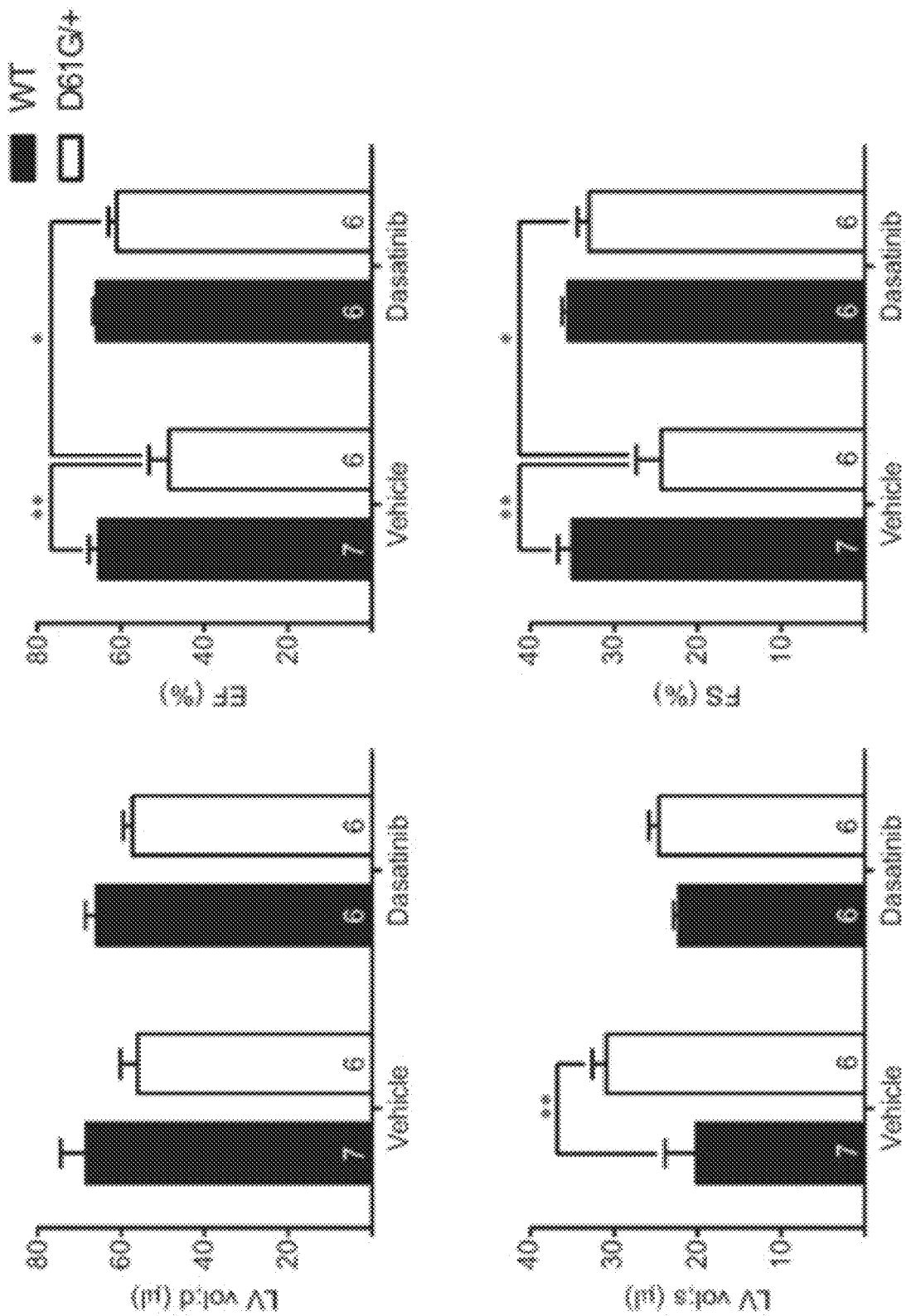

FIG. 12B is a panel of graphs showing dasatinib-treated in post-natal NS mice improves cardiac function. NS mice starting at P10 were injected i.p. with Disatinib (0.1 mg/kg) according to the protocol described herein. Mice were evaluated for cardiac function after 32 days of treatment. The number of mice for each group is indicated. Statistical significance is indicated by; *; P<0.05, ; P<0.01, *; P<0.001 by two-way ANOVA test. LV vol;s—Left ventricular volume in systole, LV vol;d—Left ventricular volume in diastole, FS—Fractional shortening and EF—Ejection fraction.

Figure 12C:
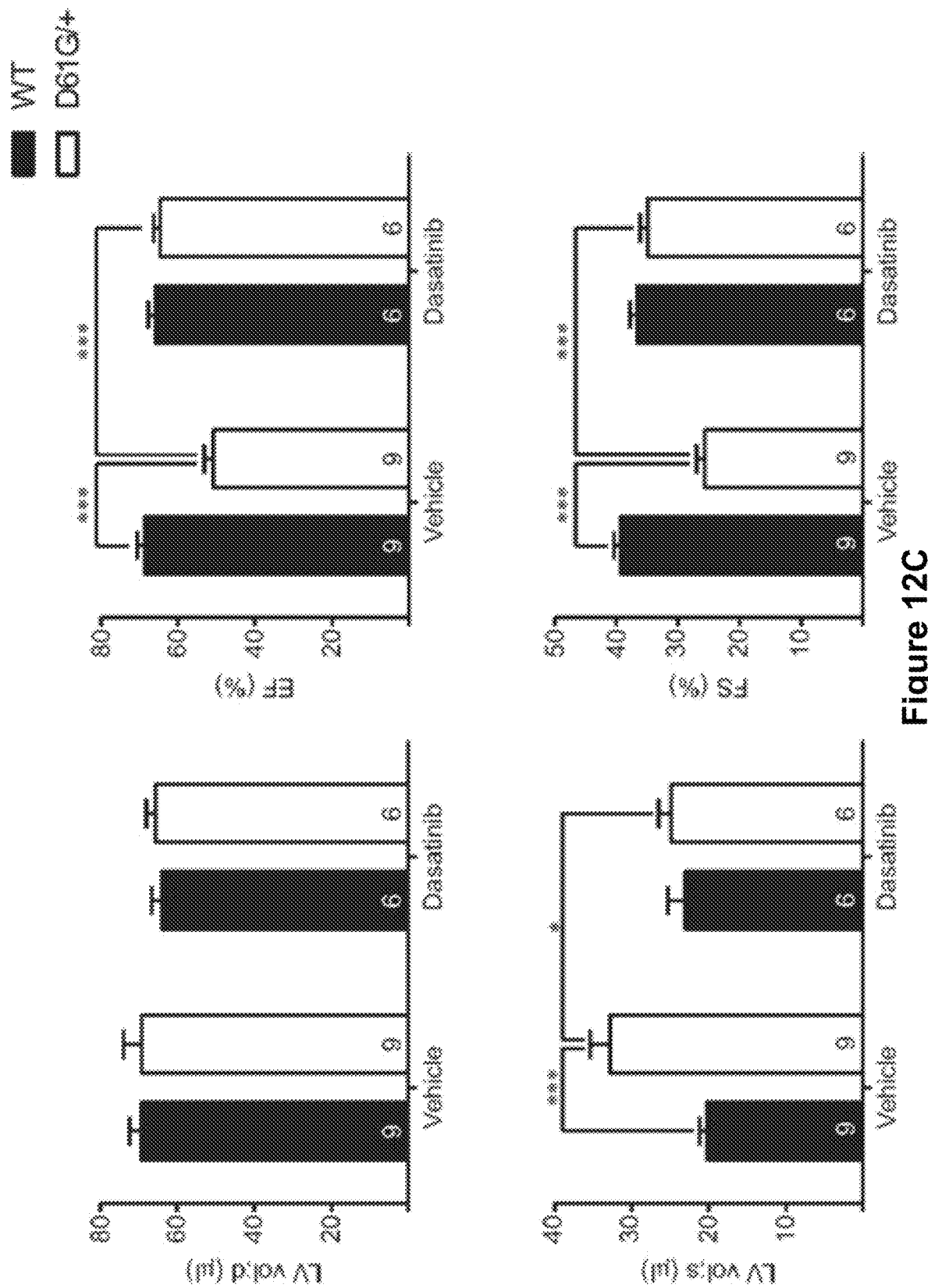

FIG. 12C is a panel of graphs showing preserved improvement of cardiac function after cessation of dasatinib treatment. NS mice starting at P10 were injected i.p. with dasatinib (0.1 mg/kg) according to the protocol shown in FIG. 1B. Mice that had received dasatinib for 32 days were re-evaluated for cardiac function two weeks later. The number of mice for each group is indicated. Statistical significance is indicated by; *; P<0.05, ; P<0.01, *; P<0.001 by two-way ANOVA test. LV vol;s—Left ventricular volume in systole, LV vol;d—Left ventricular volume in diastole, FS—Fractional shortening and EF—Ejection fraction.

Figures 13A, 13B, 13C:
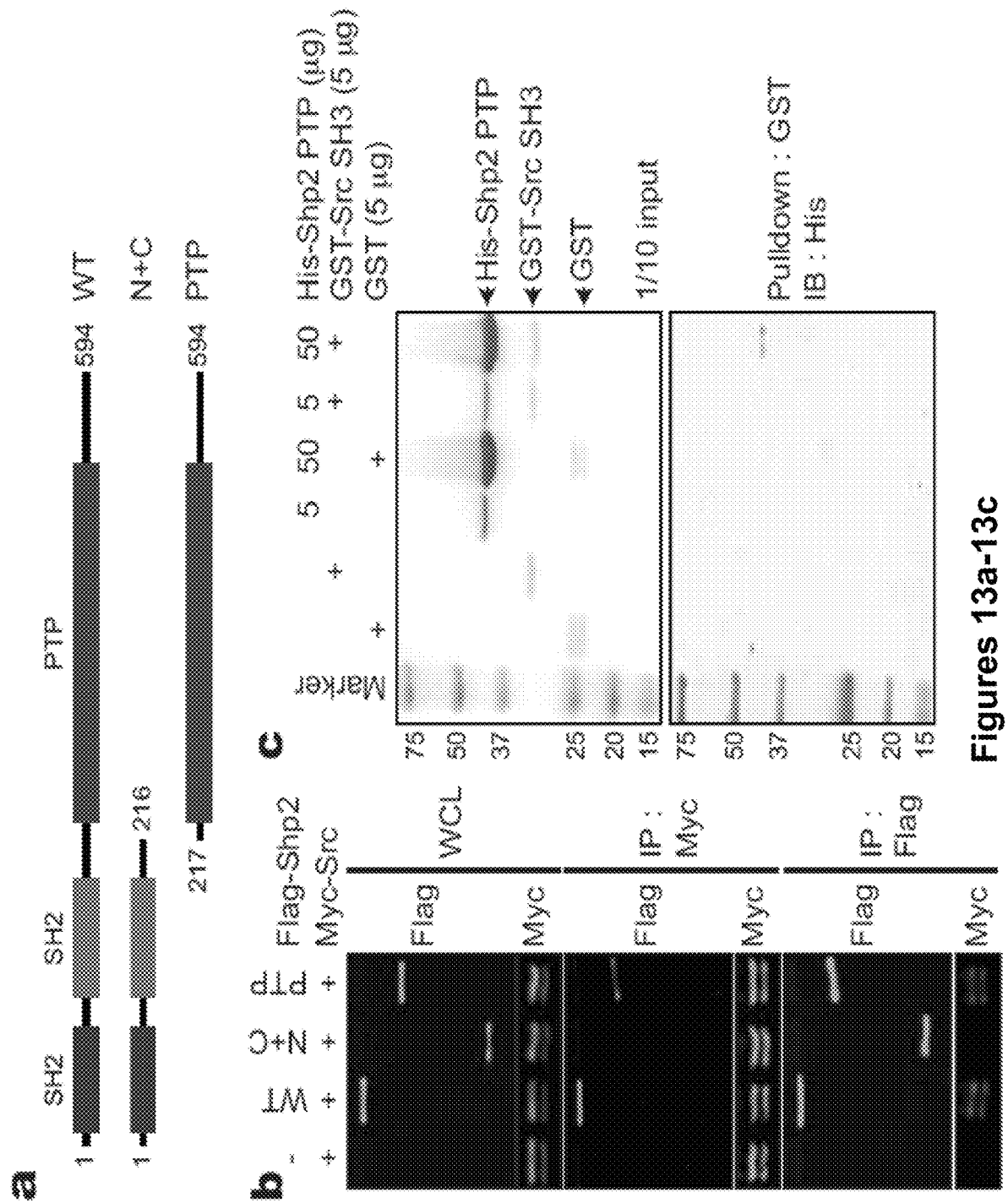
Figures 13D, 13E, 13F, 13G, 13H:
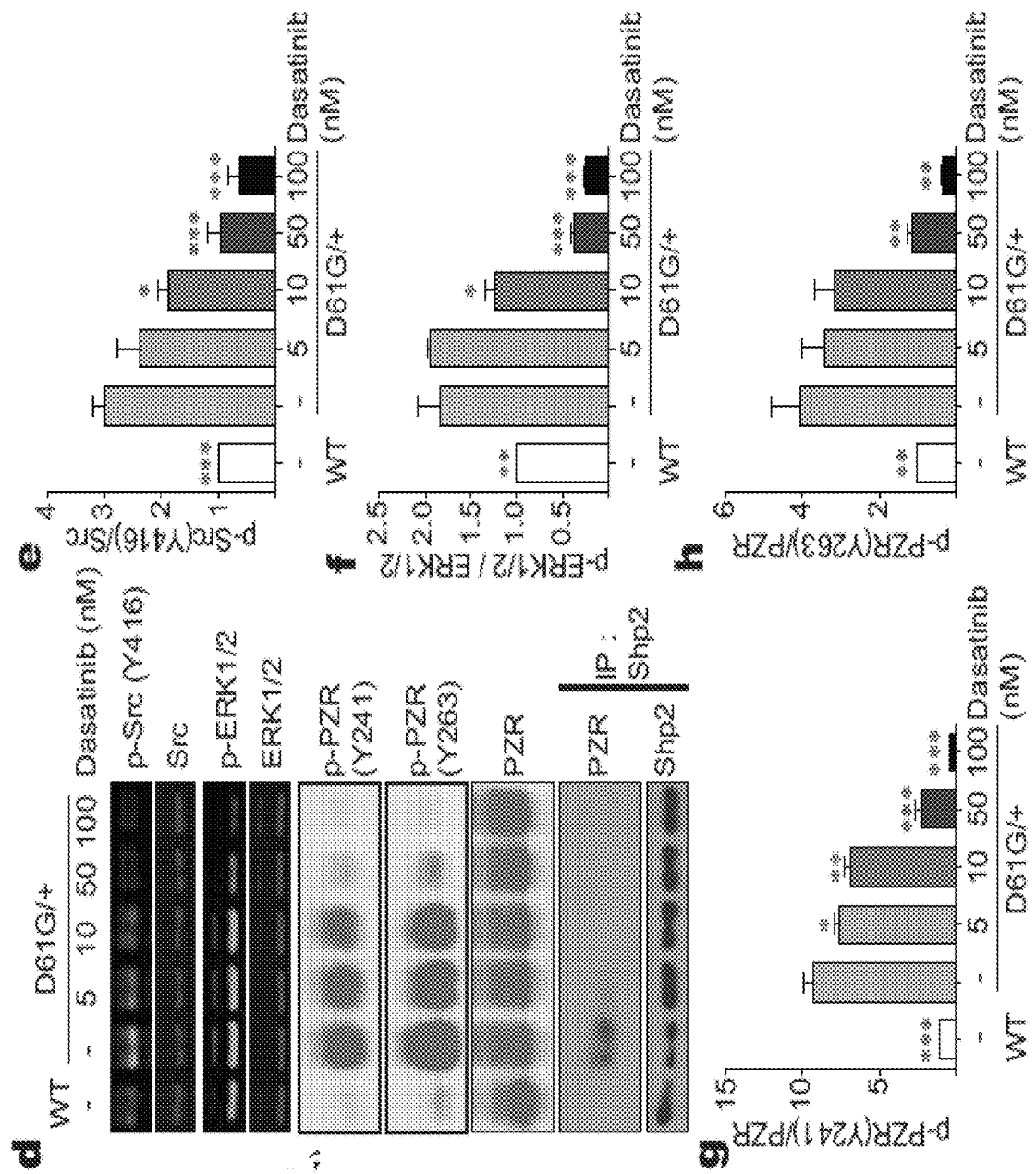
Figures 13I, 13J, 13K, 13L:
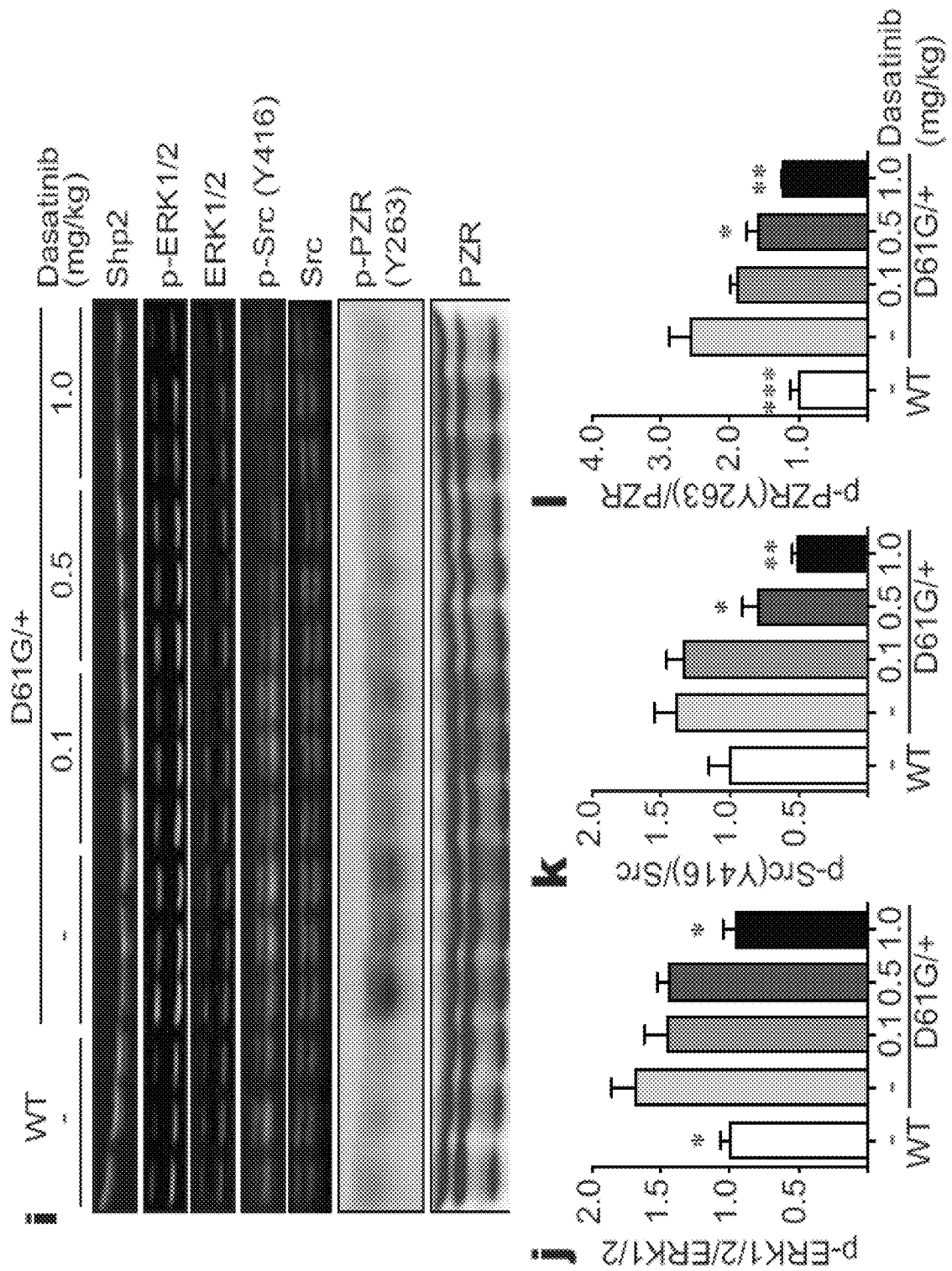

FIGS. 13a-13l are a panel of images showing c-Src kinase is a putative target for Noonan syndrome. FIG. 13a is a schematic diagram of human Shp2 wild type full-length, N+C-SH2 and PTP domain constructs. FIG. 13b is an image showing detection of Myc-Src full-length co-transfected with Flag-Shp2 full-length, N+C or PTP domain into HEK-293T cells. Protein-protein interactions were determined by immunoprecipitation. FIG. 13c is an image showing detection of purified GST-SH3 domain of c-Src incubated with purified His-tagged PTP domain of Shp2 overnight at 4° C. Proteins were immobilized with GST-Sepharose beads and separated by SDS-PAGE. His-PTP domain was detected in GST complexes by immunoblotting with anti-His antibodies. FIG. 13d is an image showing the phosphorylation levels of Src (Y416). Mouse embryonic fibroblasts (MEFs) from Ptpn11$^{D61G/+}$ mice incubated with dasatinib at the indicated concentrations for 18 hr. Whole cell lysates were immunoblotted with anti-p-Src (Y416), Src, p-ERK1/2 and ERK1/2 antibodies. Tyrosyl-phosphorylation of PZR was determined with phospho-specific PZR antibodies and the molecular interaction between PZR and Shp2 was determined by immunoprecipitation. FIG. 13e is a graph showing phosphorylation levels of Src (Y416). FIG. 13f is a graph showing phosphorylation levels of ERK1/2. FIG. 13g is a graph showing the amounts of PZR phosphorylation at tyrosine 241. FIG. 13h is a graph showing the amounts of tyrosine 263 analyzed by densitometry. FIG. 13i is an image showing heart tissue immunoblotted with anti-Shp2, p-ERK1/2, ERK1/2, p-Src (Y416), Src, p-PZR (Y263) and PZR antibodies. 3-week-old WT and Ptpn11$^{D61G/+}$ mice were intraperitoneally injected with vehicle or dasatinib (0.1, 0.5 or 1.0 mg/kg). Heart tissue was isolated after 18 hr and tissue lysates were immunoblotted. FIG. 13j is a graph showing tyrosyl phosphorylation of ERK1/2. FIG. 13k is a graph showing tyrosyl phosphorylation of Src. FIG. 13l is a graph showing tyrosyl phosphorylation of PZR. All data present mean±SEM. *, p<0.05; , p<0.01; *, p<0.001 denote significance compared with the vehicle treated Ptpn11$^{D61G/+}$ MEFs (e-h) or heart tissues (j-l) (n=3 for each condition; One-way ANOVA test). WCL: whole cell lysates, IP: immunoprecipitation, IB: immunoblotting.

Figures 14A, 14B, 14C, 14D, 14E:
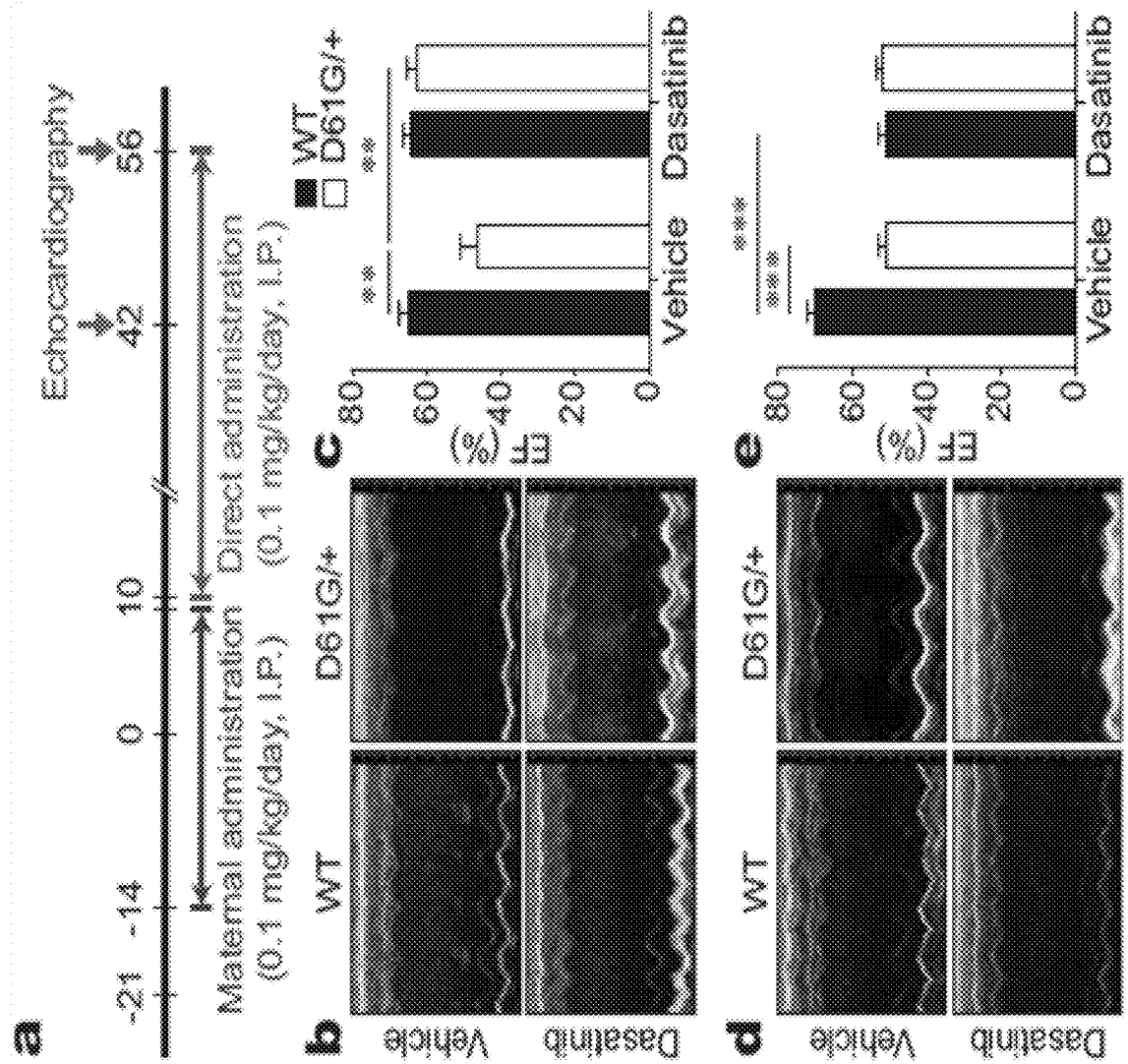
Figures 14F, 14G, 14H, 14I, 14J:
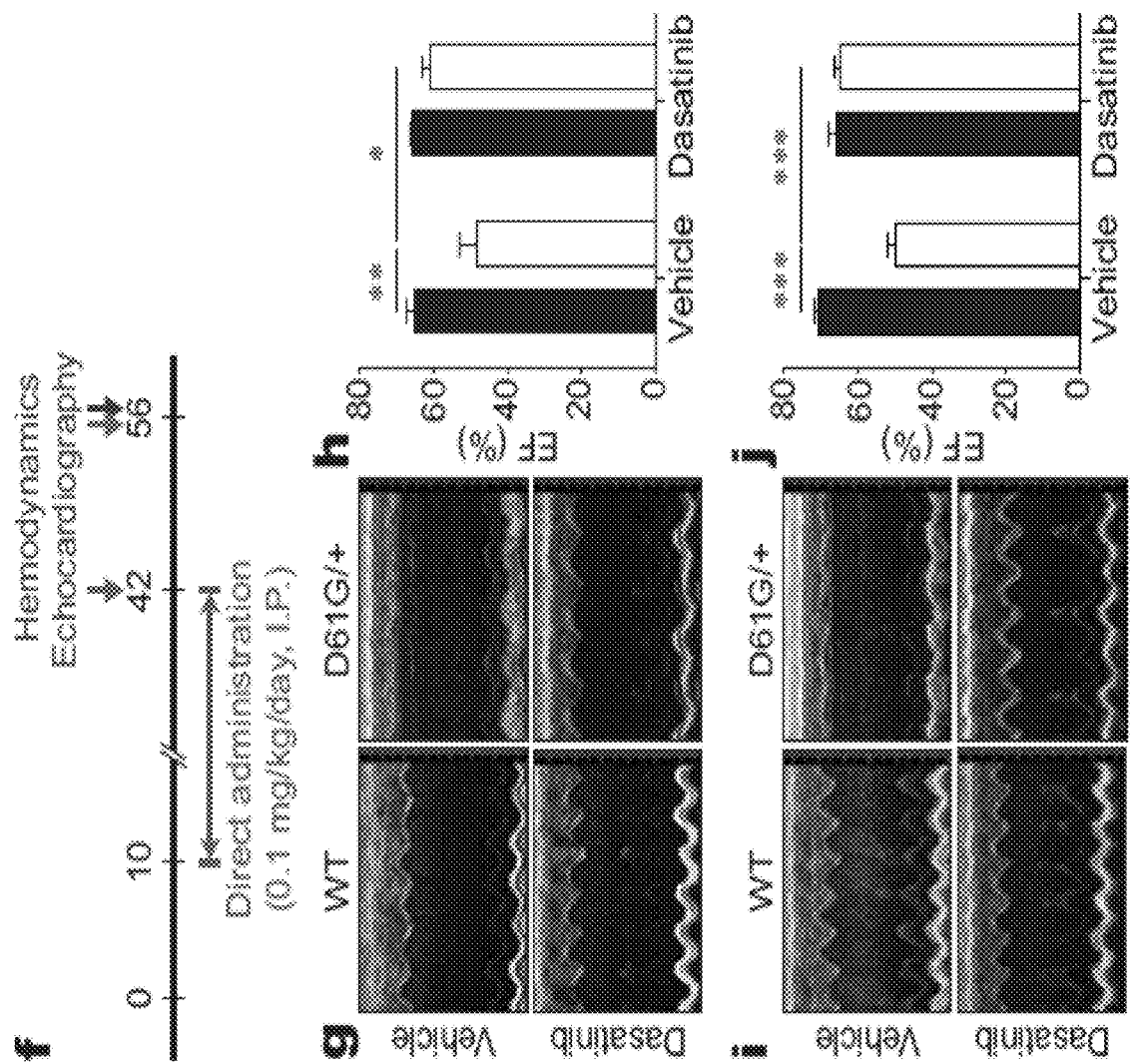

FIGS. 14a-14n are a panel of images showing that dasatinib improves cardiac functions of Ptpn11$^{D61G/+}$ mice. FIG. 14a is a schematic diagram of prenatal dasatinib administration into Ptpn11$^{D61G/+}$ mice. FIG. 14b is a panel of images showing representative echocardiographic images of vehicle- or dasatinib-treated WT and Ptpn11$^{D61G/+}$ mice at P42. FIG. 14c is a graph showing the percentage of ejection fraction (EF) measured from echocardiogram at P42. FIG. 14d is a panel of images showing representative echocardiographic images of vehicle- or asatinib-treated WT and Ptpn11$^{D61G/+}$ mice at P56. FIG. 14e is a graph showing the percentage of ejection fraction (EF) measured from echocardiogram at P56. FIG. 14f is a schematic diagram of prenatal dasatinib administration into Ptpn11$^{D61G/+}$ mice. FIG. 14g is a panel of images showing representative echocardiographic images of vehicle- or dasatinib-treated WT and Ptpn11$^{D61G/+}$ mice at P42. FIG. 14h is a graph showing the percentage of ejection fraction (EF) was measured from echocardiogram at P42. FIG. 14i is a panel of images showing representative echocardiographic images of vehicle- or dasatinib-treated WT and Ptpn11$^{D61G/+}$ mice at P56. FIG. 14j is a graph showing the percentage of ejection fraction (EF) was measured from echocardiogram at P56. FIG. 14k is a graph showing arterial systolic pressure from an invasive hemodynamic study of postnatal vehicle- or dasatinib-treated WT and Ptpn11$^{D61G/+}$ mice at P56. FIG. 14l is a graph showing the diastolic pressure of postnatal vehicle- or dasatinib-treated WT and Ptpn11$^{D61G/+}$ mice at P56. FIG. 14m is a graph showing the mean arterial pressure (MAP) of postnatal vehicle- or dasatinib-treated WT and Ptpn11$^{D61G/+}$ mice at P56. FIG. 14n is a graph showing the left ventricle blood pressure (LV pressure) of postnatal vehicle- or dasatinib-treated WT and Ptpn11$^{D61G/+}$ mice at P56. All data present mean±SEM. *, p<0.05; , p<0.01; *, p<0.001. (n=10~16 for each group; Two-way ANOVA test).

Figures 15A, 15B, 15C:
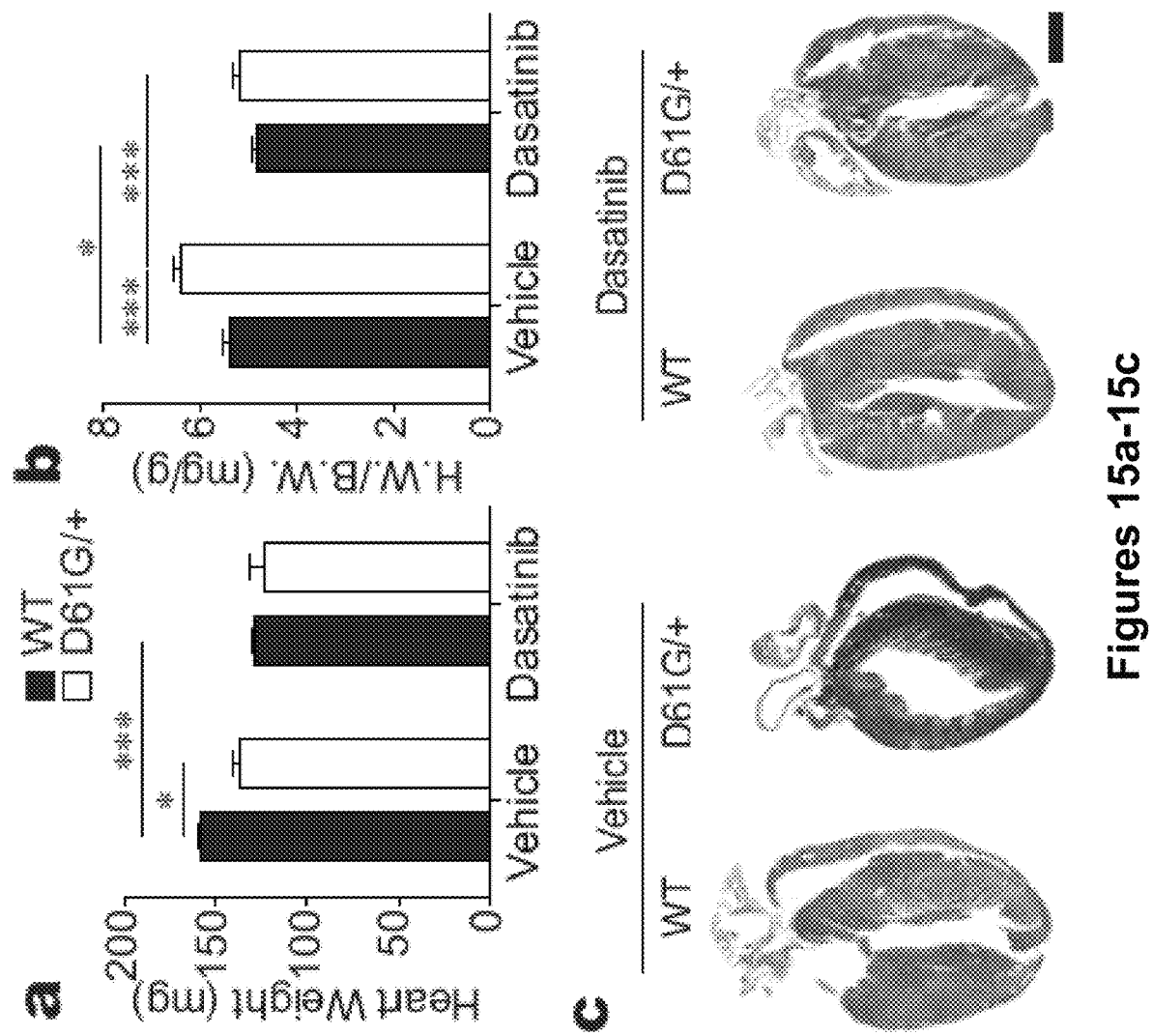
Figures 15D, 15E, 15F:
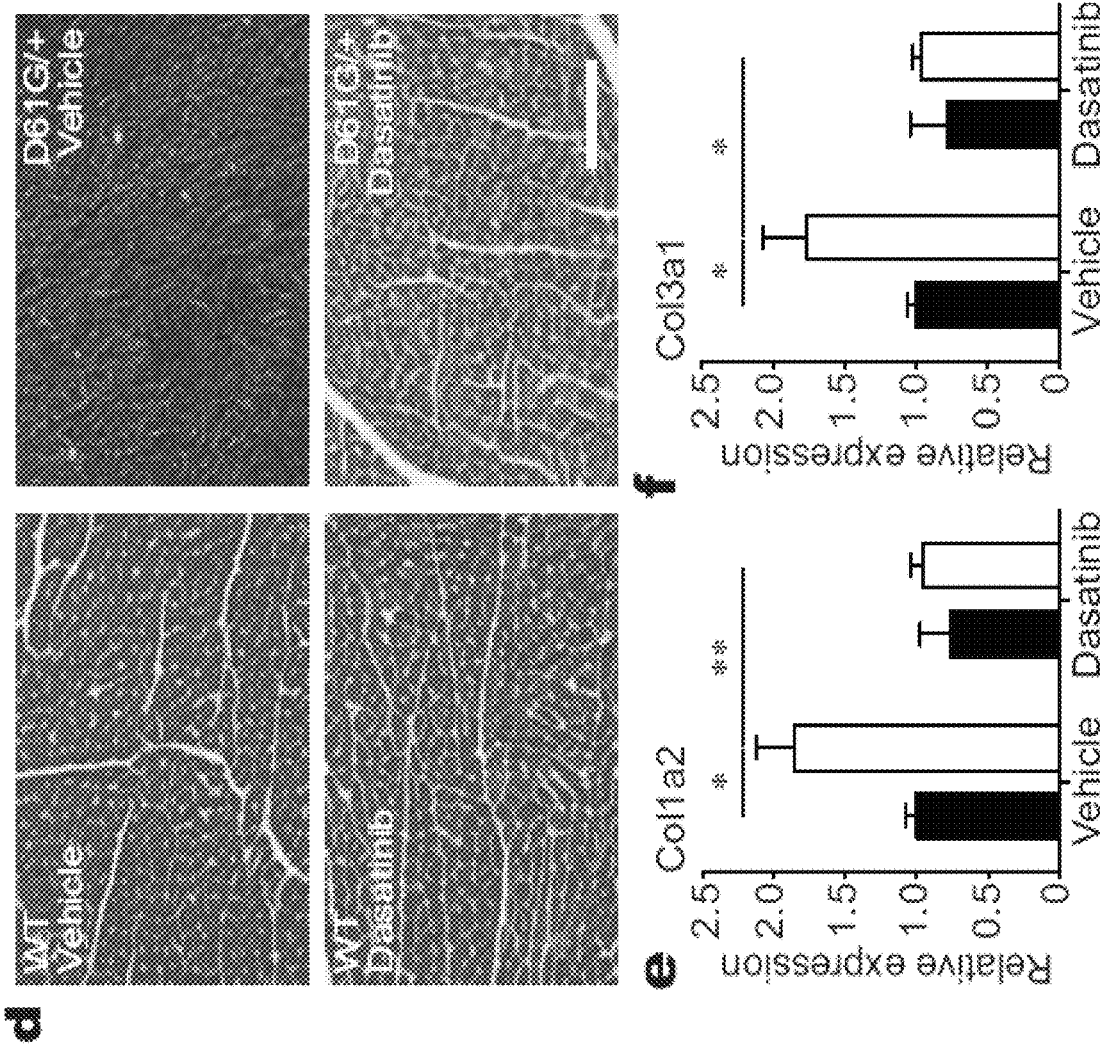
Figures 15G, 15H, 15I, 15J:
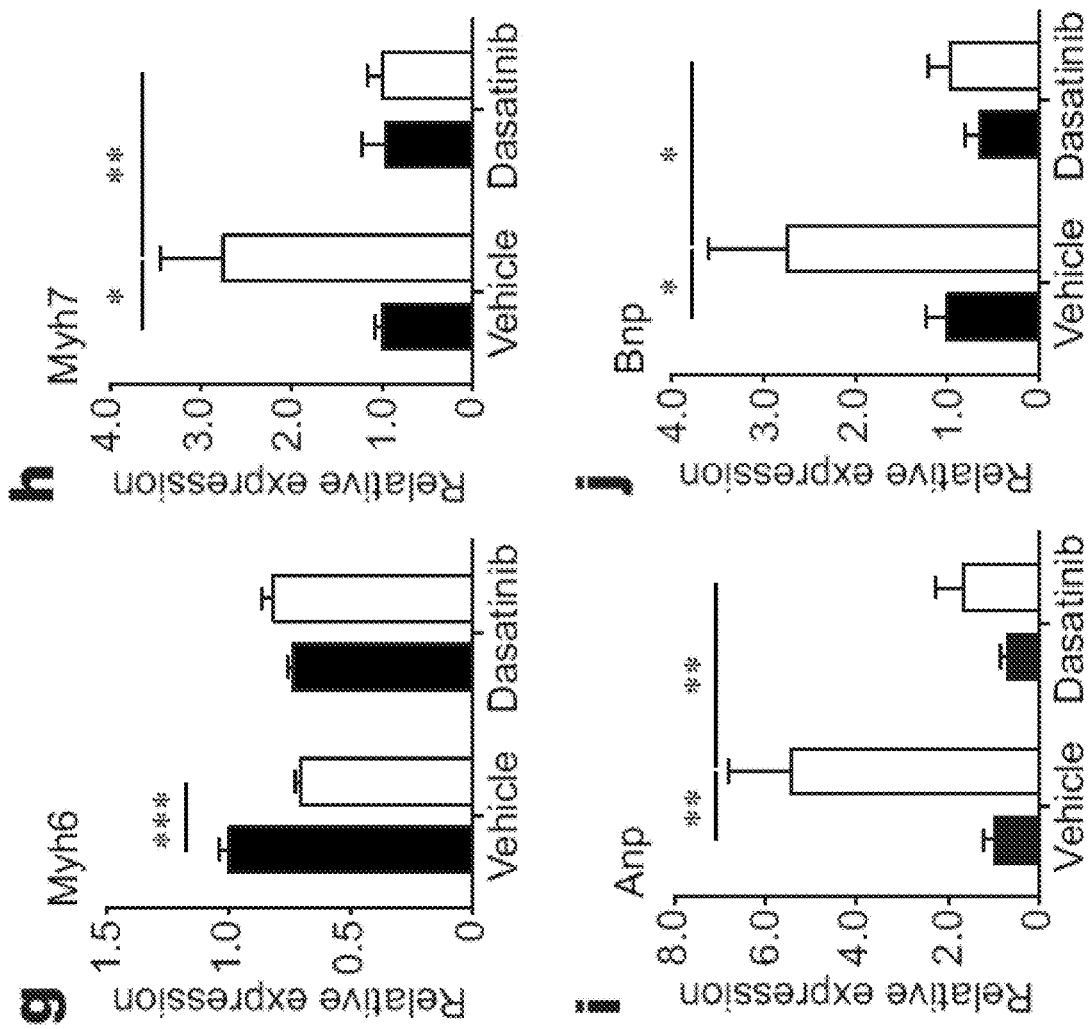

FIGS. 15a-15j are a panel of images showing cardiomyopathy and cardiac fibrosis in Ptpn11$^{D61G/+}$ mice rescued by dasatinib. FIG. 15a is a graph showing heart weight measured from postnatal vehicle- or dasatinib-treated WT and Ptpn11$^{D61G/+}$ mice at P56 (n=8~9 for each group). FIG. 15b is a graph showing heart weight (H.W.) to body weight (B.W.) ratio measured from postnatal vehicle- or dasatinib-treated WT and Ptpn11$^{D61G/+}$ mice at P56 (n=8~9 for each group). FIG. 15c is a panel of images showing the representative images of Masson's trichrome stained longitudinal sections of heart from postnatal vehicle- or dasatinib-treated WT and Ptpn11$^{D61G/+}$ mice at P56 (bar=2 mm). FIG. 15d is a panel of images showing Masson's trichrome stain images of left ventricle from postnatal vehicle- or dasatinib-treated WT and Ptpn11$^{D61G/+}$ mice at P56 (bar=200 μm). FIG. 15e is a graph showing relative expression of fibrosis marker gene, Col1a2. Total heart RNA was isolated from postnatal vehicle- or dasatinib-treated WT and Ptpn11$^{D61G/+}$ mice (P56). FIG. 15f is a graph showing relative expression of fibrosis marker gene, Col3a1. FIG. 15g is a graph showing relative expression of cardiac fetal gene, Myh6 (αMHC). FIG. 15h is a graph showing relative expression of cardiac fetal gene, Myh7 (βMHC). FIG. 15i is a graph showing relative expression of cardiac fetal gene, Anf. FIG. 15j is a graph showing relative expression of cardiac fetal gene, Bnp. The genes were measured by quantitative RT-PCR (n=6 for each group). All data present mean±SEM. *, p<0.05; , p<0.01; *, p<0.001. (Two-way ANOVA test).

Figures 16A, 16B, 16C:
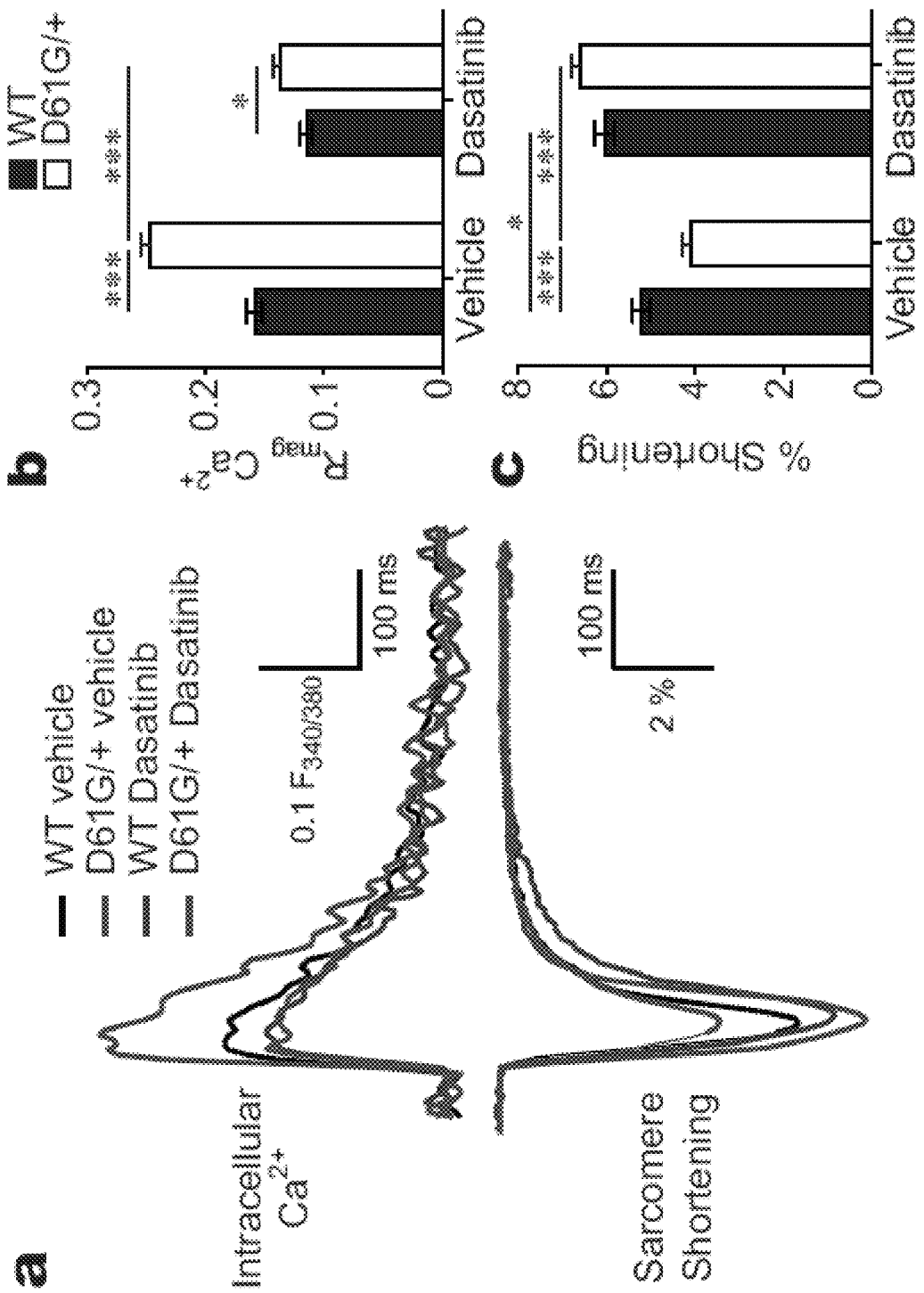
Figures 16D, 16E, 16F, 16G:
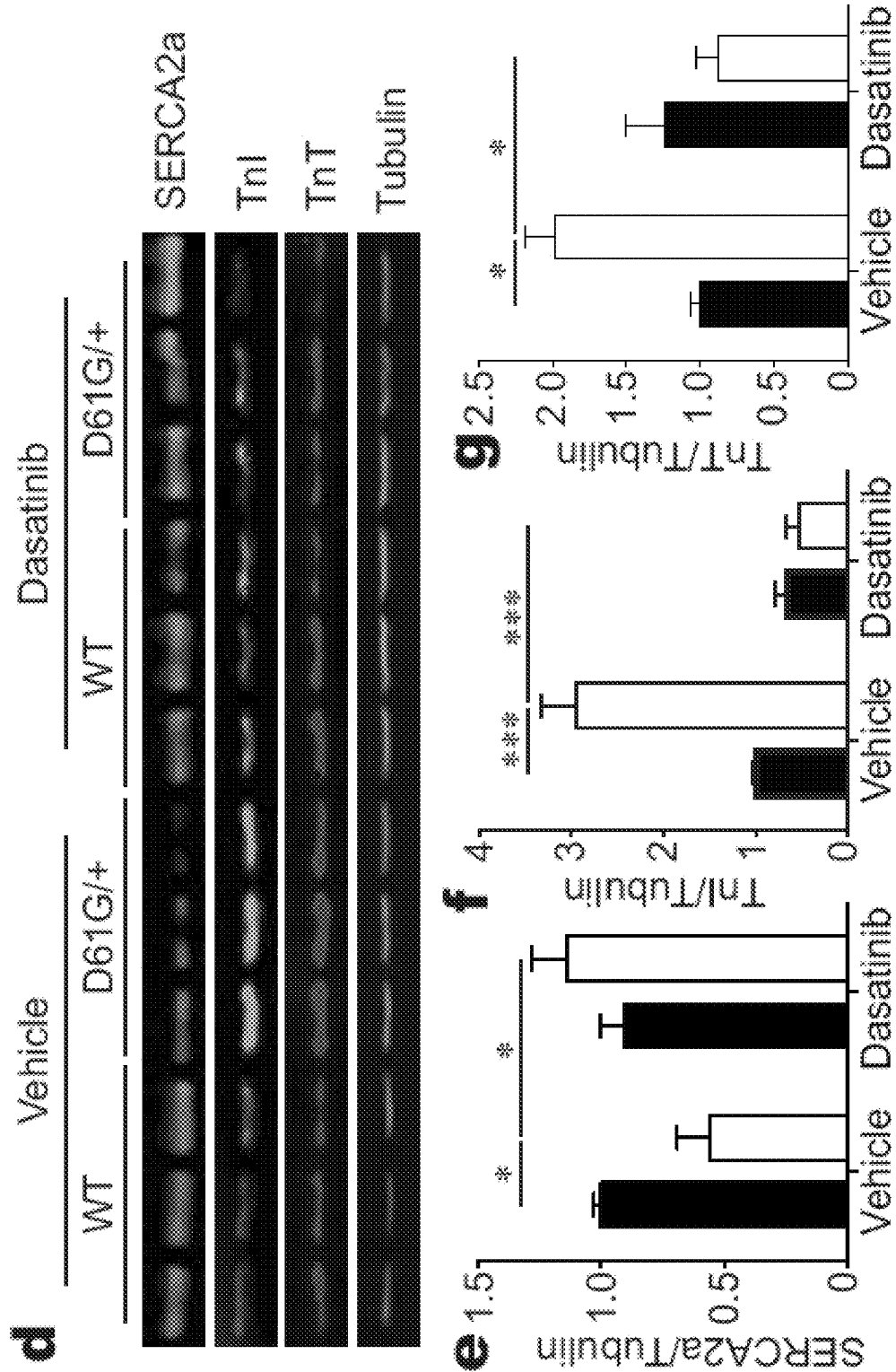

FIG. 16a-FIG. 16g are a panel of images showing cardiomyocytes from dasatinib treated Ptpn11$^{D61G/+}$ mice exhibited normal Ca$^{2+}$ signaling during excitation-contraction coupling. FIG. 16a is an image showing Ca$^{2+}$ excitation-contraction coupling measured in cardiomyocytes isolated from postnatal vehicle- or dasatinib-treated WT and Ptpn11$^{D61G/+}$ mice. Representative traces of cardiomyocyte dynamics for calcium transient traces (top) and their corresponding sarcomere leng shortening traces (bottom). FIG. 16b is a graph showing a summary of the data of relative calcium release ($R_{mag}$ Ca$^{2+}$). FIG. 16c is a graph showing the fraction of sarcomere shortening (n=111~162 cells from 3 mice for each group). FIG. 16d is an image showing heart tissue immunoblotted with anti-SERCA2A, Troponin I (tTnI), Troponin T (tTnT) and Tubulin antibodies. The heart tissue was isolated from postnatal vehicle- or dasatinib-treated WT and Ptpn11$^{D61G/+}$ mice and tissue lysates were immunoblotted. FIG. 16e is a graph showing SERCA2A expression. FIG. 16f is a graph showing Troponin I expression. FIG. 16g is a graph showing Troponin T. Expression was statistically assessed after normalization with tubulin (n=6 for each group). All data present mean±SEM *, p<0.05; , p<0.01; *, p<0.001 (Two-way ANOVA test).

Figures 17A, 17B, 17C:
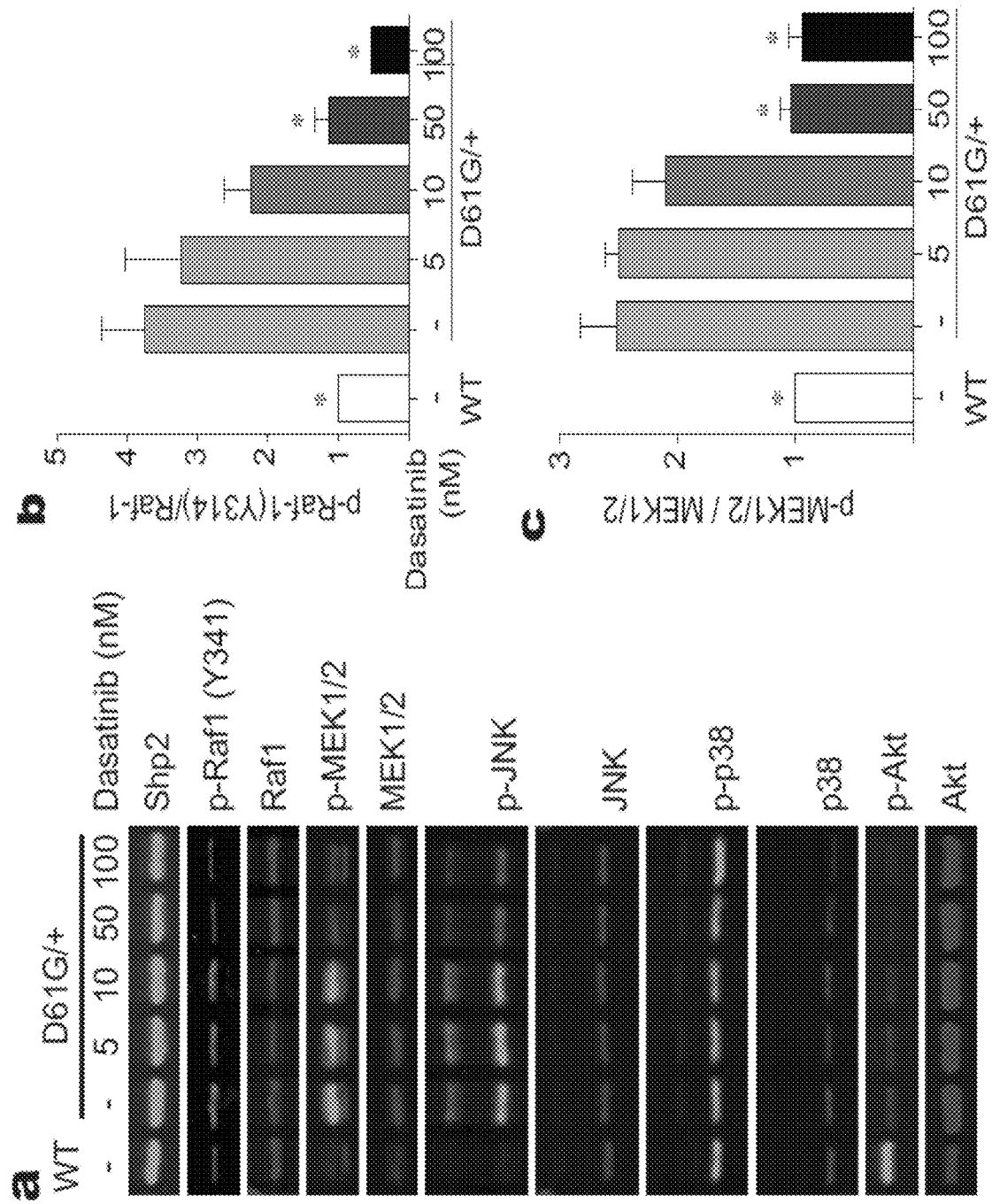
Figures 17D, 17E, 17F, 17G:
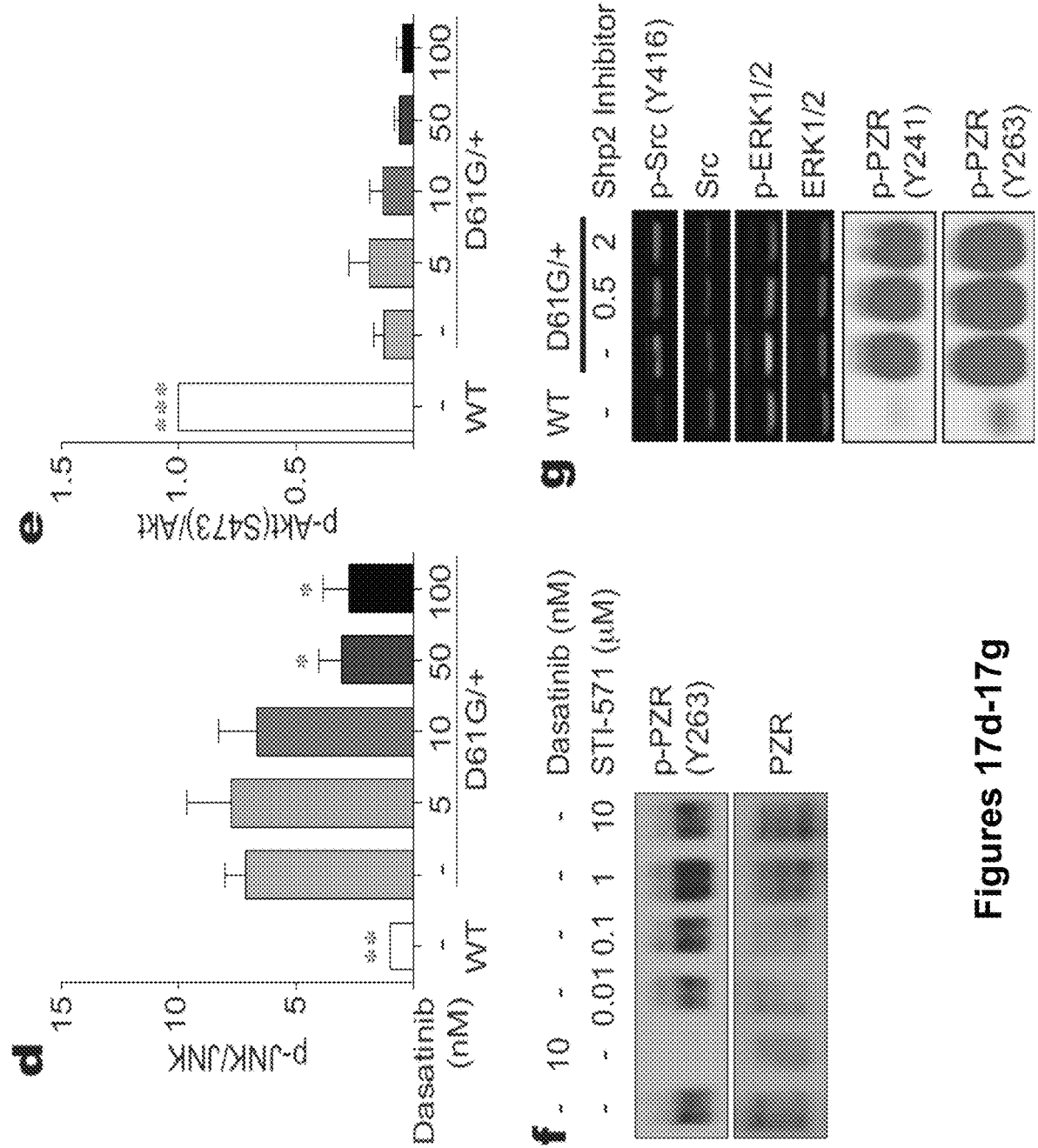

FIGS. 17a-17g are a panel of images showing the effects of Dasatinib on NS signaling in vitro. Mouse embryonic fibroblasts (MEFs) from Ptpn11$^{D61G/+}$ mice were incubated with Dasatinib for 18 hr. Whole cell lysates were immunoblotted with anti-Shp2, p-Src (Y416), Src, p-Raf1 (Y341), Raf1, p-MEK1/2, MEK1/2, p-ERK1/2, ERK1/2, p-JNK, JNK, p-p38, p38, p-Akt and Akt antibodies (FIG. 17a). The phosphorylation levels of Raf1 (Y341) (FIG. 17b), MEK1/2 (FIG. 17c), JNK (FIG. 17d), and Akt (S473) (FIG. 17e) were statistically assessed. All data present mean±SEM. *, p<0.05; , p<0.01; *, p<0.001 denotes significance compared with the vehicle treated Ptpn11$^{D61G/+}$ MEFs (n=3 for each condition; One-way ANOVA test). Mouse embryonic fibroblasts (MEFs) from Ptpn11$^{D61G/+}$ mice were incubated with STI-571 (FIG. 17f) or Shp2 inhibitor (FIG. 17g) for 18 hr. Tyrosyl-phosphorylation of PZR was determined with phospho-specific PZR antibodies.

Figure 18A:
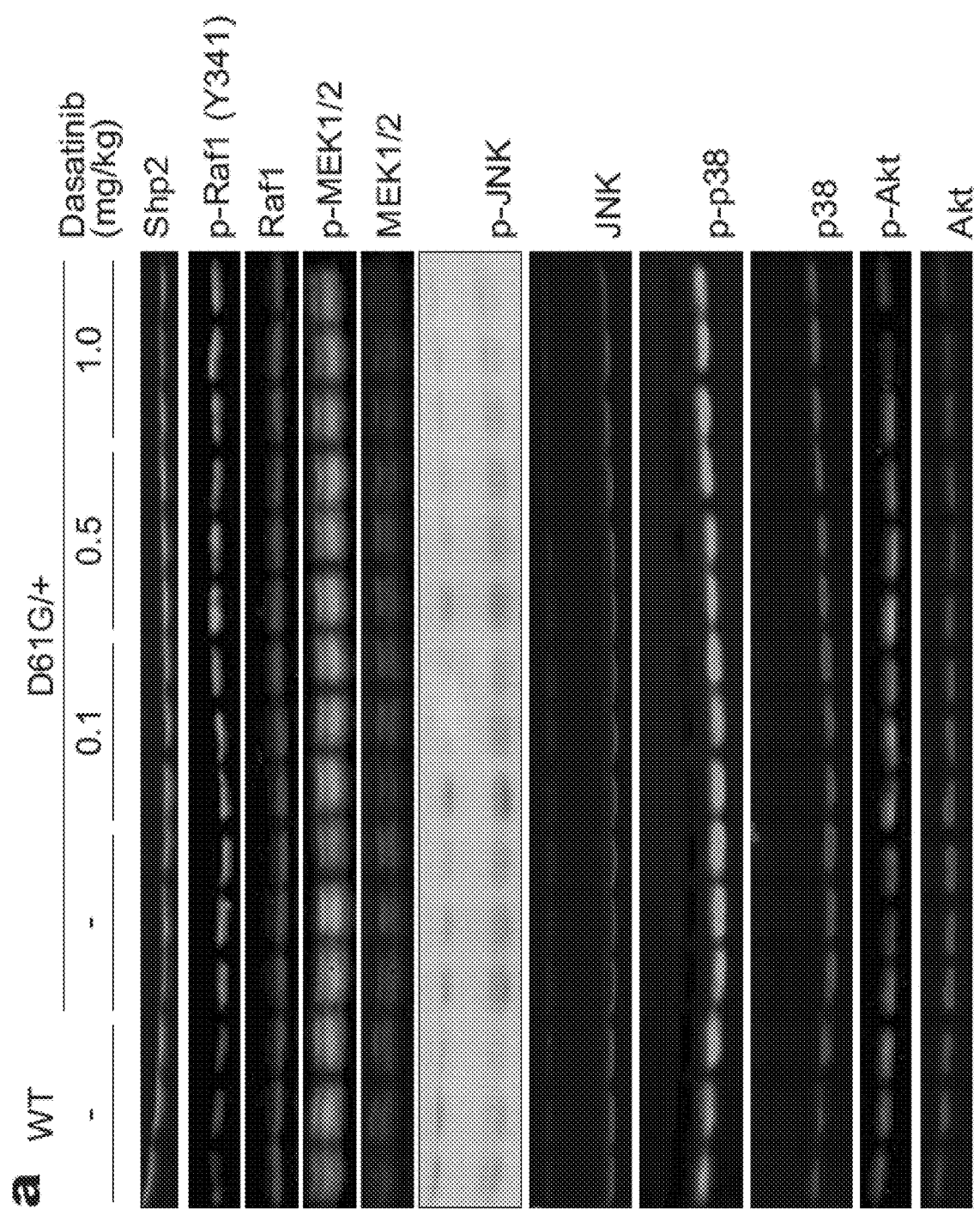
Figures 18B, 18C, 18D, 18E, 18F:
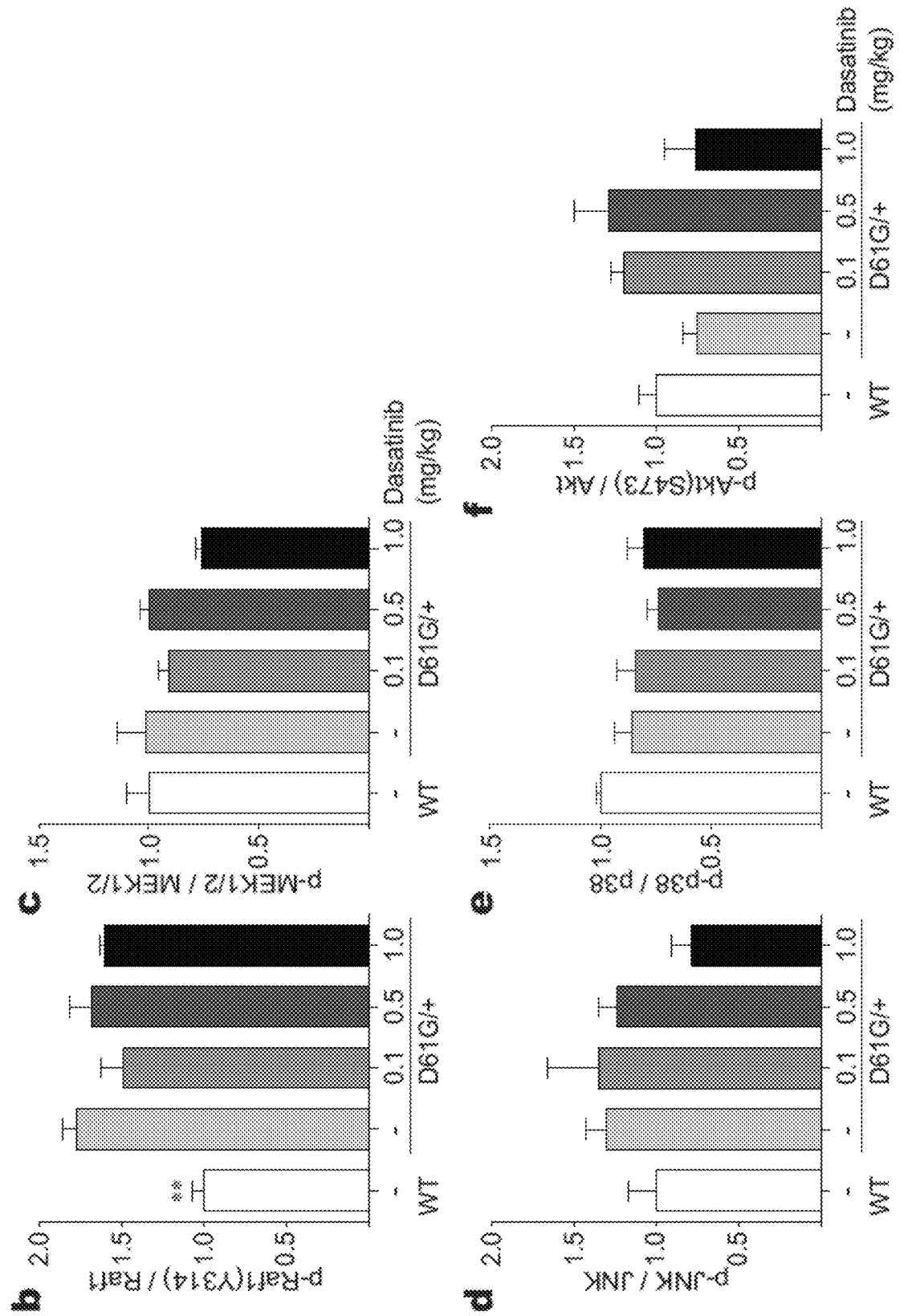

FIGS. 18a-18f are a panel of images showing the effects of dasatinib on NS signaling in vivo. 3-weeks-old WT and Ptpn11$^{D61G/+}$ mice were intraperitoneally injected with vehicle or dasatinib (0.1, 0.5 or 1.0 mg/kg). FIG. 18a is an image showing heart tissue immunoblotted with p-Raf1 (Y341), Raf1, p-MEK1/2, MEK1/2, p-JNK, JNK, p-p38, p38, p-Akt (S473) and Akt antibodies. Heart tissue was isolated after 18 hr and tissue lysates were immunoblotted. FIG. 18b is a graph showing the phosphorylation levels of Raf1 (Y341). FIG. 18c is a graph showing the phosphorylation levels of MEK1/2. FIG. 18d is a graph showing the phosphorylation levels of JNK. FIG. 18e is a graph showing the phosphorylation levels of p38. FIG. 18f is a graph showing the phosphorylation levels of Akt (S473). All data present mean±SEM. *, p<0.05; , p<0.01; *, p<0.001 denotes significance compared with the vehicle treated Ptpn11$^{D61G/+}$ mice (n=3 for each condition; One-way ANOVA test).

Figures 19A, 19B, 19C, 19D, 19E:
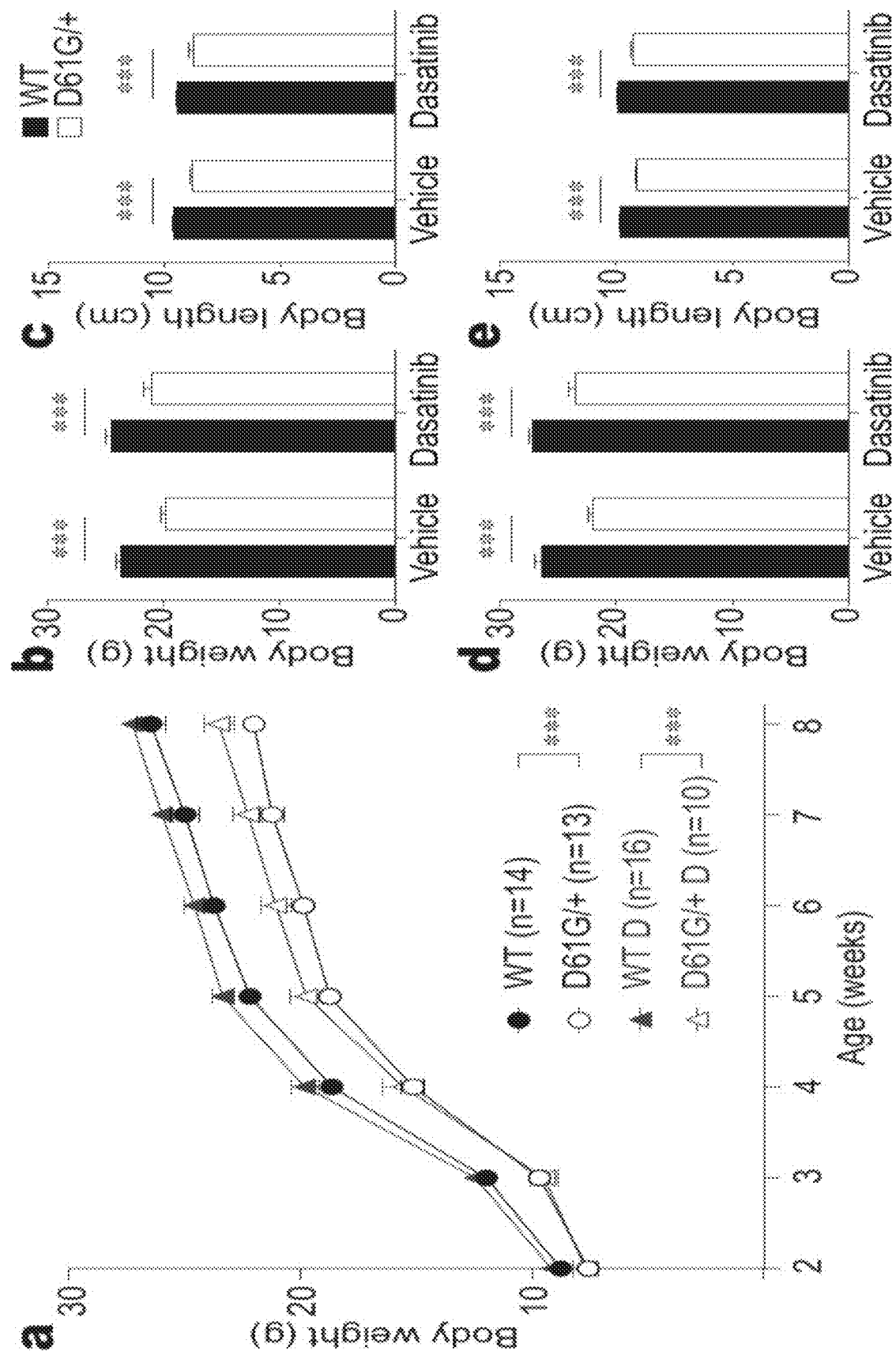

FIGS. 19a-19e are a panel of images showing postnatal dasatinib administration did not improve whole body growth in Ptpn11$^{D61G/+}$ mice. FIG. 19a is a graph showing growth curves of postnatal vehicle- or dasatinib-treated WT and Ptpn11$^{D61G/+}$ mice. Differences within treatment groups were significant (p<0.001, Two-way ANOVA test) from 3-weeks to 8-weeks old. FIG. 19b is a graph showing body weight measured at P42. FIG. 19c is a graph showing body length measured at P42. FIG. 19d is a graph showing body weight measured at P56. FIG. 19c is a graph showing body length measured at P42. FIG. 19e is a graph showing body length measured at P56. All data present mean±SEM. *, p<0.05; , p<0.01; *, p<0.001 (n=10~16 for each group; Two-way ANOVA test).

Figure 20A:
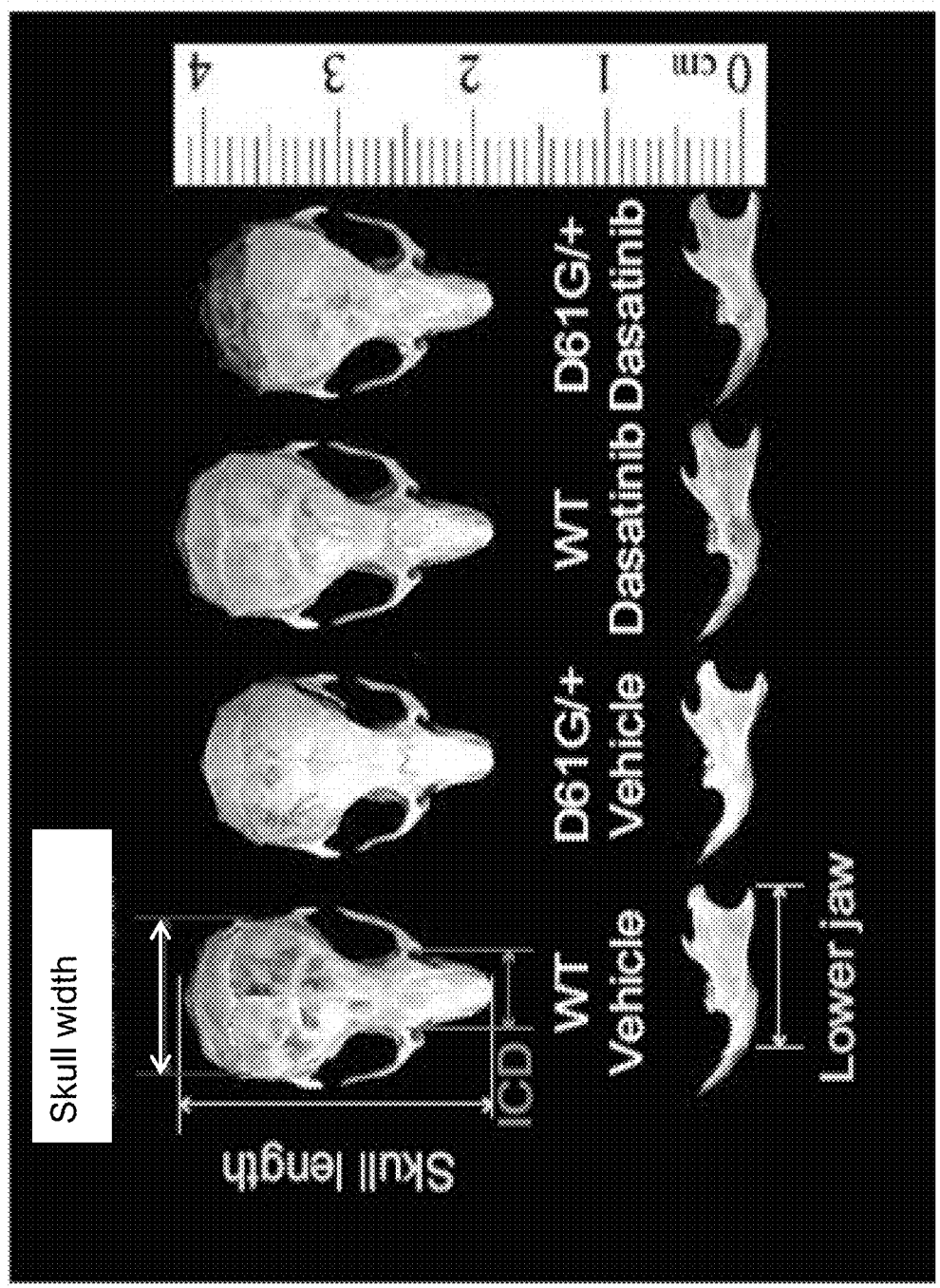
Figures 20B, 20C, 20D, 20E, 20F, 20G, 20H, 20I, 20J, 20K:
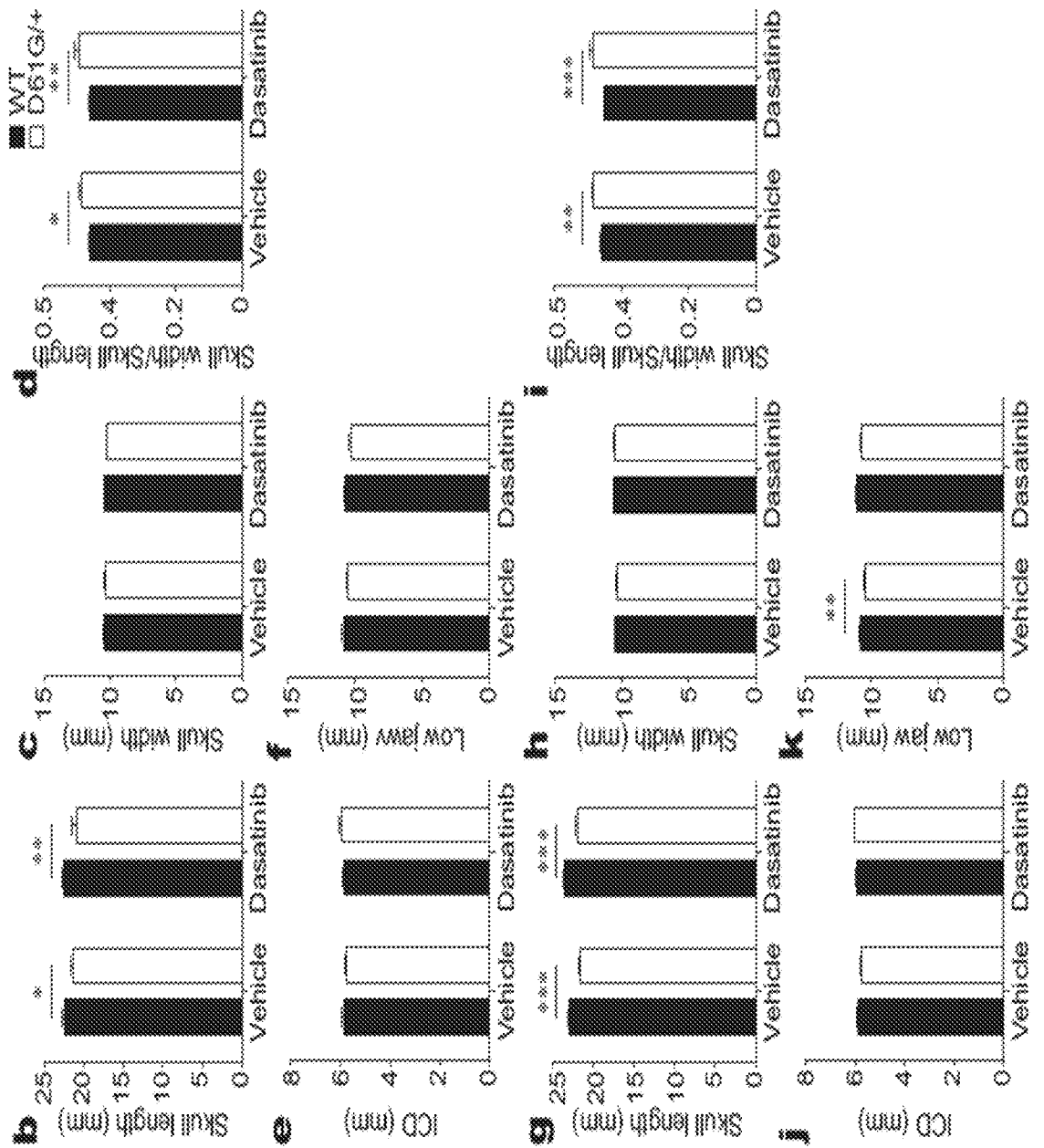

FIGS. 20a-20k are a panel of images showing that the facial dysmorphic features were not changed in dasatinib treated in Ptpn11$^{D61G/+}$ mice. FIG. 20a is a panel of representative images of the skull and the lower jaw from postnatal vehicle- or dasatinib-treated WT and Ptpn11D$^{61G/+}$ mice at P56. FIG. 20b is a graph showing measurements obtained from the skull length from vehicle- or dasatinib-treated WT and Ptpn11D$^{61G/+}$ mice at P42. FIG. 20c is a graph showing measurements obtained from the skull width from vehicle- or dasatinib-treated WT and Ptpn11D$^{61G/+}$ mice at P42. FIG. 20d is a graph showing measurements obtained from the ratio of skull length to skull width from vehicle- or dasatinib-treated WT and Ptpn11D$^{61G/+}$ mice at P42. FIG. 20e is a graph showing measurements obtained from the intercantal distance (ICD) from vehicle- or dasatinib-treated WT and Ptpn11D$^{61G/+}$ mice at P42. FIG. 20f is a graph showing measurements obtained from the lower jaw length from vehicle- or dasatinib-treated WT and Ptpn11D$^{61G/+}$ mice at P42. FIG. 20g is a graph showing measurements obtained from the skull length from vehicle- or dasatinib-treated WT and Ptpn11D$^{61G/+}$ mice at P56. FIG. 20h is a graph showing measurements obtained from the skull width from vehicle- or dasatinib-treated WT and Ptpn11D$^{61G/+}$ mice at P56. FIG. 20i is a graph showing measurements obtained from the ratio of skull length to skull width from vehicle- or dasatinib-treated WT and Ptpn11D$^{61G/+}$ mice at P56. FIG. 20j is a graph showing measurements obtained from the intercantal distance (ICD) from vehicle- or dasatinib-treated WT and Ptpn11D$^{61G/+}$ mice at P56. FIG. 20k is a graph showing measurements obtained from the lower jaw length from vehicle- or dasatinib-treated WT and Ptpn11D$^{61G/+}$ mice at P56. All data present mean±SEM. *, p<0.05; , p<0.01; *, p<0.001. (n=10~16 for each group; Two-way ANOVA test).

Figure 21A:
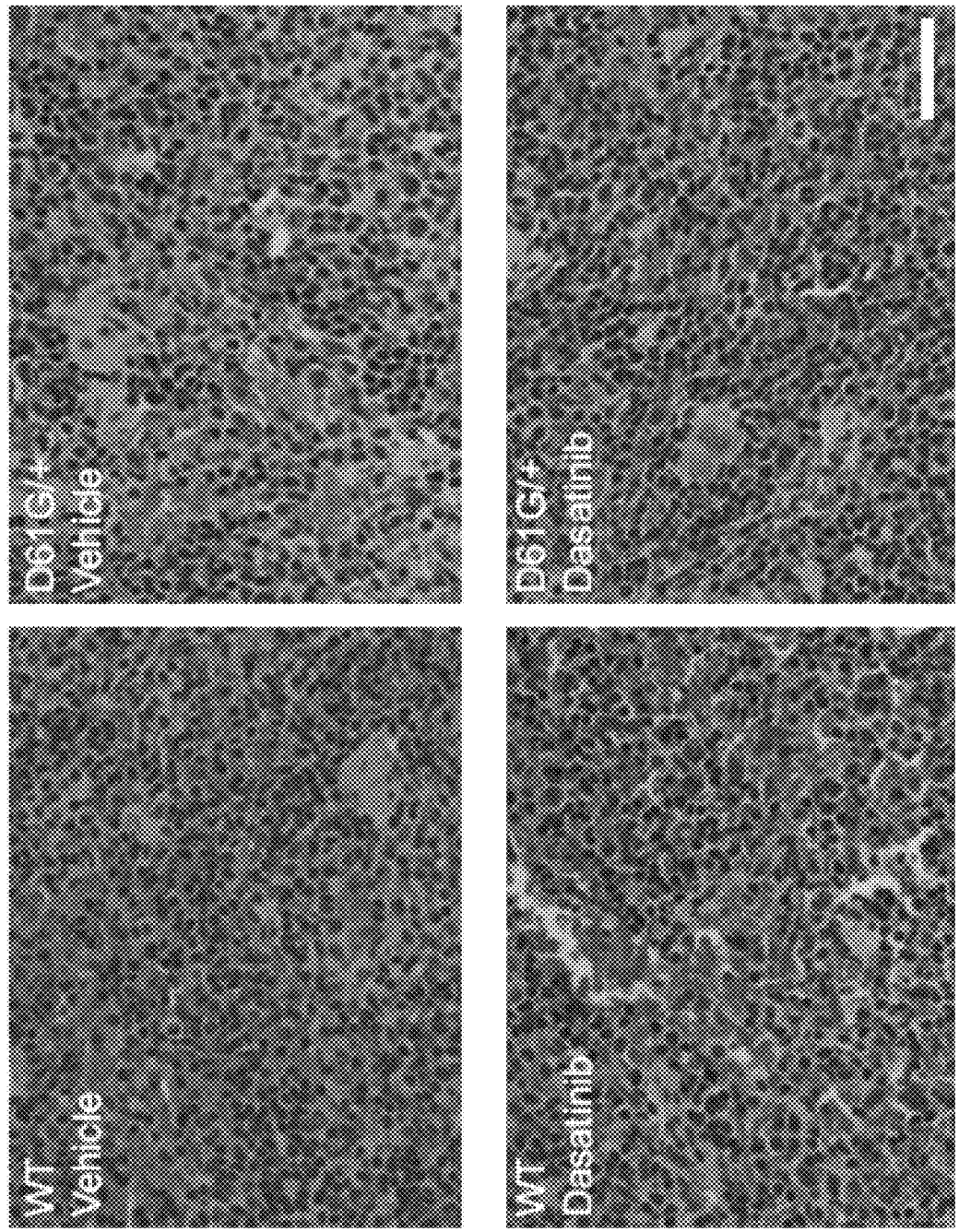
Figures 21B, 21C, 21D, 21E:
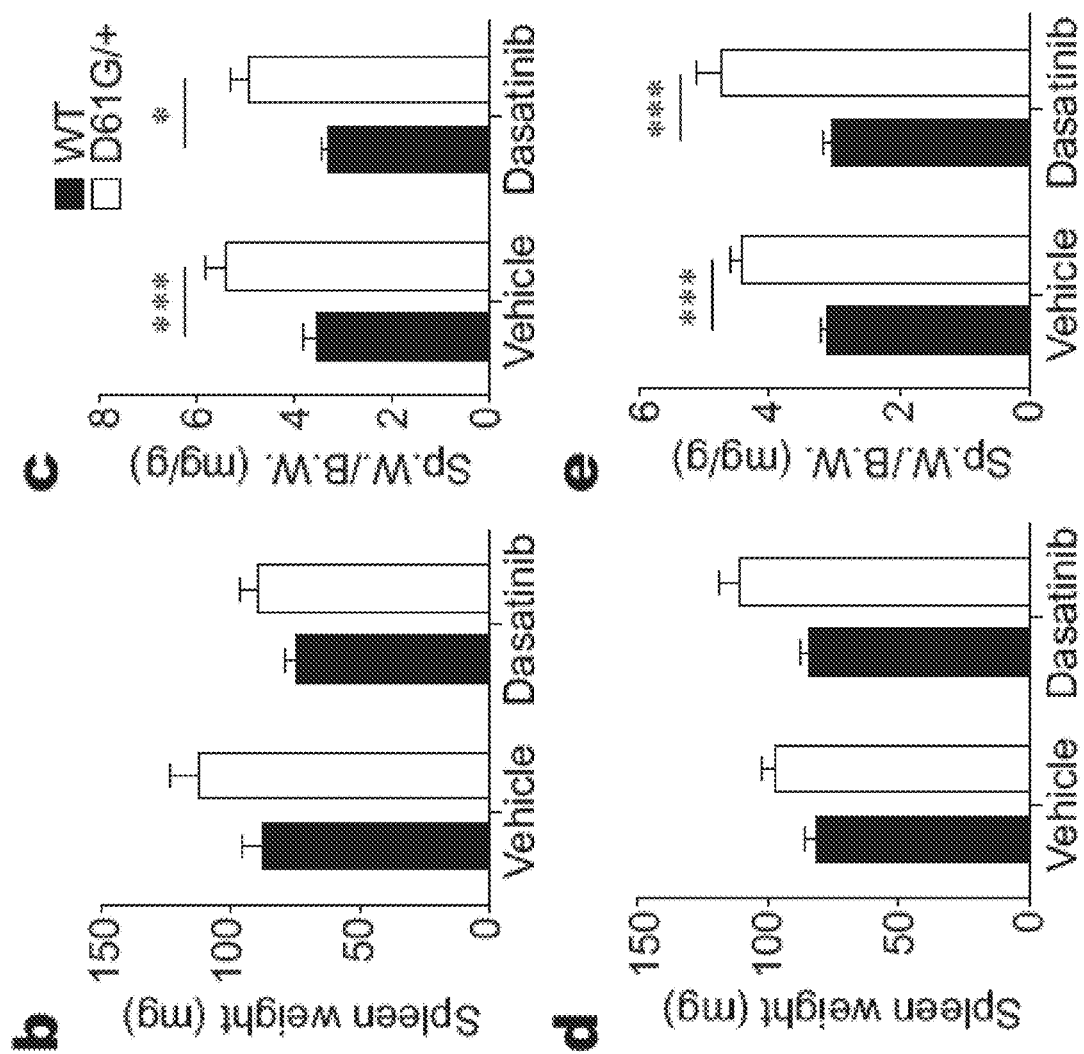

FIGS. 21a-21e are a panel of images showing that postnatal dasatinib treatment did not rescue the splenomegaly phenotype in Ptpn11$^{D61G/+}$ mice. FIG. 21a is a panel of representative H&E stained histological images of the spleen from postnatal vehicle- or dasatinib-treated 8-week-old WT and Ptpn11D$^{61G/+}$ mice at P56 (bar=200 μm). FIG. 21b is a graph showing the spleen weight measured from vehicle- or dasatinib-treated WT and Ptpn11D$^{61G/+}$ mice at P42. FIG. 21c is a graph showing the ratio of spleen weight to body weight measured from vehicle- or dasatinib-treated WT and Ptpn11$^{D61G/+}$ mice at P42. FIG. 21d is a graph showing the spleen weight measured from vehicle- or dasatinib-treated WT and Ptpn11D$^{61G/+}$ mice at P56. FIG. 21e is a graph showing the ratio of spleen weight to body weight measured from vehicle- or dasatinib-treated WT and Ptpn11D$^{61G/+}$ mice at P56. All data represent mean±SEM. *, p<0.05; ***, p<0.001. (n=7~10 for each group; Two-way ANOVA test).

FIGS. 22a-22c are a panel of images showing dasatinib does not induce liver damage. FIG. 22a is a panel of representative H&E stained histological images of the liver from postnatal vehicle- or dasatinib-treated 8-week-old WT and Ptpn11D$^{61G/+}$ mice at P56 (bar=200 μm). FIG. 22b is a graph showing the enzymatic activities of alanine aminotransferase (ALT) in serum measured from vehicle- or dasatinib-treated WT and Ptpn11D$^{61G/+}$ mice at P42. FIG. 22c is a graph showing the enzymatic activities of alanine aminotransferase (ALT) in serum measured from vehicle- or dasatinib-treated WT and Ptpn11D$^{61G/+}$ mice at P56. All data present mean±SEM. *, p<0.05; ***, p<0.001. (n=7~10 for each group; Two-way ANOVA test).

Figure 23:
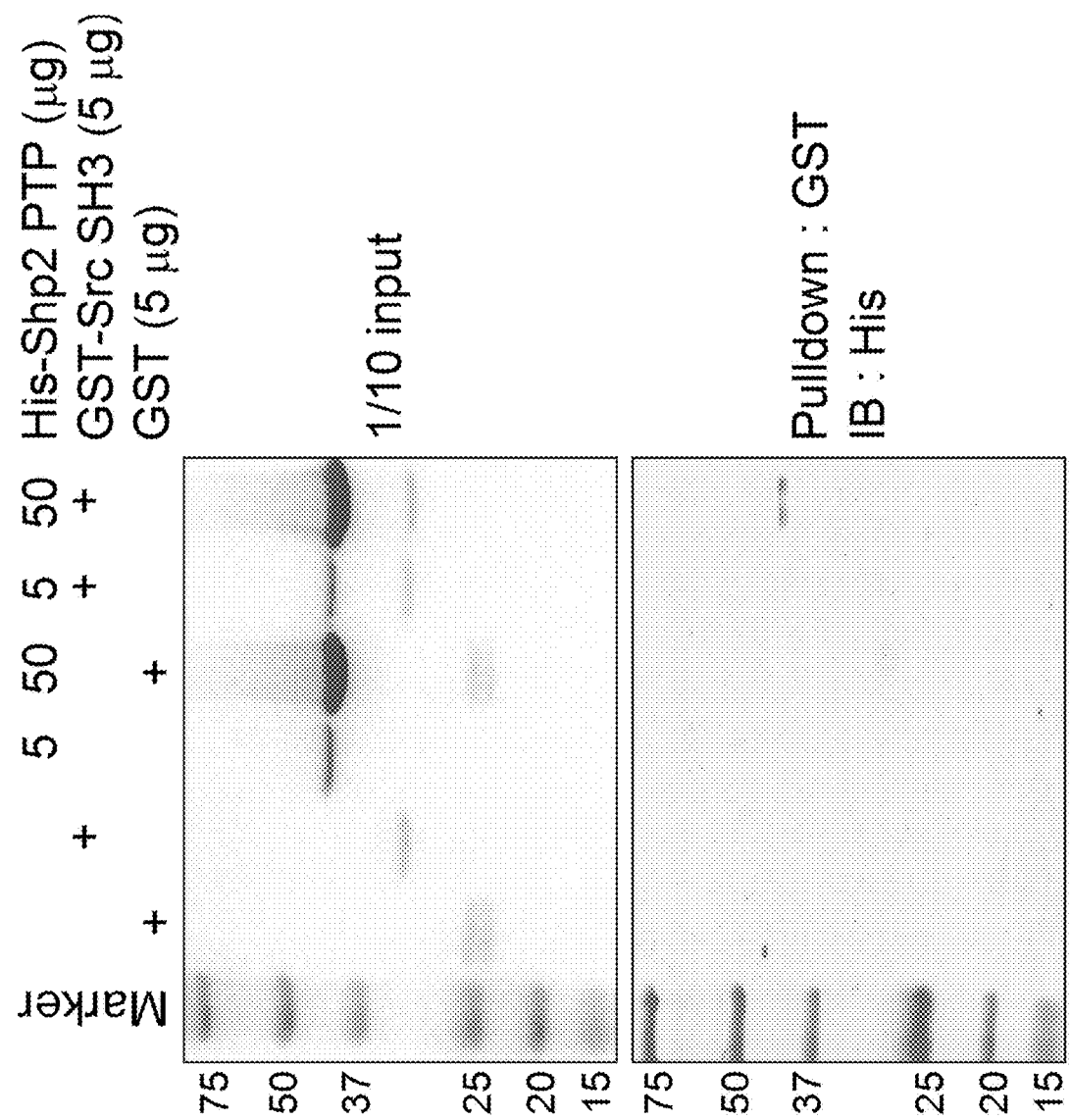

FIG. 23 is an image showing the molecular interaction between SH3 domain of Src and PTP domain of Shp2. Purified GST-tagged SH3 domain of c-Src was incubated with purified His-tagged PTP domain of Shp2 overnight at 4° C. Proteins were immobilized with GST-Sepharose beads and separated by SDS-PAGE. His-PTP domain was detected in GST complexes by immunoblotting with anti-His antibodies.

Figures 24A, 24B:
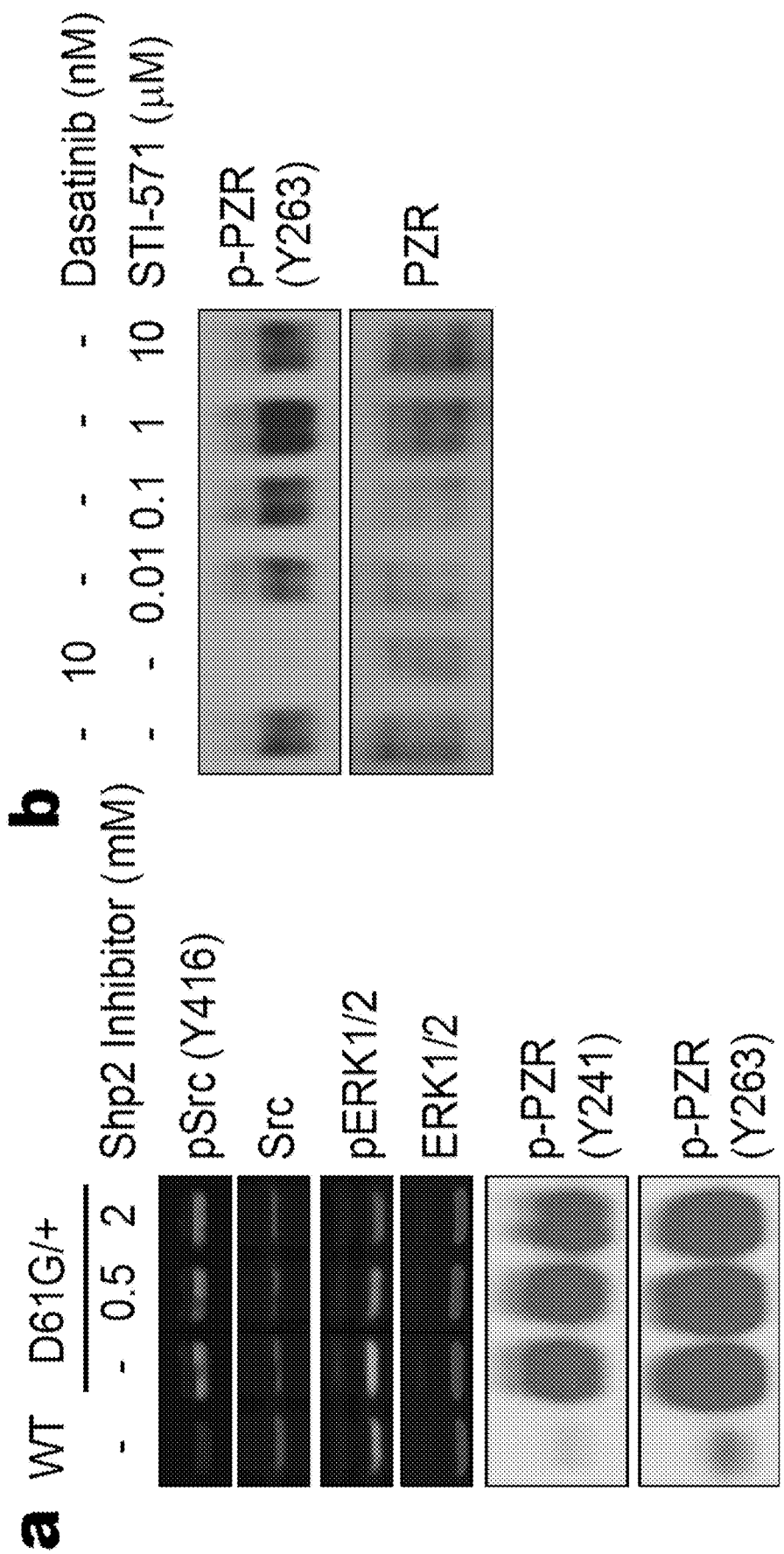

FIGS. 24a-24b are a panel of images showing PZR hyperphosphorylation induced by NS-Shp2 is not dependent on Shp2 phosphatase or c-Abl kinase activities. Mouse embryonic fibroblasts (MEFs) from Ptpn11$^{D61G/+}$ mice were incubated with STI-571 (FIG. 24a) or Shp2 inhibitor (FIG. 24b) for 18 hr. Tyrosyl-phosphorylation of PZR was determined with phospho-specific PZR antibodies.

FIGS. 25a-25f are a panel of graphs showing the improvement in molecular markers of cardiomyopathy and fibrosis in NSML (Y279C/+) mice following dasatinib treatment. Total heart RNA was isolated from postnatal vehicle- or dasatinib-treated (0.1 mg/kg/day) WT and Ptpn11$^{Y279C/+}$ mice (P42). Fibrosis marker genes, Col1a2 (FIG. 25a) and Col3a1 (FIG. 25b), markers of cardiomyopathy ANP (FIG. 25c) and cardiac fetal genes, Myh6 (aMHC) (FIG. 25d), Myh7 (bMHC) (FIG. 25e), and Myh6/Myh7 ratio (FIG. 25f) were measured by quantitative RT-PCR (n=6 for each group). All data represent mean±SEM. *, p<0.05; , p<0.01; *, p<0.001. (Two-way ANOVA test).

DETAILED DESCRIPTION OF THE INVENTION

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

The phrase "aberrant protein tyrosine phosphorylation" refers to hyperphosphorylation or hypophosphorylation of one or more target proteins and/or abnormal protein kinase activity. In one embodiment, the aberrant protein tyrosine phosphorylation is compared to a control.

The term "cardiovascular disease or condition" refers to any disease or condition which affects the cardiovascular system including, but not limited to, nerve conduction disorders, thrombophilia, atherosclerosis, angina pectoris, hypertension, arteriosclerosis, myocardial infarction, congestive heart failure, cardiomyopathy, hypertension, arterial and venous stenosis, valvular disease, myocarditis and arrhythmias. Conditions of cardiovascular disease also include, but are not limited to, any clinical manifestation of a disease state associated with the heart and the central or peripheral arterial and venous vasculature. For example, said clinical manifestations include, but are not limited to pain, weakness, high blood pressure, elevated plasma cholesterol, elevated plasma fatty acids, tachycardia, bradycardia, abnormal electrocardiogram, external or internal bleeding, headache, dizziness, nausea and vomiting.

The term "cardiac function" refers to an activity of the heart or interaction of cells or tissues in the heart to perform an activity. Examples of a cardiac function include, but are not limited to, myofibrilar organization, cardiomyocyte contractility, adequate delivery of blood and nutrients to tissues required. Abnormal cardiac function (inadequate delivery of blood and nutrients to tissues]) can lead to problems, such as but not limited to, blood pressure changes, thrombosis, electrocardiographic changes, arrhythmias, myocarditis, pericarditis, myocardial infarction, cardiomyopathy, hypertrophy, hypotrophy, cardiac failure (ventricular failure (left or right)), congestive heart failure, and cardiac arrest. An improvement of cardiac function may include an improvement, elimination or prevention of at least one abnormal cardiac function, such as but not limited to, myofibrilar disorganization, abnormal cardiomyocyte contractility, cardiac fibrosis, abnormal blood pressure, excess blood pressure changes, thrombosis, electrocardiographic changes, arrhythmias, myocarditis, pericarditis, myocardial infarction, cardiomyopathy, and congestive heart failure.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "congenital heart disease" is meant a category of heart disease that includes abnormalities in cardiovascular structures that occur before birth.

By "effective amount" is meant the amount required to reduce or improve at least one symptom of a disease relative to an untreated patient. The effective amount of an active compound(s) used for therapeutic treatment of a disease varies depending upon the manner of administration, the age, body weight, and general health of the subject.

The term "expression" as used herein is defined as the transcription and/or translation of a particular nucleotide sequence driven by its promoter.

By "fragment" is meant a portion of a polynucleotide or nucleic acid molecule. This portion contains, preferably, at least 10%, 20%, 30%, 40%, 50%, 60%, 70%, 80%, or 90% of the entire length of the reference nucleic acids. A fragment may contain 10, 20, 30, 40, 50, 60, 70, 80, 90, or 100, 200, 300, 400, 500, 600, 700, 800, 900, 1000, 1500, 2000 or 2500 (and any integer value in between) nucleotides. The fragment, as applied to a nucleic acid molecule, refers to a subsequence of a larger nucleic acid. A "fragment" of a nucleic acid molecule may be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

By "low-dosage" is meant a therapeutically effective dosage that is lower than dosages typically prescribed for indications other than heart disease, congenital heart disease, heart failure or similar conditions. In one embodiment, the low-dosage is lower than a chemotherapeutic dosage. In another embodiment, the low-dosage is in the range of about 200-fold lower than a chemotherapeutic dosage of a tyrosine kinase inhibitor. In another embodiment, the low-dosage tyrosine kinase inhibitor improves at least one cardiac function. Dasatinib has been shown to be effective in preventing tumor incidence in mice at a dosage of ~20 mg/kg (Kantarjian, H. et al. Dasatinib versus imatinib in newly diagnosed chronic-phase chronic myeloid leukemia. *N Engl J Med* 362, 2260-2270 (2010)). The therapeutic effects of dasatinib in humans is reported to be ~2 mg/kg, an equivalent dose of ~24 mg/kg in mice (Yu, E. Y. et al. Phase II study of dasatinib in patients with metastatic castration-resistant prostate cancer. *Clinical cancer research: an official journal of the American Association for Cancer Research* 15, 7421-7428 (2009) and Apperley, J. F. et al. Dasatinib in the treatment of chronic myeloid leukemia in accelerated phase after imatinib failure: the START a trial. *J Clin Oncol* 27, 3472-3479, doi:10.1200/JCO.2007.14.3339 (2009)). Doses of dasatinib as low as 0.1 mg/kg (~200-fold lower than therapeutic dose) were sufficient to treat CHD-associated cardiac disease.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

By "Protein Zero-Related" or "PZR," also called "myelin protein zero-like protein 1" or "MPZL1" is meant a protein that is an immunoglobulin superfamily cell surface protein. PZR contains two immunoreceptor tyrosine-based inhibition motifs (ITIMs) responsible for binding to Shp2. When phosphorylated, PZR can specifically bind Shp2, resulting in the activation of the tyrosine phosphatase activity of Shp2. Once activated, the tyrosine phosphatase activity of Shp2 serves to dephosphorylate downstream substrates that propagate cell signals. Shp2 can also signal by acting as a scaffold or an adaptor protein whereby it recruits other molecules/activities to specific complexes. Shp2 can control signaling in both a catalytically-dependent and independent manner.

One isoform of PZR, called PZR1b, lacks the ITIMs and has a dominant negative effect upon full-length PZR and its recruitment of Shp2. An exemplary PZR sequence includes human PZR found at GenBank Accession No. NM_001146191 and NP_001139663, or a fragment thereof, and the mouse PZR sequence found at NM_001001880 or NP_001001880, or a fragment thereof. Much of the information known about PZR relates to its role in adhesion-mediated cell signaling and cell migration. However, whether PZR is involved in pathophysiological cell signaling remains unknown and subsequently the validity of PZR as a target for any human disease has not yet been realized.

By "RASopathy" is meant a group of genetic syndromes caused by germline mutations in genes that encode components or regulators of the Ras/mitogen-activated protein kinase (MAPK) pathway. These syndromes include neurofibromatosis type 1, Noonan syndrome, Noonan syndrome with multiple lentigines, capillary malformation-arteriovenous malformation syndrome, Costello syndrome, cardio-facio-cutaneous syndrome, and Legius syndrome. The Ras/MAPK pathway plays an essential role in regulating the cell cycle and cellular growth, differentiation, and senescence, all of which are critical to normal development. Because of the common underlying Ras/MAPK pathway dysregulation, the RASopathies exhibit numerous overlapping phenotypic features. These overlapping phenotypes can in some cases exist or be caused by mechanisms that operate independently of MAPK itself. The PZR/Shp2 complex described herein lies upstream of Ras.

Noonan syndrome (NS) is an autosomal dominant disorder that occurs with an incidence of about 1:1,000-2,500 live births in the U.S. The cardiac defects most often recognized in NS are pulmonary valve stenosis, atrial-septal defect, and hypertrophic cardiomyopathy, with the severity of each ranging from mild to life-threatening. Noonan syndrome with multiple lentigines (NSML) is a rare autosomal dominant disorder with a similar phenotype to NS, including a "Noonan-like" appearance as well as multiple lentigines, electroconduction abnormalities, ocular hypertelorism, pulmonary valve stenosis, abnormal genitalia, retardation of growth, and deafness. NS-associated mutations result in increased phosphatase activity. NSML-associated mutations result in decreased phosphatase activity.

By "reference" is meant a standard or control. A "reference" is a defined standard or control used as a basis for comparison.

As used herein, "sample" or "biological sample" refers to anything, which may contain the cells of interest (e.g., cancer or tumor cells thereof) for which the screening method or treatment is desired. The sample may be a biological sample, such as a biological fluid or a biological tissue. In one embodiment, a biological sample is a tissue sample including pulmonary arterial endothelial cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

The "Src family of tyrosine kinases" or "SFKs" are a family of enzymes that catalyze the addition of phosphate groups on to tyrosine residues of protein substrates. c-Src represents one member of the SFK family.

By "Src family tyrosine kinase inhibitor" is meant a molecule that decreases or prevents phosphorylation of tyrosine residues on Src family protein substrates. The Src family tyrosine kinase inhibitor can disrupt tyrosyl phosphorylation, bind the tyrosine kinase or tyrosine residue, possibly with higher association efficiency than the tyrosine kinase or phosphate group, and/or prevent effective binding of the phosphate group to the tyrosine residue to decrease or prevent phosphorylation. Src family tyrosine kinase inhibitors include, but are not limited to, small molecule Src family tyrosine kinase inhibitors, Src family tyrosine kinase antagonists, neutralizing antibodies, and inhibitory peptides and/or oligonucleotides. Examples of small molecule Src family tyrosine kinase inhibitors include but are not limited to A419259, AP23451, AP23464, AP23485, AP23588, AZD0424, AZM475271, BMS354825, CGP77675, CU201, ENMD 2076, KB SRC 4, KX2361, KX2-391, MLR 1023, MNS, PCI-32765, PD166285, PD180970, PKC-412, PKI166, PP1, PP2, SRN 004, SU6656, TC-S7003, TG100435, TG100948, TX-1123, VAL 201, WH-4-023, XL 228, altenusin, bosutinib, damnacanthal, dasatinib, herbimycin A, indirubin, neratinib, lavendustin A, pelitinib, piceatannol, saracatinib, SrcI1, and analogs thereof.

"Src homology 2 (SH2) domain-containing (SH2) protein tyrosine phosphatase-2" or "Shp2" is a member of the tyrosine-specific family of protein tyrosine phosphatases (PTPs). Shp2 is a tyrosine phosphatase that catalyzes the tyrosine dephosphorylation of proteins. Mutations in the human gene, PTPN11, have been found to cause about half of Noonan syndrome cases and about one tenth of NSML cases.

A "subject" or "patient," as used therein, may be a human or non-human mammal. Non-human mammals include, for example, livestock and pets, such as ovine, bovine, porcine, canine, feline and murine mammals. Preferably, the subject is human.

The term "transmembrane glycoprotein" refers to a membrane protein that spans the cell membrane. In one embodiment, the transmembrane glycoprotein includes immunoglobulin superfamily cell surface proteins, such as PZR.

As used herein, the terms "treat," "treating," "treatment," and the like refer to reducing or improving a disorder and/or symptom associated therewith. It will be appreciated that, although not precluded, treating a disorder or condition does not require that the disorder, condition or symptoms associated therewith be completely ameliorated or eliminated.

By "tyrosine kinase inhibitor" is meant a molecule that decreases or prevents phosphorylation of tyrosine residues on protein substrates. The tyrosine kinase inhibitor can disrupt tyrosyl phosphorylation, bind the tyrosine kinase or tyrosine residue, possibly with higher association efficiency than the tyrosine kinase or phosphate group, and/or prevent effective binding of the phosphate group to the tyrosine residue to decrease or prevent phosphorylation. Tyrosine kinase inhibitors include, but are not limited to, small molecule tyrosine kinase inhibitors, tyrosine kinase antagonists, neutralizing antibodies, and inhibitory peptides and/or oligonucleotides. Examples of small molecule tyrosine kinase inhibitors include but are not limited to afatinib, axitinib, bosutinib, cabozantinib, cediranib, ceritinib, crizotinib, dabrafenib, dasatinib, erlotinib, everolimus, gefitinib, ibrutinib, imatinib, lapatinib, lenvatinib, lestaurtinib, nilotinib, nintedanib, palbociclib, pazopanib, ponatinib, regorafenib, ruxolitinib, semananib, sirolimus, sorafenib, sunitinib, temsirolimus, tofacitinib, trametinib, vandetanib, and vemurafenib.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Compositions

It has been discovered that aberrant protein tyrosine phosphorylation, such as phosphorylation of Src family tyrosine kinases and their substrates, is altered in subjects with cardiovascular disease. It has also been discovered that aberrant protein tyrosine phosphorylation is altered in subject with certain diseases, such as RASopathies. Inhibition of tyrosine kinase activity treats heart disease and improves at least one cardiac function. Inhibition also improves cardiovascular function in subjects with congenital heart defects associated with a RASopathy. The invention includes compositions that inhibit tyrosine kinases, such as Src family tyrosine kinases, to improve at least one cardiac function, thereby preventing or decreasing tyrosine phosphorylation. The invention includes, in one aspect, a composition comprising a low-dosage tyrosine kinase inhibitor, wherein the low-dosage tyrosine kinase inhibitor decreases tyrosine phosphorylation and improves at least one cardiac function in a subject in need thereof.

In one embodiment, the low-dosage tyrosine kinase inhibitor decreases aberrant tyrosine phosphorylation of a transmembrane glycoprotein, such as a Src family tyrosine kinase and Protein Zero-Related (PZR).

In one embodiment, the amount of the low-dosage tyrosine kinase inhibitor is in the range of about 25 fold to about 500 fold lower than a chemotherapeutic dosage of the tyrosine kinase inhibitor. In another embodiment, the amount of the low-dosage tyrosine kinase inhibitor is in the range of about 25 fold to about 400 fold lower than a chemotherapeutic dosage of the tyrosine kinase inhibitor. In another embodiment, the amount of the low-dosage tyrosine kinase inhibitor is in the range of about 25 fold to about 300 fold lower than a chemotherapeutic dosage of the tyrosine kinase inhibitor. In another embodiment, the amount of the low-dosage tyrosine kinase inhibitor is in the range of about 35 fold to about 300 fold lower than a chemotherapeutic dosage of the tyrosine kinase inhibitor. In another embodiment, the amount of the low-dosage tyrosine kinase inhibitor is in the range of about 50 fold to about 300 fold lower than a chemotherapeutic dosage of the tyrosine kinase inhibitor. In another embodiment, the amount of the low-dosage tyrosine kinase inhibitor is in the range of about 100 fold to about 300 fold lower than a chemotherapeutic dosage of the tyrosine kinase inhibitor. In another embodiment, the amount of the low-dosage tyrosine kinase inhibitor is in the range of about 150 fold to about 250 fold lower than a chemotherapeutic dosage of the tyrosine kinase inhibitor. In another embodiment, the amount of the low-dosage tyrosine kinase inhibitor is in the range of about 175 fold to about 250 fold lower than a chemotherapeutic dosage of the tyrosine kinase inhibitor. The low-dosage tyrosine kinase inhibitor can be about 25 fold, 30 fold, 35 fold, 40 fold, 45 fold, 50 fold, 55 fold, 60 fold, 65 fold, 70 fold, 75 fold, 80 fold, 85 fold, 90 fold, 95 fold, 100 fold, 105 fold, 110 fold, 115 fold, 120 fold, 125 fold, 130 fold, 135 fold, 140 fold, 145 fold, 150 fold, 155 fold, 160 fold, 165 fold, 170 fold, 175 fold, 180 fold, 185 fold, 190 fold, 195 fold, 200 fold, 205 fold, 210 fold, 215 fold, 220 fold, 225 fold, 230 fold, 235 fold, 240 fold, 245 fold, 250 fold, 255 fold, 260 fold, 265 fold, 270 fold, 275 fold, 280 fold, 285 fold, 290 fold, 295 fold, 300 fold, and any fold change therebetween lower than a chemotherapeutic dosage of the tyrosine kinase inhibitor. In some embodiments, the chemotherapeutic dosage of the tyrosine kinase inhibitor is in the range of about 75 to about 170 mg/day or about 1.1 to about 2.4 for a 70 kg adult.

In another embodiment, the low-dosage tyrosine kinase inhibitor is selected from the group consisting of afatinib, axitinib, bosutinib, cabozantinib, cediranib, ceritinib, crizotinib, dabrafenib, dasatinib, erlotinib, everolimus, gefitinib, ibrutinib, imatinib, lapatinib, lenvatinib, lestaurtinib, nilotinib, nintedanib, palbociclib, pazopanib, ponatinib, regorafenib, ruxolitinib, semananib, sirolimus, sorafenib, sunitinib, temsirolimus, tofacitinib, trametinib, vandetanib, and vemurafenib. In another embodiment, the composition comprises more than one of the tyrosine kinase inhibitors disclosed herein.

In still another embodiment, the low-dosage tyrosine kinase inhibitor is a Src family tyrosine kinase inhibitor, such as but not limited to an inhibitor selected from the group consisting A419259, AP23451, AP23464, AP23485, AP23588, AZD0424, AZM475271, BMS354825, CGP77675, CU201, ENMD 2076, KB SRC 4, KX2361, KX2-391, MLR 1023, MNS, PCI-32765, PD166285, PD180970, PKC-412, PKI166, PP1, PP2, SRN 004, SU6656, TC-S7003, TG100435, TG100948, TX-1123, VAL 201, WH-4-023, XL 228, altenusin, bosutinib, damnacanthal, dasatinib, herbimycin A, indirubin, neratinib, lavendustin A, pelitinib, piceatannol, saracatinib, SrcI1, and analogs thereof. In another embodiment, the composition comprises at least one Src family tyrosine kinase inhibitor.

In another embodiment, the low-dosage tyrosine kinase inhibitor improves at least one cardiac function. The cardiac function may include, but is not limited to, myofibrilar organization, cardiomyocyte contractility, SERCA2A expression, and cardiac fibrosis. Abnormal cardiac function can lead to problems, such as but not limited to, blood pressure changes, thrombosis, electrocardiographic changes, arrhythmias, myocarditis, pericarditis, myocardial infarction, cardiomyopathy, cardiac failure (ventricular failure), congestive heart failure, and cardiac arrest. An improvement of cardiac function may include an improvement, elimination or prevention of at least one abnormal cardiac function, such as but not limited to, myofibrilar disorganization, abnormal cardiomyocyte contractility, dysregulated SERCA2A expression, cardiac fibrosis, abnormal blood pressure, excess blood pressure changes, thrombosis, electrocardiographic changes, arrhythmias, myocarditis, pericarditis, myocardial infarction, cardiomyopathy, and congestive heart failure.

In yet another embodiment, the low-dosage tyrosine kinase inhibitor provides an anti-fibrotic effect. Increased levels of fibrotic components in the myocardium has been associated with the progression of heart failure. Tyrosine kinase inhibition at a low-dosage reduces the accumulation of fibrotic components in the myocardium.

Compositions that decrease aberrant protein tyrosine phosphorylation are also included in the invention. Certain diseases, such as cardiovascular disease or conditions like congenital heart disease, are characterized by aberrant protein tyrosine phosphorylation. Treatments that prevent or decrease tyrosine phosphorylation of one or more transmembrane glycoproteins, such as protein zero-related or PZR, are therefore included in the invention. In another aspect, the invention includes a composition that is capable of decreasing aberrant protein tyrosine phosphorylation associated with cardiovascular disease or condition. In yet another aspect, the invention includes a composition that is capable of decreasing aberrant protein tyrosine phosphorylation associated with congenital heart disease. In still another aspect, the invention includes a composition that is capable of decreasing aberrant protein tyrosine phosphorylation associated with cardiovascular disease or condition associated with a RASopathy.

Methods

The present invention also includes a method for preventing or treating a cardiovascular disease or condition in a subject in need thereof. As described herein, inhibition of aberrant tyrosine phosphorylation prevents and/or treats the cardiovascular disease or condition. Administering a composition that includes a low-dosage of a tyrosine kinase inhibitor to a subject, such as a pediatric subject, in need thereof to decrease aberrant levels of tyrosine phosphorylation for preventing or treating cardiovascular disease or condition.

In one aspect, the invention includes a method of treating cardiovascular disease or condition having aberrant protein tyrosine phosphorylation in a subject, comprising administering a low-dosage of a tyrosine kinase inhibitor to a subject in need thereof, wherein the tyrosine kinase inhibitor decreases aberrant levels of tyrosine phosphorylation and improves at least one cardiac function in the subject.

In another aspect, the invention includes a method of treating congenital heart disease comprising administering a low-dosage of a tyrosine kinase inhibitor to a subject in need thereof, wherein the tyrosine kinase inhibitor decreases aberrant levels of tyrosine phosphorylation and improves at least one cardiac function in the subject.

In yet another aspect, the invention includes a method of treating cardiovascular disease or condition associated with a RASopathy having aberrant protein tyrosine phosphorylation comprising administering a low-dosage of a tyrosine kinase inhibitor to a subject in need thereof, wherein the tyrosine kinase inhibitor decreases aberrant levels of Protein Zero-Related (PZR) tyrosyl phosphorylation and improves at least one cardiac function in the subject.

In one embodiment, the cardiovascular disease or condition in the method described herein is congenital heart disease or a cardiovascular disease or condition associated with a RASopathy, such as but not limited to a RASopathy selected from the group consisting of Neurofibromatosis Type 1, Noonan syndrome, Noonan syndrome with multiple lentigines (Leopard syndrome), capillary malformation-arteriovenous malformation syndrome, Costello syndrome, cardio-facio-cutaneous syndrome, and Legius syndrome.

In another embodiment, the method includes administering the tyrosine kinase inhibitor to a subject that is a pediatric patient. The pediatric subject can be less than 18 years of age. The pediatric subject can be less than 12 years of age. The pediatric subject can be less than 10, 9, 8, 7, 6, 5, 4, 3, 2, and 1 years of age. In another embodiment, the subject is a pediatric patient that is less than 12 years of age. In an alternative embodiment, the method includes administering the tyrosine kinase inhibitor to a subject that is greater than 18 years of age.

In one embodiment, the method includes administering a low-dosage tyrosine kinase inhibitor that decreases aberrant tyrosine phosphorylation of a transmembrane glycoprotein, such as a Src family tyrosine kinase and Protein Zero-Related (PZR). In one embodiment, the aberrant levels of tyrosine phosphorylation comprise aberrant levels of tyrosine phosphorylated Protein Zero-Related (PZR).

In another embodiment, administering the low-dosage tyrosine kinase inhibitor improves a cardiac function, such as but not limited to, myofibrilar organization, cardiomyocyte contractility, SERCA2A expression, and cardiac fibrosis. In another embodiment, an improvement of a cardiac function may include an improvement, elimination or prevention of at least one abnormal cardiac function, such as but not limited to, myofibrilar disorganization, abnormal cardiomyocyte contractility, dysregulated SERCA2A expression, cardiac fibrosis, abnormal blood pressure, excess blood pressure changes, thrombosis, electrocardiographic changes, arrhythmias, myocarditis, pericarditis, myocardial infarction, cardiomyopathy, and congestive heart failure. In yet another embodiment, administering the low-dosage tyrosine kinase inhibitor provides an anti-fibrotic effect to the subject.

In one embodiment, the dose of the low-dosage tyrosine kinase inhibitor used in the method described herein is in the range of about 25 fold to about 500 fold lower than a chemotherapeutic dosage of the tyrosine kinase inhibitor. In another embodiment, the amount of the low-dosage tyrosine kinase inhibitor is in the range of about 25 fold to about 400 fold lower than a chemotherapeutic dosage of the tyrosine kinase inhibitor. In another embodiment, the amount of the low-dosage tyrosine kinase inhibitor is in the range of about 25 fold to about 300 fold lower than a chemotherapeutic dosage of the tyrosine kinase inhibitor. In another embodiment, the amount of the low-dosage tyrosine kinase inhibitor is in the range of about 35 fold to about 300 fold lower than a chemotherapeutic dosage of the tyrosine kinase inhibitor. In another embodiment, the amount of the low-dosage tyrosine kinase inhibitor is in the range of about 50 fold to about 300 fold lower than a chemotherapeutic dosage of the tyrosine kinase inhibitor. In another embodiment, the amount of the low-dosage tyrosine kinase inhibitor is in the range of about 100 fold to about 300 fold lower than a chemotherapeutic dosage of the tyrosine kinase inhibitor. In another embodiment, the amount of the low-dosage tyrosine kinase inhibitor is in the range of about 150 fold to about 250 fold lower than a chemotherapeutic dosage of the tyrosine kinase inhibitor. In another embodiment, the amount of the low-dosage tyrosine kinase inhibitor is in the range of about 175 fold to about 250 fold lower than a chemotherapeutic dosage of the tyrosine kinase inhibitor. The low-dosage tyrosine kinase inhibitor can be about 25 fold, 30 fold, 35 fold, 40 fold, 45 fold, 50 fold, 55 fold, 60 fold, 65 fold, 70 fold, 75 fold, 80 fold, 85 fold, 90 fold, 95 fold, 100 fold, 105 fold, 110 fold, 115 fold, 120 fold, 125 fold, 130 fold, 135 fold, 140 fold, 145 fold, 150 fold, 155 fold, 160 fold, 165 fold, 170 fold, 175 fold, 180 fold, 185 fold, 190 fold, 195 fold, 200 fold, 205 fold, 210 fold, 215 fold, 220 fold, 225 fold, 230 fold, 235 fold, 240 fold, 245 fold, 250 fold, 255 fold, 260 fold, 265 fold, 270 fold, 275 fold, 280 fold, 285 fold, 290 fold, 295 fold, 300 fold, and any fold change therebetween lower than a chemotherapeutic dosage of the tyrosine kinase inhibitor. In some embodiments, the chemotherapeutic dosage of the tyrosine kinase inhibitor is in the range of about 75 to about 170 mg/day or about 1.1 to about 2.4 for a 70 kg adult.

In yet another embodiment, the low-dosage tyrosine kinase inhibitor is selected from the group consisting of afatinib, axitinib, bosutinib, cabozantinib, cediranib, ceritinib, crizotinib, dabrafenib, dasatinib, erlotinib, everolimus, gefitinib, ibrutinib, imatinib, lapatinib, lenvatinib, lestaurtinib, nilotinib, nintedanib, palbociclib, pazopanib, ponatinib, regorafenib, ruxolitinib, semananib, sirolimus, sorafenib, sunitinib, temsirolimus, tofacitinib, trametinib, vandetanib, and vemurafenib. In another embodiment, the tyrosine kinase inhibitor is a Src family tyrosine kinase inhibitor, such as but not limited to, A419259, AP23451, AP23464, AP23485, AP23588, AZD0424, AZM475271, BMS354825, CGP77675, CU201, ENMD 2076, KB SRC 4, KX2361, KX2-391, MLR 1023, MNS, PCI-32765, PD166285, PD180970, PKC-412, PKI166, PP1, PP2, SRN 004, SU6656, TC-S7003, TG100435, TG100948, TX-1123, VAL 201, WH-4-023, XL 228, altenusin, bosutinib, damnacanthal, dasatinib, herbimycin A, indirubin, neratinib, lavendustin A, pelitinib, piceatannol, saracatinib, SrcI1, and analogs thereof. In another embodiment, the composition comprises more than one of the tyrosine kinase inhibitors disclosed herein. In yet another embodiment, the composition comprises at least one Src family tyrosine kinase inhibitor. In such embodiments, the tyrosine kinase inhibitors may be administered together or sequentially, by different administration routes, or in the same or different pharmaceutical composition.

The methods and composition disclosed herein are also useful as a treatment for a cardiovascular disease or condition in a subject having a cardiovascular disease or condition characterized by aberrant protein tyrosine phosphorylation.

Pharmaceutical Compositions

The invention also encompasses the use of a pharmaceutical composition of the invention to practice the methods of the invention. In one aspect, the invention includes a pharmaceutical composition comprising the composition as described herein and a pharmaceutically acceptable carrier. In another aspect, the composition described herein is used in the manufacture of a medicament for the treatment of a cardiovascular disease or condition in a subject in need thereof. In yet another aspect, the invention includes a pharmaceutical composition comprising the composition as described herein in combination with another therapeutic agent used in the treatment of a cardiovascular disease or condition. Such pharmaceutical compositions may be provided in a form suitable for administration to a subject, and may comprise one or more pharmaceutically acceptable carriers, one or more additional ingredients, or some combination of these. The composition described herein may comprise a physiologically acceptable salt, such as a compound contemplated within the invention in combination with a physiologically acceptable cation or anion, as is well known in the art.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment, the compositions of the invention are formulated using one or more pharmaceutically acceptable excipients or carriers. In one embodiment, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out embodiments of the present invention, and are not to be construed as limiting in any way.

Noonan syndrome (NS) is an autosomal dominant disorder caused by activating mutations in the PTPN11 gene encoding Shp2, which manifests in congenital heart disease, short stature, and facial dysmorphia. The complexity of Shp2 signaling is exemplified by the observation that Noonans syndrome with multiple lentigines (NSML) patients possess inactivating PTPN11 mutations yet exhibit similar symptoms to NS. "Protein zero-related" (PZR), a transmembrane glycoprotein that interfaces with the extracellular matrix to promote cell migration, was identified as a major hyper-tyrosyl-phosphorylated protein in mouse models of NS and NSML. PZR hyper-tyrosyl phosphorylation was facilitated in a phosphatase-independent manner by enhanced Src recruitment to NS and NSML Shp2. Hence, PZR was identified as an NS and NSML target. Enhanced PZR-mediated membrane recruitment of Shp2 served as a common mechanism to direct overlapping pathophysiological characteristics of these PTPN11 mutations.

The Materials and Methods used in the performance of the experiments disclosed herein are now described.

Antibodies, Chemicals, Cell Lines, and Expression Reagents.

Rabbit monoclonal phospho-PZR (Y241) and rabbit monoclonal phospho-PZR (Y263) antibodies were generated in collaboration with Cell Signaling. Mouse monoclonal Src antibody, rabbit polyclonal Src antibody, rabbit polyclonal phospho-ERK1/2 (T202 Y204), mouse monoclonal ERK1/2 antibody, rabbit polyclonal phospho-Akt (S473) antibodies and mouse monoclonal Akt antibodies were purchased from Cell Signaling. Rabbit polyclonal Shp2 antibodies and rabbit polyclonal ERK1/2 antibody were purchased from Santa Cruz Biotechnology. Mouse monoclonal Shp2 antibody was purchased from BD Bioscience. Mouse antiphosphotyrosine antibody 4G10 (05-321) was from Merck Millipore, rabbit anti-GFP (TP401) was from Acris, and mouse anti-HA. 11 clone 16B12 was from Covance. Rabbit polyclonal PZR (105-6) was generously provided by Z. J. Zhao. Src family kinase inhibitors PP2 and SU6656 were purchased from Calbiochem. HEK-293, NIH 3T3, SYF (Src$^{-/-}$ Yes$^{-/-}$ Fyn$^{-/-}$ mouse embryonic fibroblasts [MEFs]), and Src$^{++}$ (Src-overexpressing SYF) cells were purchased from ATCC and grown in growth medium (Dulbecco's modified Eagle's medium [DMEM] supplemented with 1% penicillin-streptomycin and 10% fetal bovine serum) in a 5% CO2 incubator at 37° C. Replication-deficient adenoviral (Ad) constructs harboring wild-type Shp2 (Ad-Shp2 WT), the E76A gain-of-function Shp2 mutant (Ad-Shp2E76A), and green fluorescent protein (GFP) (Ad-GFP) were prepared as previously described (Eminaga, S., et al., J. Biol. Chem., 283:15328-15338). NIH 3T3 and SYF cells were infected with adenovirus at a dosage of 50 multiplicities of infection (MOI). The pJ3Ω vectors containing SrcWT and the K295R/Y527F dominant-negative Src mutant (SrcK295R/Y527F) have been described previously (Fornaro, M., et al., J. Cell Biol., 175:87-97). The pIRES-GFP plasmids encoding the Shp2 WT, gain-of-function/Noonan syndrome mutants of Shp2 (Shp2E76A and Shp2N308D), and Noonan syndrome with multiple lentigines mutants of Shp2 (Shp2Y279C and Shp2T468M) have been described previously (Kontaridis, M I, et al., J. Biol. Chem., 281:6785-6792). The zebrafish Shp2 mutants have been cloned previously (Jopling, C., et al., PLoS Genet., 3:e225). The zebrafish PZR (zPZR) was cloned by nested PCR from zebrafish embryo cDNA (from bud stage to 48 h postfertilization [hpf]). The zPZR ITIM Y236F, Y258F, and Y236F Y258F mutants were made using site-directed mutagenesis. RPTPa signal sequence and Hemagglutinin (HA) tag were incorporated into N-terminus of zPZR. DNA transfection into HEK-293 and SYF cells was performed using Lipofectamine 2000 according to the manufacturer's protocol.

Ms Analysis.

The PhosphoScan method was performed as previously described (Rikova, K., et al., Cell, 131:1190-1203). Wild-type and Shp2 mutant (Noonan syndrome) mouse hearts were homogenized, sonicated, and centrifuged to remove cellular debris. Total protein for each tissue was normalized using the ProteinPlus Coomassie reagent (Pierce), and proteins were reduced, alkylated, and digested overnight using trypsin (Worthington). The resulting peptides were separated from non-peptide material by solid-phase extraction with Sep-Pak classic $C_{18}$ cartridges (Waters). Lyophilized peptides were redissolved, and phosphopeptides were enriched by immunoaffinity purification using pY-100 phosphotyrosine antibody (9411; Cell Signaling Signaling Technology). Peptides were eluted with 0.15% trifluoroacetic acid (TFA) and concentrated with $C_{18}$ spin tips immediately prior to liquid chromatography-mass spectrometry (LC-MS) analysis. Duplicate injections of each sample were run to generate analytical replicates and increase the number of tandem MS (MS/MS) identifications from each sample. Peptides were loaded directly onto a 10-cm by 75-μm PicoFrit capillary column packed with Magic $C_{18}$ AQ reversed phase resin. The column was developed with a 45-min linear gradient of acetonitrile in 0.125% formic acid delivered at 280 nl/min. Tandem mass spectra were collected with an LTQ-Orbitrap XL mass spectrometer running XCalibur using a Top 10 method, a dynamic exclusion repeat count of 1, and a repeat duration of 30 s. MS spectra were collected in the Orbitrap component of the mass spectrometer, and MS/MS spectra were collected in the LTQ portion. MS/MS spectra were processed using SEQUEST and the Core platform (Gygi Lab, Harvard University). Searches were performed against the mouse NCBI database, with reverse decoy databases included for all searches to estimate false-positive rates. Peptide assignments were obtained using a 0.98-precision cutoff in the linear discriminant analysis module of Core. Cysteine carboxamidomethylation was specified as a static modification, and methionine oxidation and serine, threonine, and tyrosine phosphorylation were allowed. Results were further narrowed using mass accuracy (5-ppm) filters and the presence of a phosphotyrosine in the peptide. Label-free quantitation was performed using Progenesis v4.1 (Nonlinear Dynamics). Peptide abundance data were manually reviewed in Progenesis for all peptides with at least a 2.0-fold change to ensure accuracy of results.

Animal Handling—

Ptpn11$^{D61G/+}$ mice were provided from Dr. Benjamin Neel (University of Toronto, Toronto) and were genotyped as described previously (Araki T, Mohi M G, Ismat F A, Bronson R T, Williams I R, Kutok J L, Yang W, Pao L I, Gilliland D G, Epstein J A, Neel B G. 2004. Mouse model of Noonan syndrome reveals cell type- and gene dosage-dependent effects of Ptpn11 mutation. Nat Med 10:849-

857). Briefly, Ptpn11$^{D61G/+}$ male mice were crossed with WT C75BL/6×SV129 female mice and their offspring were genotyped by PCR and digestion with AgeI for D61G allele.

Dasatinib Treatment—

N-(2-chloro-6-methylphenyl)-2-[[6-[4-(2-hydroxyethyl)-1-piperazinyl]-2-methyl-4-pyrimidinyl]amino]-5-thiazole carboxamide monohydrate (dasatinib, BMS-354825) was purchased from Biovision. dasatinib was dissolved in DMSO at a concentration of 10 mg/ml, then resuspended in vehicle (1× Dulbecco's PBS) at a concentration of 200 μg/ml. WT and Ptpn11$^{D61G/+}$ male mice were injected daily with dasatinib (0.1 mg/kg, i.p.), beginning at postnatal day 10 until 6-weeks after birth (P42). And then, injection was continued or discontinued for 2 weeks Vehicle-injected mice served as control. Body weight was measured weekly and echocardiography was performed at P42 (6-weeks) and P56 (8-weeks). Animal handling was approved by The Yale University Institutional Animal Care and Use Committee.

Echocardiographic Studies—

Cardiac dimensions and function were analyzed by echocardiography using a Vevo 770 console. Mice were lightly anesthetized with inhaled isoflurane (0.2% in $O_2$). All measurements were obtained from three to six consecutive cardiac cycles, and the averaged values used for analysis. Interventricular septum wall (IVS), left ventricular internal dimension (LVID) and left ventricular posterior wall thickness (LVPW) in both end-diastolic (d), end-systolic (s) were measured from the T- and M-mode tracings. Diastolic measurements were performed using the leading-edge method of the American Society of Echocardiography. For TM-mode measurements, left ventricular end-diastolic volume (LV vol,d) and end-systolic volume (LV vol,s) were calculated. Ejection fraction percentage (EF) was calculated as [(LVvol, d−LVvol,s)/VLvol,d]×100, and fractional shortening percentage was calculated as [(LVID,d−LVID,s)/LVID,d]×100.

Statistical Analysis—

Statistical values are presented as the mean±s.e.m. A two-way ANOVA (Tukey's multiple comparisons) test was used to calculate the P values. All statistical analyses were performed with GraphPad Prism 5. For all studies, a P value less than 0.05 was considered significant.

The Materials and Methods used in the performance of the experiments in Example 2 disclosed herein are now described.

Antibodies, Chemicals, Cell Lines and Plasmids—

The following antibodies were used either for immunoblotting (IB) or immunoprecipitation (IP) as indicated. Mouse monoclonal Flag (F1804, IP-1:100, IB-1:1,000) and mouse monoclonal biotinylated Flag (F9291, IB-1:1,000) antibodies were from Sigma. Mouse monoclonal Myc (sc-40, IP-1:100, IB-1:1,000), mouse monoclonal biotinylated Myc (sc-40B, IB-1:1,000), rabbit polyclonal Shp2 (sc-280, IB-1:1,000), mouse monoclonal p38 (sc-535, IB-1:1,000), mouse monoclonal GST (sc-138, IB-1:1,000) antibodies were from Santa Cruz Biotechnology. Rabbit monoclonal phospho-PZR (Y241; #8181, IB-1:1,000), rabbit monoclonal phospho-PZR (Y263; #8088, IB-1:1,000), rabbit polyclonal phospho-Src (Y416; #2101, IB-1:1,000), mouse monoclonal Src (#2110, IB-1:1,000), mouse monoclonal Raf1 (#12552, IB-1:1,000), rabbit polyclonal phospho-MEK1/2 (S217/221; #9154, IB-1:1,000) mouse monoclonal MEK1/2 (#4694, IB-1:1,000), rabbit polyclonal phospho-ERK1/2 (T202/Y204; #9101, IB-1:1,000), mouse monoclonal ERK (#9107, IB-1:1,000), rabbit polyclonal phospho-p38 (T180/Y182; #9215, IB-1:1,000), rabbit polyclonal phospho-JNK (T183/Y185; #4668, IB-1:1,000), mouse monoclonal JNK (#3708, IB-1:1,000), rabbit polyclonal phospho-Akt (S473; #9271, IB-1:1,000), mouse monoclonal Akt (#2967, IB-1:1,000), rabbit polyclonal SERCA2A (#9580, IB-1:1,000), rabbit polyclonal Troponin I (#4002, IB-1:1,000) antibodies were purchased from Cell Signaling. Rabbit polyclonal phospho-Raf1 (Y341; ab192820, IB-1:1, 000) and rabbit polyclonal alpha tubulin (ab4074, IB-1:1, 000) antibodies were obtained from Abcam. Mouse monoclonal Shp2 (#610622, IB-1:1,000) antibody was purchased from BD Biosciences. Mouse monoclonal His (#11922416, IB-1:1,000) antibody was from Roche. Rabbit polyclonal Troponin T (MS-295, IB-1:1,000) was from Thermo Scientific. Rabbit polyclonal PZR antibody (IB-1:1,000) was generously provided by Z. J. Zhao. Dasatinib was purchased from Biovision and STI-571 was obtained from LKT laboratories. Shp2 phosphatase inhibitor was generously provided by Z.-Y. Zhang (Indiana University). HEK-293T cells were purchased from ATCC and mouse embryonic fibroblasts (MEFs) were isolated from WT and Ptpn11$^{D61G/+}$ mice. Cells were grown in growth medium (Dulbecco's modified Eagle's medium [DMEM] supplemented with 1% penicillin-streptomycin and 10% fetal bovine serum) in a 5% $CO_2$ incubator at 37° C. Human Src and Ptpn11 full length, N+C and PTP constructs were generated by PCR and cloned into the pCMV-3Tag4a and pCMV-Tag2b (Clontech laboratories) vectors. DNA transfection into HEK-293T cells was performed using Lipofectamine 3000 (Invitrogen) according to the manufacturer's protocol.

Immunoprecipitation and Immunoblotting—

Cells or heart tissue were lysed on ice in lysis buffer (25 mM Tris-HCl, pH 7.4, 136 mM NaCl, 1 mM $CaCl_2$, 1 mM $MgCl_2$, 1% Nonidet P-40, 1 mM $Na_3VO_4$, 10 mM NaF, 1 mM benzamidine, 1 mM PMSF, 1 μg/ml pepstatin A, 5 μg/ml aprotinin, and 5 μg/ml leupeptin). Cell or tissue lysates were incubated at 4° C. for 30 min and clarified by centrifugation at 14,000 rpm at 4° C. for 10 min. Protein concentration was determined using the BCA reagent according to the manufacturer's instructions (Pierce). For immunoprecipitations, 500 μg of lysate was incubated with 1 μg of indicated antibodies at 4° C. for overnight. Immune complexes were collected on either protein A- or protein G-Sepharose beads for 4 hr at 4° C., washed three times with same lysis buffer and then heated to 95° C. in sample buffer for 5 min. Total lysates or immune complexes were subjected to SDS-PAGE and immunoblotting. The sites of antibody binding were visualized using enhanced chemiluminescence detection or Odyssey Imaging System.

In Vitro GST-Pull Down Assay—

Bacterial purified GST-SH3 of Src and His-PTP of Shp2 were provided by T. Boggon (Yale University). Pull-down assays were carried out in 1 ml lysis buffer containing GST-SH3 of Src protein with either His-PTP of Shp2 or Flag-tagged Shp2 overexpressing HEK-293 cell lysates for overnight at 4° C. SH3-bound Shp2 proteins were affinity purified by BSA-coated GST-Sepharose beads for 1 hr at 4° C. The interaction between SH3 of Src and Shp2 proteins was examined using immunoblotting with anti-His or anti-Flag and anti-GST antibodies.

Animal Handling—

Ptpn11$^{D61G/+}$ mice were provided from Dr. Benjamin Neel (University of Toronto, Toronto) and were genotyped as described previously[9]. Briefly, Ptpn11$^{D61G/+}$ male mice were crossed with wild type C75BL/6×SV129 female mice and their offspring were genotyped by PCR and digestion with AgeI for the D61G allele. Dasatinib (Biovision) was suspended in vehicle (1% DMSO in phosphate buffer saline). For prenatal treatment, dasatinib was injected i.p. (0.1 mg/kg body weight) into pregnant mice daily, beginning on gestational day 7.5 (E7.5) continuing (in nursing females) until postnatal day 9. Vehicle-injected mice served as control. Beginning at P10, dasatinib or vehicle alone was injected (i.p.) directly into pups daily, until 8-weeks after birth. For postnatal treatment, dasatinib was injected (i.p.) into pups at P10, until 6-weeks after birth; injection was discontinued for 2-weeks. Animal handling was approved by The Yale University Institutional Animal Care and Use Committee.

Histology—

Heart, liver and spleen were isolated from vehicle- or dasatinib-treated wild type and NS mice. Tissues were fixed in 4% paraformaldehyde in phosphate-buffer saline (PBS), processed for paraffin sections and stained with hematoxylin and eosin (H&E) or Masson's Trichrome. Tissue images were obtained under bright field microscopy (Olympus BX51, Yale Liver Center).

Echocardiography—

Mice were anesthetized in a sealed plastic chamber with 1% isofurane in oxygen until immobile, and then were transferred onto a heated procedure board (37° C.). Animal were kept anesthetized with 1% isoflurane supplied by a nose cone connected to the isoflurane vaporizer during the entire procedure. The scan head was placed on the chest of the mouse and stable image signals (both B mode and M mode) were acquired and data analyzed with Vevo 770 (VisualSonics). Systolic and diastolic left ventricle peripheral wall thickness, chamber diameter and interventricular wall thickness were measured with M mode image. Percentage of ejection fraction (EF) and fractional shortening (FS) were calculated.

Hemodynamic Study—

Anesthesia was induced by intraperitoneal injection of ketamine (100 mg/kg) and xylazine (5 mg/kg). The animal was placed on a warm pad and an incision was made on the neck. The right side carotid artery was exposed and a 1.9-French transducer-tipped catheter (Millar Inc., Houston, Tex.) was inserted into the artery, and then was advanced into left ventricle. Left ventricular pressures including high-fidelity positive, negative dp/dt and heart rate were measured under basal conditions. Data were recorded and analyzed by using LabChart software.

RNA Extraction and Quantitative Real-Time PCR Analysis—

RNA was isolated from mice heart using an RNeasy kit (Qiagen, CA) according to the manufacturer's instructions. A total of 1 μg RNA was reverse transcribed to generate cDNA using a reverse transcriptase PCR kit (Applied Biosystems, CA). Real-time quantitative PCR was carried out in triplicate using the Applied Biosytems 7500 Fast real-time PCR system and SYBR green gene expression master mix with following primer pairs.

18S rRNA,
SEQ ID NO: 1
5'-ACCGCAGCTAGGAATAATGGA-3',

SEQ ID NO: 2
5'-ACCAAAAGCCTTGACTCCG-3';

ANF,
SEQ ID NO: 3
5'-CCTGGAGGAGAAGATGCCGGTAGAA-3',

SEQ ID NO: 4
5'-CCCCAGTCCAGGGAGGCACCTCGG-3';

BNP,
SEQ ID NO: 5
5'-CACTTCAAAGGTGGTCCCAGAGCTGC-3',

SEQ ID NO: 6
5'-GACCGGATCGGATCCGTCAGTCG-3';

αMHC,
SEQ ID NO: 7
5'-GTCCCGGACACTGGACCAGGCC-3',

SEQ ID NO: 8
5'-CTCCTTTTCTTCCAGTTGCCTAGCCAA-3';

βMHC,
SEQ ID NO: 9
5'-GAGCAAGGCCGAGGAGACGCAGCGT-3',

SEQ ID NO: 10
5'-GAGCCTCCTTCTCGTCCAGCTGCCGG-3';

Col1a2,
SEQ ID NO: 11
5'-AGGTCTTCCTGGAGCTGATG-3',

SEQ ID NO: 12
5'-ACCCACAGGGCCTTCTTTAC-3';

Col3a1,
SEQ ID NO: 13
5'-ACAGCAAATTCACTTACACAGTTC-3',

SEQ ID NO: 14
5'-CTCATTGCCTTGCGTGTTT-3'.

All relative gene expression levels were analyzed using the $\Delta C_T$ method and normalized to 18S rRNA expression.

Enzymatic Digestion of Cardiac Tissue for Single-Cell Analysis—

Cardiomyocytes from 8 week old mice were isolated by a Langendorff procedure, modified from Xianghua Xu, et al. J Vis Exp. 2009; (28):1308. In brief, the hearts were quickly excised and cannulated to a Langendorff apparatus where they were perfused with 37° C. $Ca^{2+}$-free perfusion buffer (in 25 mM HEPES, 118 mM NaCl, 4.8 mM KCl, 2.0 mM $KH_2PO_4$, 2.55 mM $MgSO_4$, 10 mM BDM and 10 mM Glucose). To digest the tissue, the heart was perfused with buffer containing 0.5 mg/mL Liberase TH (Roche Applied Science, Penzberg, Germany). After ~10 min, the heart was removed from the Langendorff apparatus and the right ventricle and atria removed. The left ventricle was isolated, cut into small pieces and digested further at 37° C. digestion solution with mechanical agitation for 5-10 min, and then gently triturated to liberate individual cells. The remaining tissue chunks were transferred to fresh digestion buffer and the process was repeated up to 6 times, or until all tissue was digested. Cells were removed from collagenase by gentle centrifugation and resuspended in several washing steps of buffer containing FBS and gradually reintroduced to calcium (0.05-1.1 mM) through step-wise additions of concentrated $CaCl_2$ solution. Cells were allowed to rest for at least 1 h before imaging.

Cardiomyocyte Functional Characterization—

Cardiomyocytes were imaged in Tyrodes solution (in 150 mM: NaCl: 140, KCl: 5.4, $CaCl_2$:1.8, $MgCl_2$:1, HEPES: 25 mM, glucose: 10 mM). Cell pellets were loaded for 15 minutes in the dark with Tyrodes supplemented with 2.5 μM Fura-2 AM complimented with pluronic acid (20% w/v), for calcium fluorescence imaging. After 15 minutes of loading, the cells were resuspended in fresh Tyrodes solution and allowed to settle until imaging. Cardiomyocyte $Ca^{2+}$ transients and unloaded shortening contractions were measured using an inverted microscope (Nikon Eclipse, Chiyoda, Tokyo) equipped with a temperature controlled perfusion bath (Cell MicroControls, Norfolk, Va.) under constant perfusion of 37° C. Tyrodes solution. Cells were field-stimulated at 1 Hz. Contractile events were imaged in real-time using a sarcomere length camera system (HVSL, Aurora Scientific, Ontario, Canada). Only rod-shaped cells with well-defined sarcomere striations that contracted when stimulated were selected for measurement. Sarcomere length was measured and recorded for ten consecutive beats and subsequently averaged across beats to produce a single waveform. Calcium transient measurements were recorded simultaneously using alternating excitation wavelengths of 340 and 380 nm generated at an overall rate of 100 Hz by a RatioMaster fluorescence system (PTI, Birmingham, N.J.). Fluorescence emission was filtered at a center wavelength of 510 nm and quantified to obtain responses to the alternating excitation wavelengths ($F_{340}$ and $F_{380}$, respectively). $Ca^{2+}$ transients were reported as the interpolated ratio of the two fluorescence intensities ($F_{340}/F_{380}$) at each time point. Data were recorded using a DAP5216a data acquisition system (Microstar Laboratories, Bellevue, Wash.) and processed using custom software written in MATLAB (MathWorks, Natick, Mass.). Peak sarcomere length shortening (Peak SL shortening), time to peak shortening (TTP), time to 50% re-lengthening (RT50), the magnitude of the calcium transient ($Ca^{2+} R_{mag}$: Max $F_{340}/F_{380}$–Min $F_{340}/F_{380}$) and the rate of calcium decay, Tau ($Tau_{Ca2+}$) were computed.

Statistical Analysis—

All data represent the means±standard errors of the means (SEM). Differences between groups were assessed using analysis of variance (ANOVA) with Tukey multiple comparisons using the GraphPad Prism 6 statistical software program.

The Results of the experiments disclosed herein are now described.

Figure 1A:
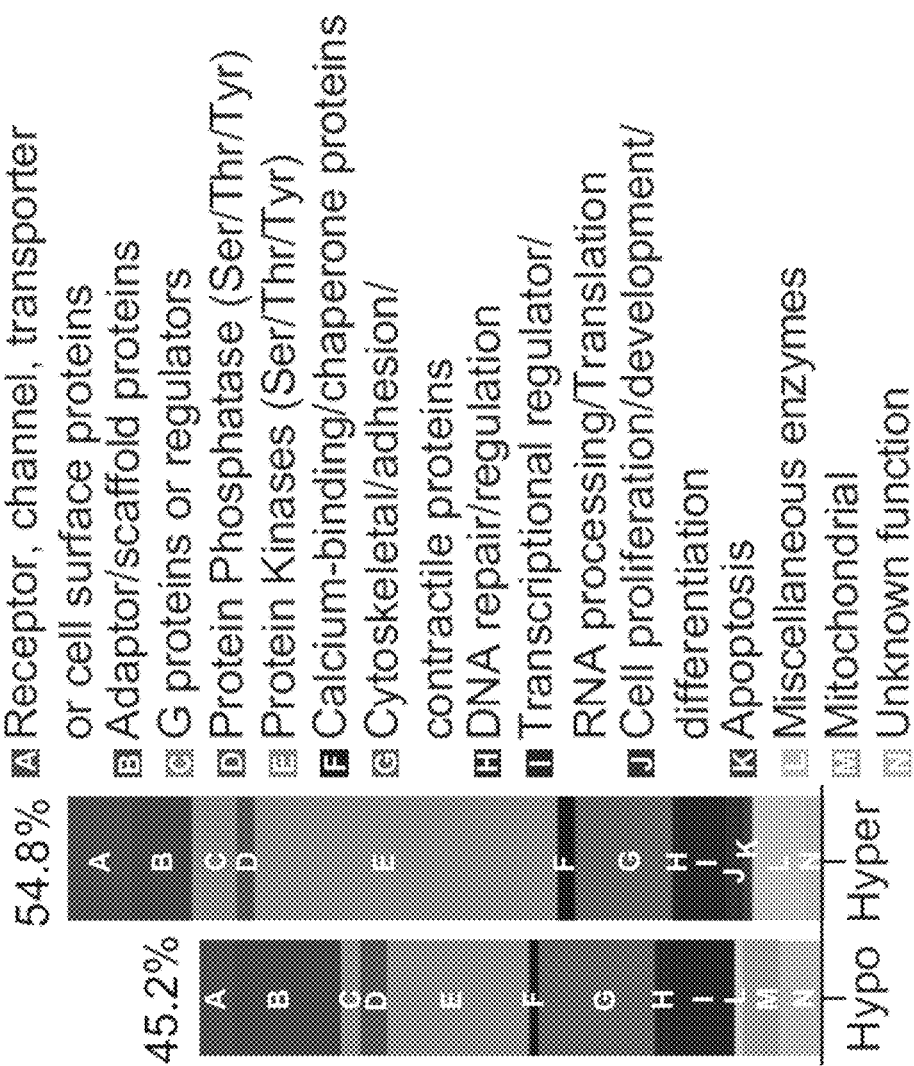
FIG. 1A is an illustration of a proteomic analysis of differentially tyrosyl-phosphorylated proteins in hearts of Ptpn11$^{D61G/+}$ mice. Classification of hypo- and hyper-tyrosylphosphorylated proteins in the hearts of Ptpn11$^{D61G/+}$ mice.

Example 1: Targeting RASopathy-Mediated Cardiac Disease with Tyrosine Kinase Intervention FIG. 1A is an illustration of a proteomic analysis of differentially tyrosyl-phosphorylated proteins in hearts of $Ptpn11^{D61G/+}$ mice.

Figure 1B:
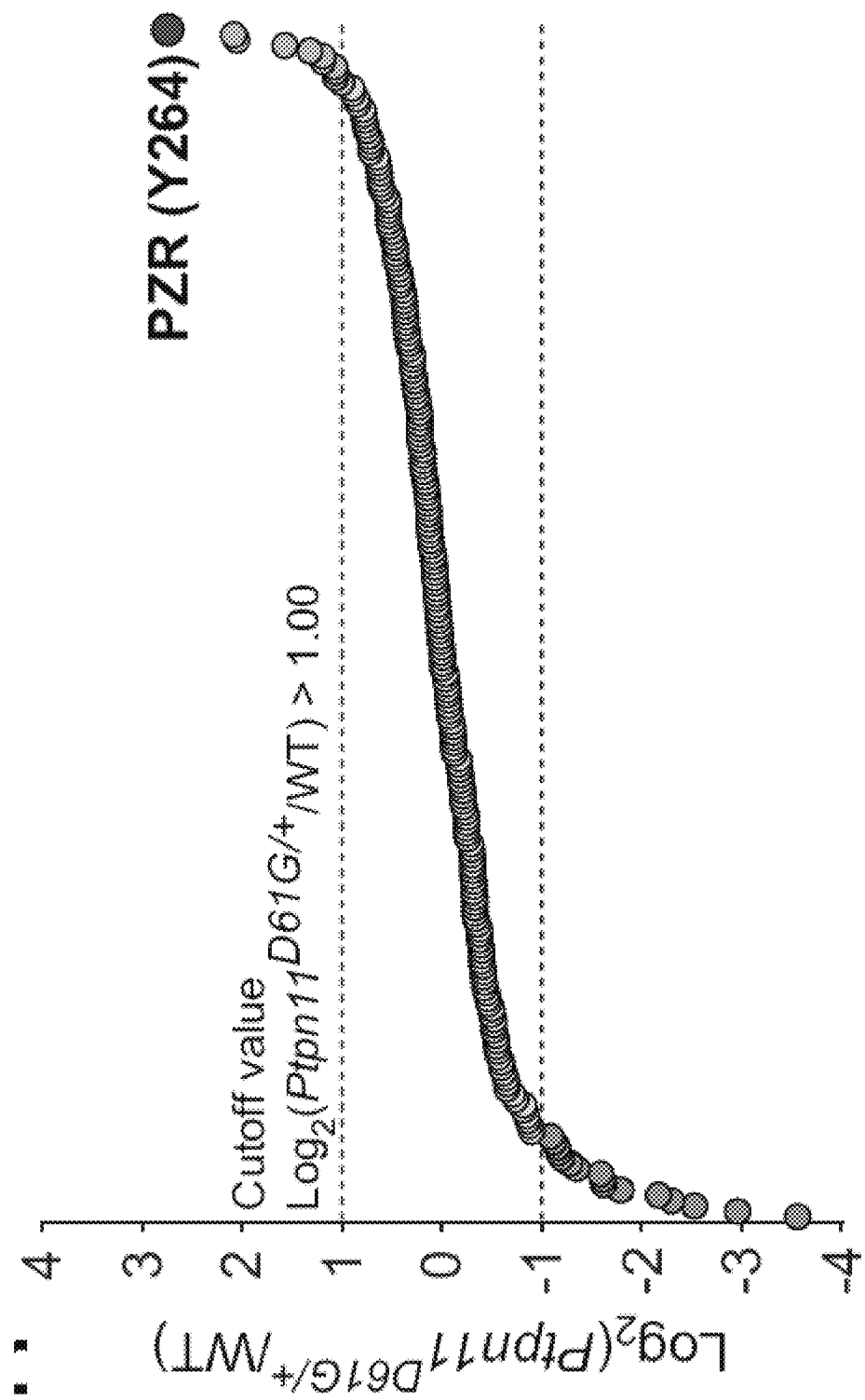
FIG. 1B is graph showing log 2-transformed values for the ratio of each phosphotyrosine-containing peptide in wild-type and Ptpn11$^{D61G/+}$ mouse hearts.
Figure 1C:
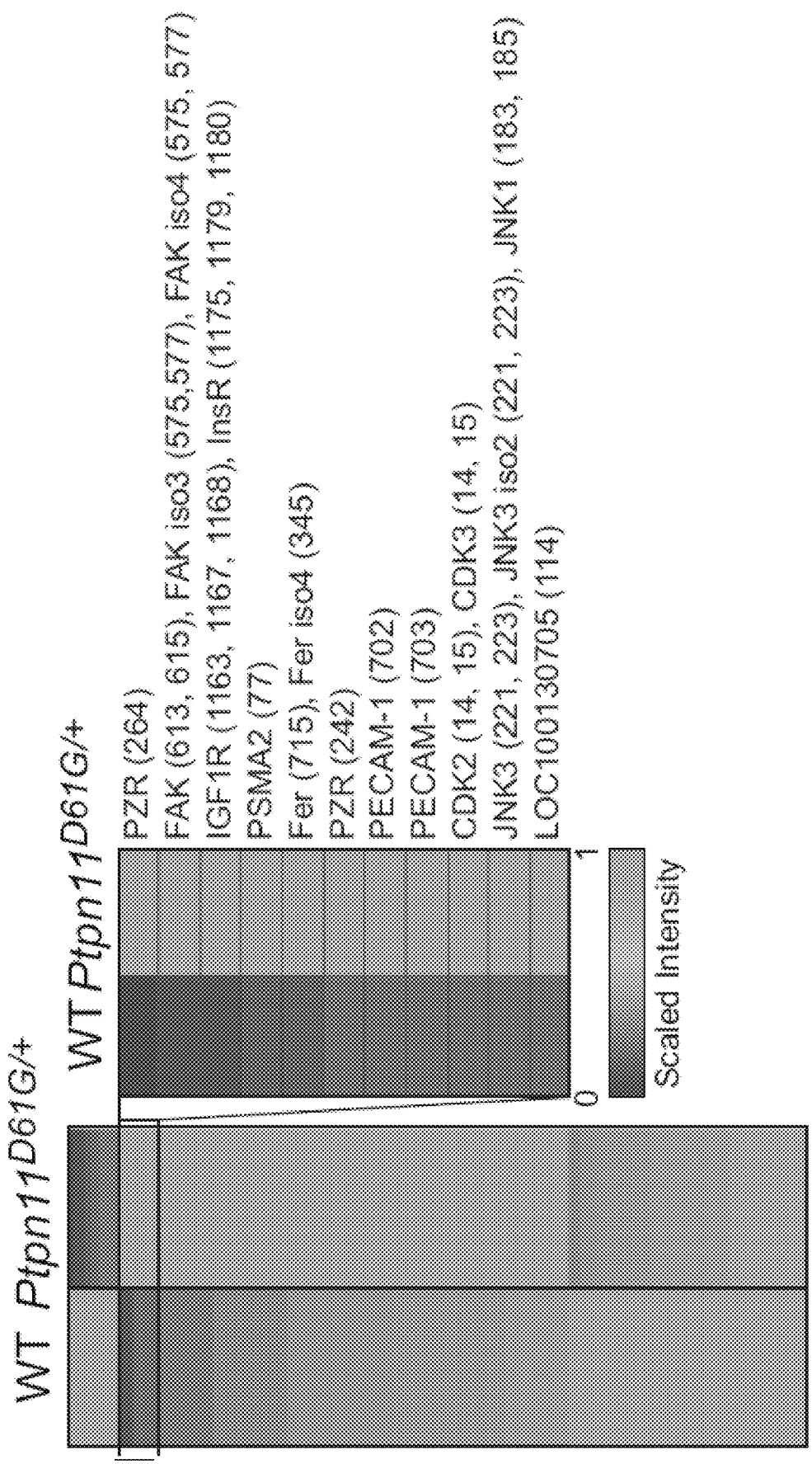
FIG. 1C is a heat map of differentially hyper-tyrosylphosphorylated peptides (the site of phosphorylation is identified by MS in parentheses).
Figure 1D:
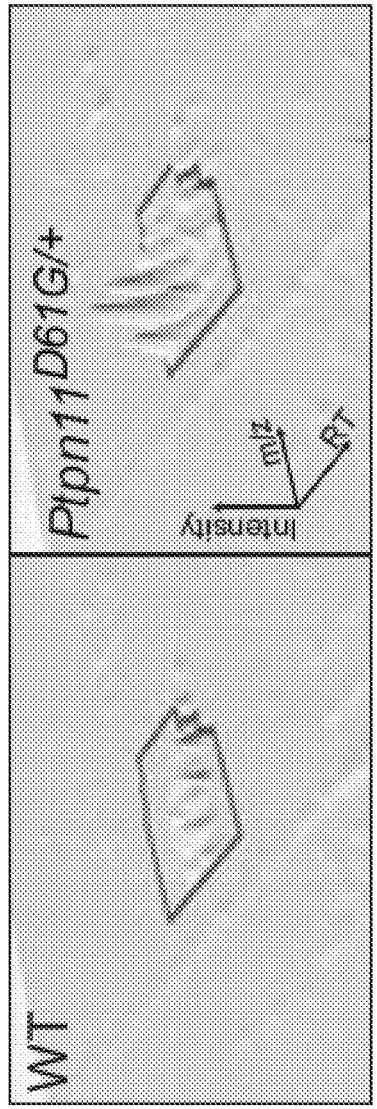
FIG. 1D is a panel of images of extracted ion chromatogram and peptide sequence of PZR-containing tyrosine 242 (upper panels) and tyrosine 264 (lower panels) by differential proteomics.
Figure 1D:
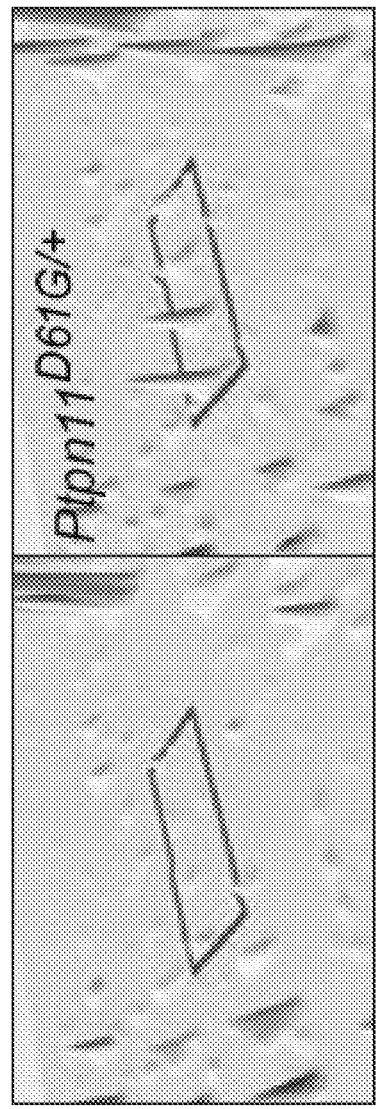
Figure 2A:
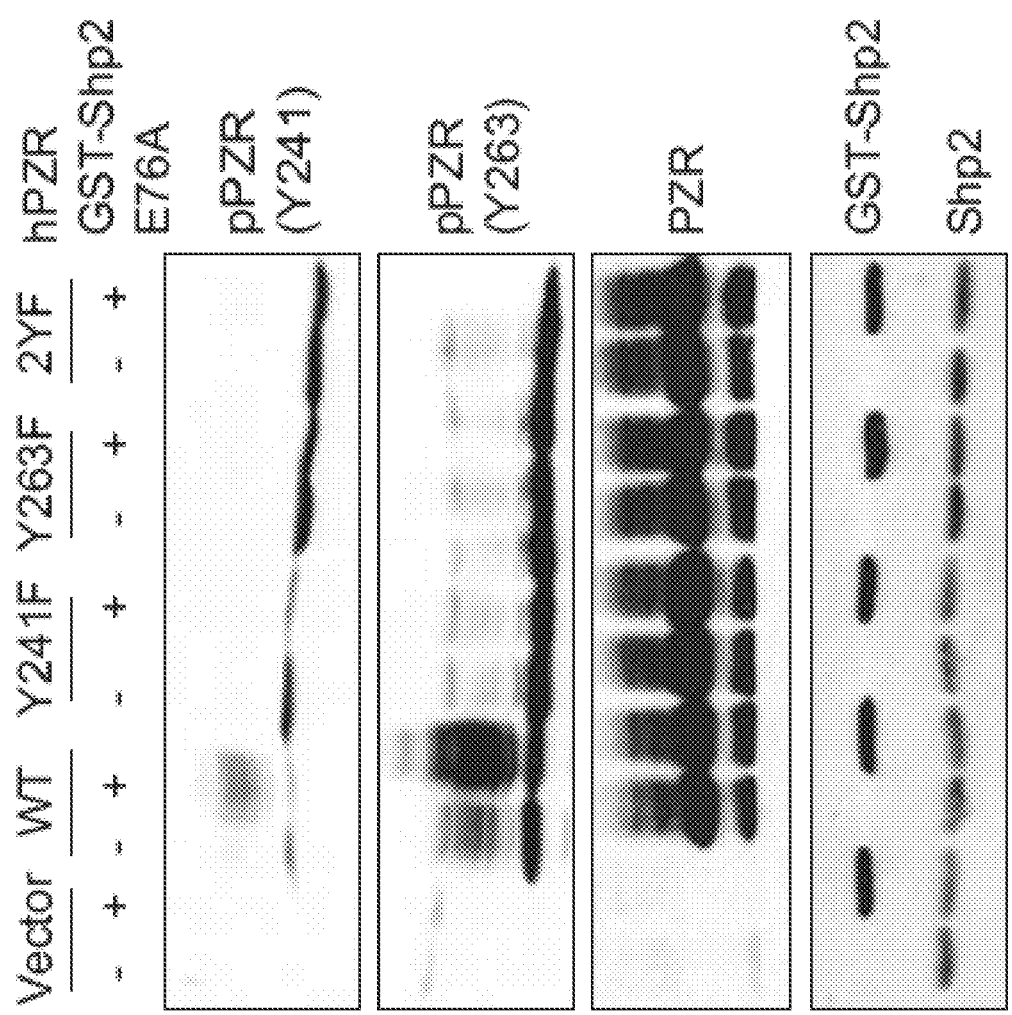
FIG. 2A is a panel of blots showing the characterization of PZR tyrosyl phosphorylation. C2C12 cells were cotransfected with empty vector or activated glutathione S-transferase (GST)-Shp2E76A and either empty vector (vector), wild-type human PZR (WT), or PZR mutated at tyrosine 241 (Y241F), tyrosine 263 (Y263F), or both (2YF). Cell lysates were immunoblotted with anti-pPZR (Y241 or Y263), -PZR, or -Shp2 antibodies.
Figure 2B:
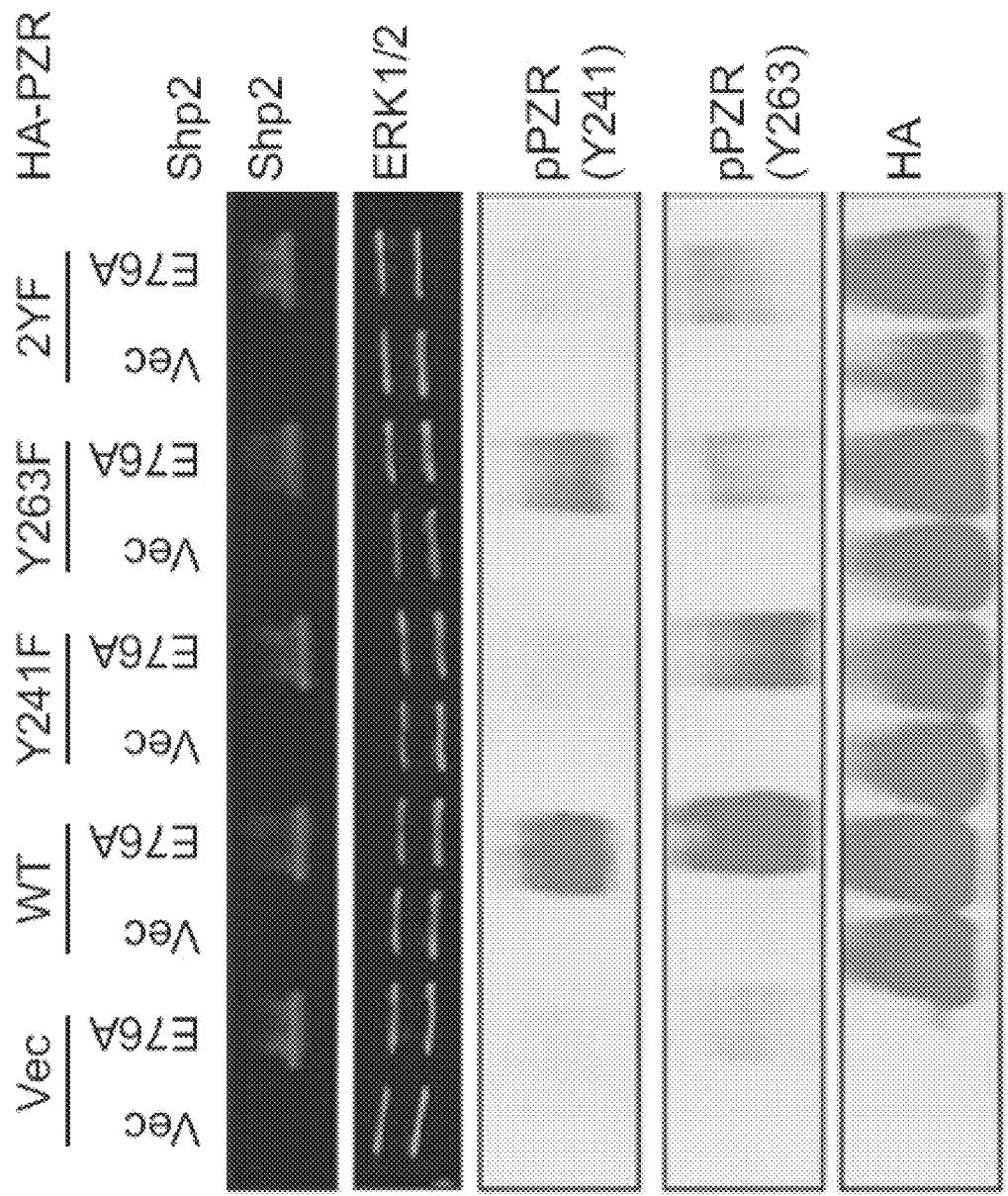
FIG. 2B is a panel of blots showing the characterization of PZR tyrosyl phosphorylation. HEK-293 cells co-transfected with empty vector (Vec) or activated Shp2E76A and either empty vector (vector), wild-type zebrafish PZR (WT), or PZR mutated at tyrosine 236 (Y241F), tyrosine 258 (Y263F), or both (2YF). Cell lysates were immunoblotted with anti-pPZR (Y241 or Y263), PZR, or Shp2 antibodies. ERK1/2 was used as a loading control.
Figure 3B:
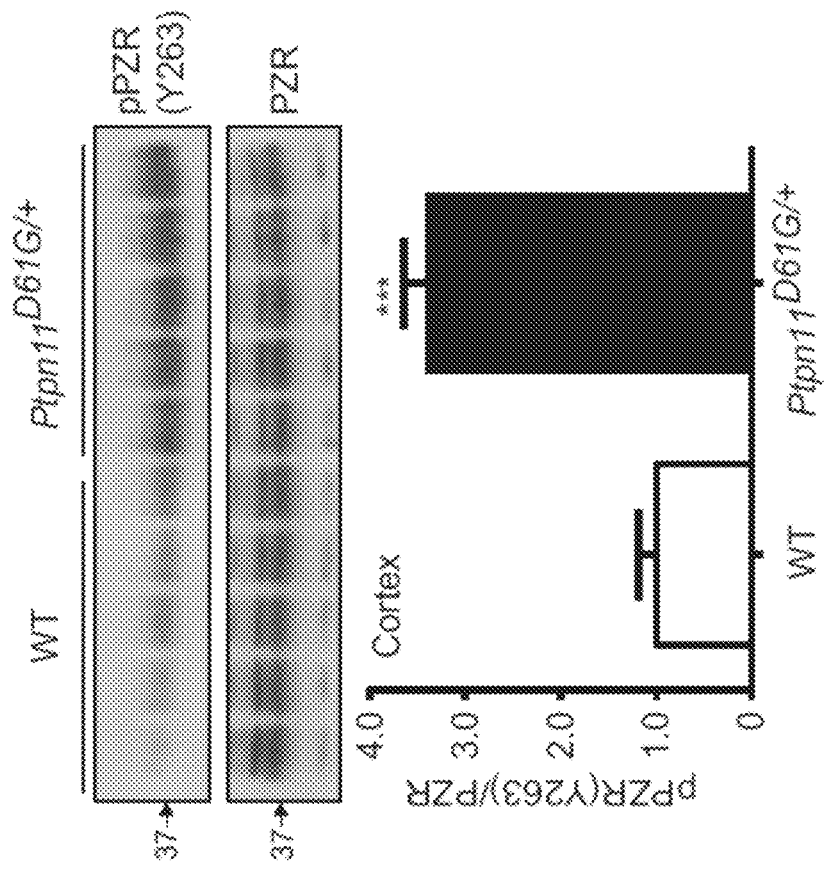
FIG. 3B shows PZR tyrosyl phosphorylation in the cortex of Ptpn11$^{D61G/+}$ mice. The cortex was isolated from 5-week-old WT and Ptpn11$^{D61G/+}$ mice. Tissue lysates were immunoblotted with pPZR (Y263) and total PZR antibodies. Phosphorylation of tyrosine 264 in PZR represents n=5 per genotype. All data are means±standard errors of the means (SEM). ***, P<0.001.
Figure 3A:
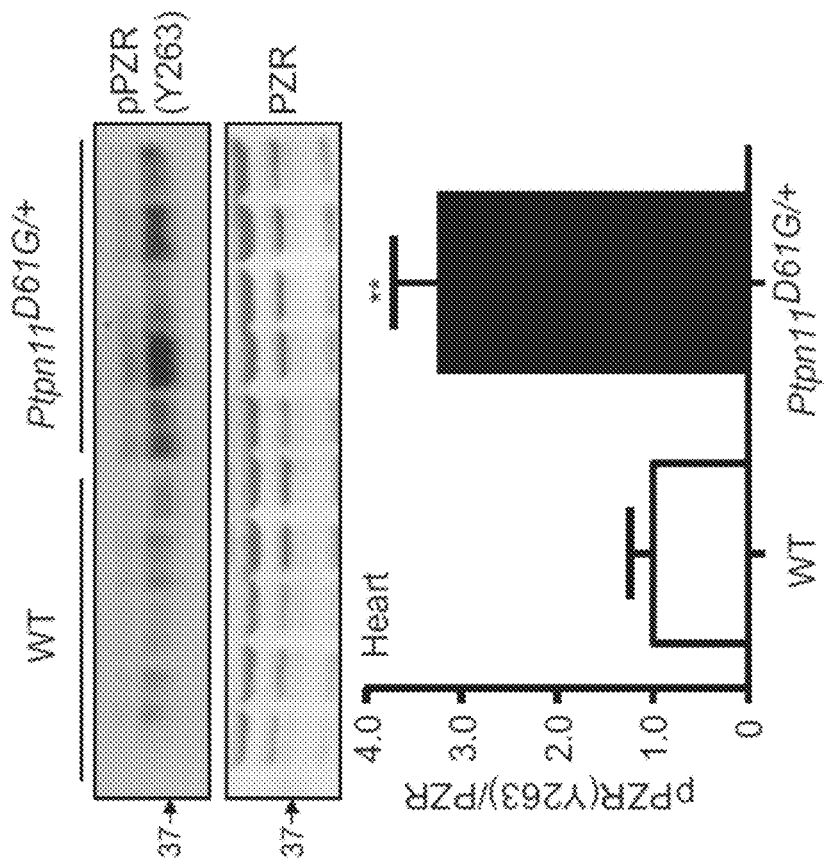
FIG. 3A shows PZR tyrosyl phosphorylation in the hearts of Ptpn11$^{D61G/+}$ mice. The heart was isolated from 5-week-old WT and Ptpn11$^{D61G/+}$ mice. Tissue lysates were immunoblotted with pPZR (Y263) and total PZR antibodies. Phosphorylation of tyrosine 264 in PZR represents n=5 per genotype. All data are means±standard errors of the means (SEM). **, P<0.01.
Figure 3D:
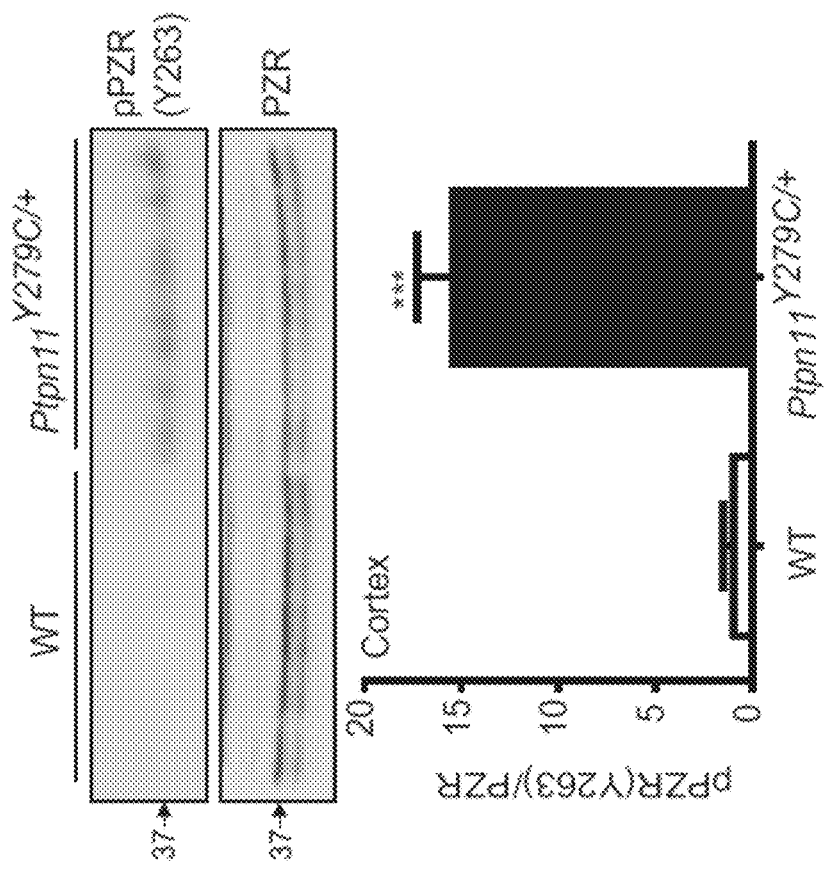
FIG. 3D shows PZR tyrosyl phosphorylation in the cortex of Ptpn11$^{Y279C/+}$ mice. The cortex was isolated from 8-week-old WT and Ptpn11$^{Y279C/+}$ mice. Tissue lysates were immunoblotted with pPZR (Y263) and total PZR antibodies. Phosphorylation of tyrosine 264 in PZR represents n=5 per genotype. All data are means±standard errors of the means (SEM). ***, P<0.001.
Figure 3C:
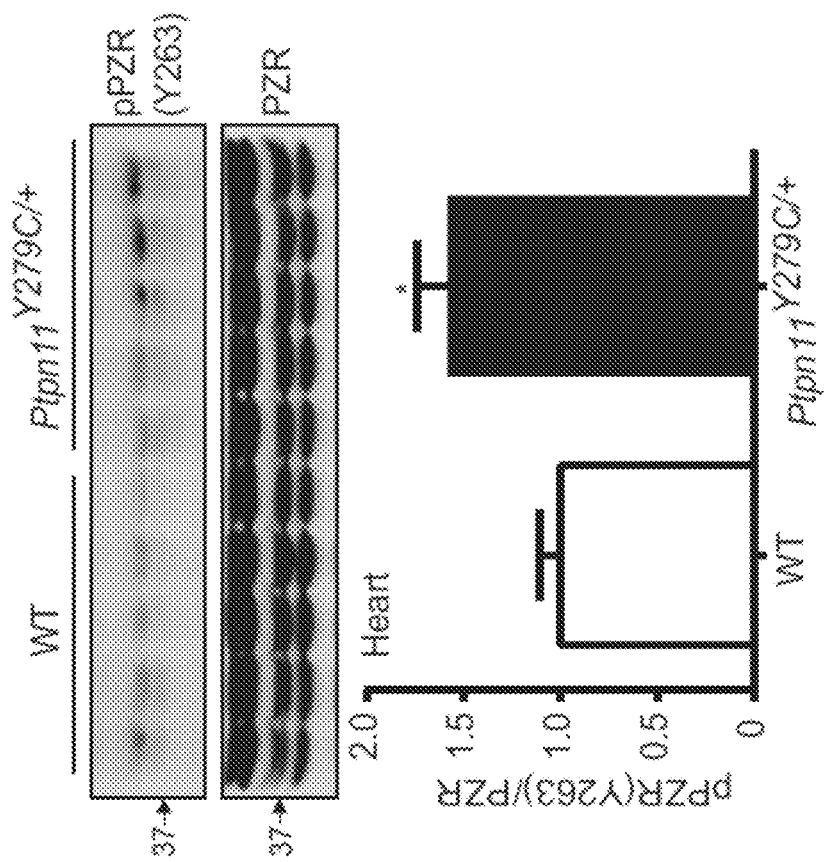
FIG. 3C shows PZR tyrosyl phosphorylation in the heart of Ptpn11$^{Y279C/+}$. The heart was isolated from 8-week-old WT and Ptpn11$^{Y279C/+}$ mice. Tissue lysates were immunoblotted with pPZR (Y263) and total PZR antibodies. Phosphorylation of tyrosine 264 in PZR represents n=5 per genotype. All data are means±standard errors of the means (SEM). *, P<0.05.

FIG. 1B is graph showing log 2-transformed values for the ratio of each phosphotyrosine-containing peptide in wild-type and $Ptpn11^{D61G/+}$ mouse hearts. FIG. 1C is a heat map of differentially tyrosyl-phosphorylated peptides (the site of phosphorylation is identified by MS in parentheses). FIG. 1D is a panel of images of extracted ion chromatogram and peptide sequence of PZR-containing tyrosine 242 (upper panels) and tyrosine 264 (lower panels) by differential proteomics. FIG. 1E shows amino acid sequences of the PZR C terminus in different vertebrates. Global phosphotyrosyl proteomics in the hearts of mice harboring a knockin mutation of the Noonan syndrome mutant ($Shp2^{D61G/+}$) reveals altered regulation of tyrosyl phosphorylated proteins. MS analysis shows that the most abundantly hypertyrosyl phosphorylated protein is PZR in these mice. Tyrosyl residues 264 and 242 were identified to be the sites of PZR tyrosyl phosphorylation that were increased in the hearts of Noonan syndrome ($Shp2^{D61G/+}$) mice. PZR tyrosine 242 and 264 are likely to be important for the function of PZR given that they are highly conserved throughout evolution. These results suggest that increased PZR tyrosyl phosphorylation may play a role in the pathogenesis of Noonan syndrome-related cardiac disease. These results identified Y242 and Y264 as sites of PZR hypertyrosyl phosphorylation in this mouse model of NS.

FIG. 2A-2E show immunoblots showing the characterization of PZR tyrosyl phosphorylation. Conformation of the site of PZR hyper tyrosyl phosphorylation by NS and NSML mutants. Expression of a phosphorylation-resistant mutant of PZR at the site(s) of tyrosyl phosphorylation found in mice impairs its ability to be phosphorylated in cultured cells also as detected using phospho-specific anti-PZR (Y242) and anti-PZR (Y263). Mutants of Shp2 that represent those found either in NS or NSML patients are capable of inducing PZR hypertyrosyl phosphorylation at Y241 and Y263. Similarly, zebrafish PZR exhibits identical properties of being able to be tyrosyl phosphorylated at the comparable residue. These results suggested NS or Leopard syndrome-associated Shp2 mutants induced PZR hyperphosphorylation in various cell lines.

Figure 4A:
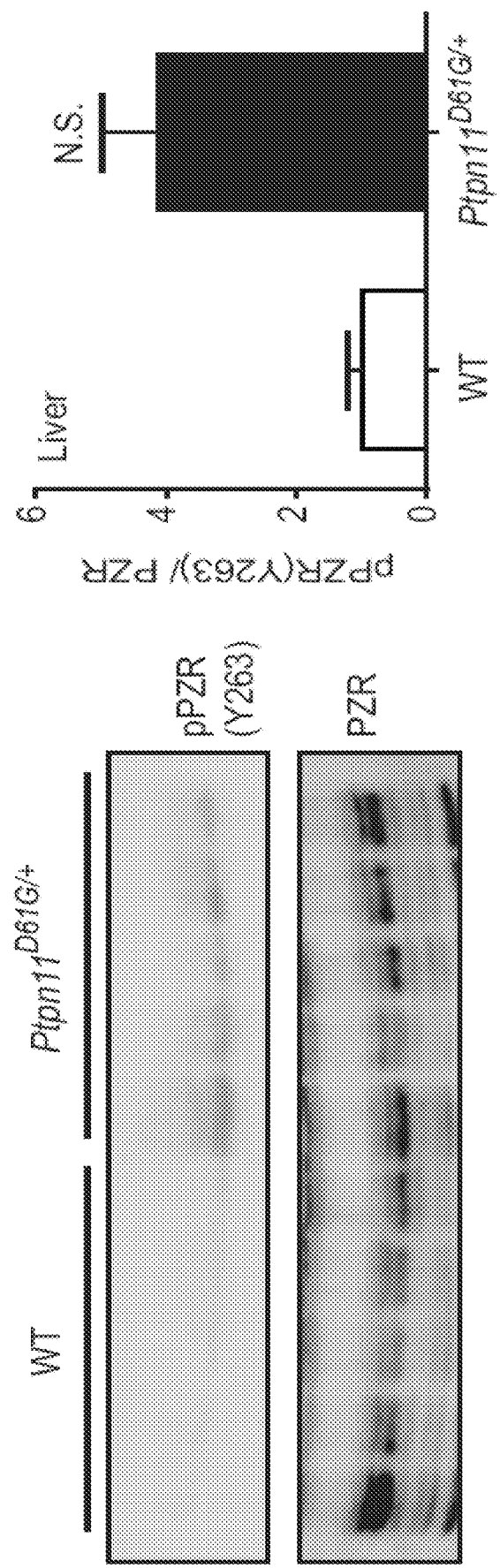
FIG. 4A shows PZR tyrosyl phosphorylation in the liver of Ptpn11$^{D61G/+}$ mice. The liver was isolated from 5-week-old wild-type and Ptpn11$^{D61G/+}$ mice. Tissue lysates were immunoblotted with anti-pPZR (Y263) and -total PZR antibodies. Densitometric analysis of the phosphorylation levels of tyrosine 263 in PZR was performed, and the results represent the means±SEM from 5 mice per genotype.
Figure 4B:
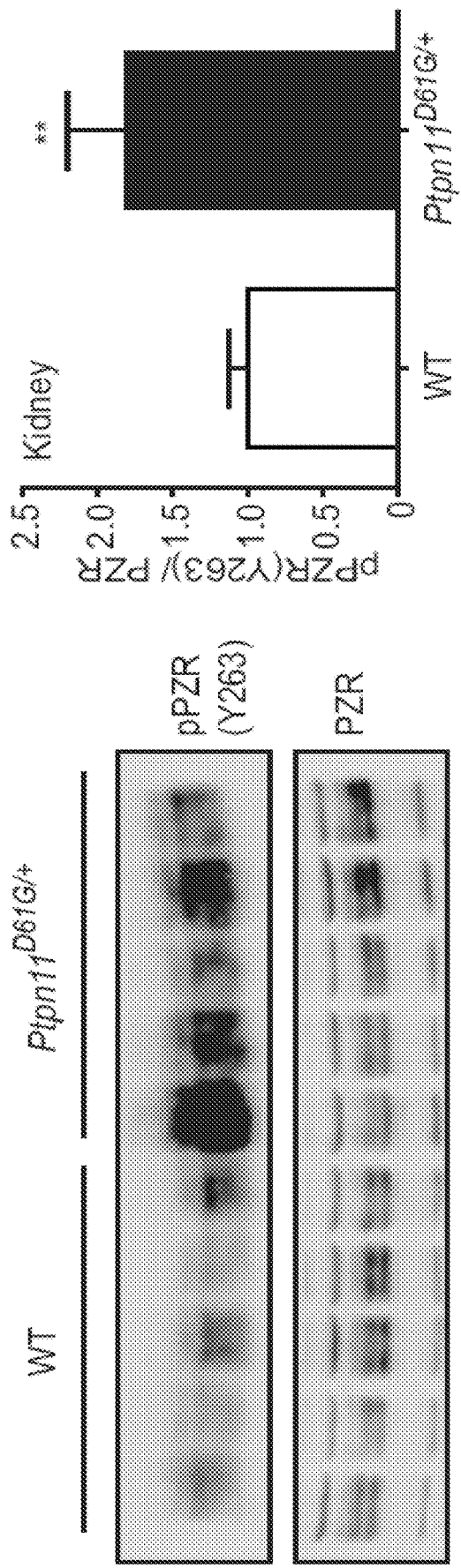
FIG. 4B is an image and a graph showing PZR tyrosyl phosphorylation in the kidney of Ptpn11$^{D61G/+}$ mice. The kidney was isolated from 5-week-old wild-type and Ptpn11$^{D61G/+}$ mice. Tissue lysates were immunoblotted with anti-pPZR (Y263) and -total PZR antibodies. Densitometric analysis of the phosphorylation levels of tyrosine 263 in PZR was performed, and the results represent the means±SEM from 5 mice per genotype. **, P<0.01 (WT versus NS).
Figure 4C:
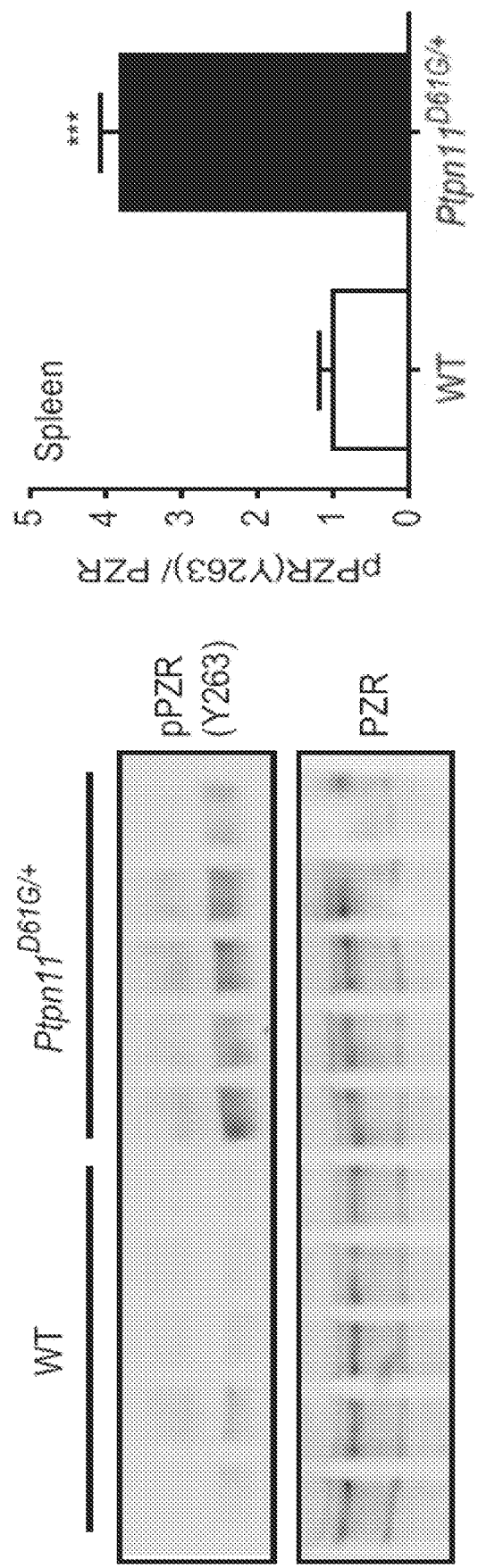
FIG. 4C is an image and a graph showing PZR tyrosyl phosphorylation in the spleen of Ptpn11$^{D61G/+}$ mice. The spleen was isolated from 5-week-old wild-type and Ptpn11$^{D61G/+}$ mice. Tissue lysates were immunoblotted with anti-pPZR (Y263) and -total PZR antibodies. Densitometric analysis of the phosphorylation levels of tyrosine 263 in PZR was performed, and the results represent the means±SEM from 5 mice per genotype. ***, P<0.001 (WT versus NS).
Figure 5A:
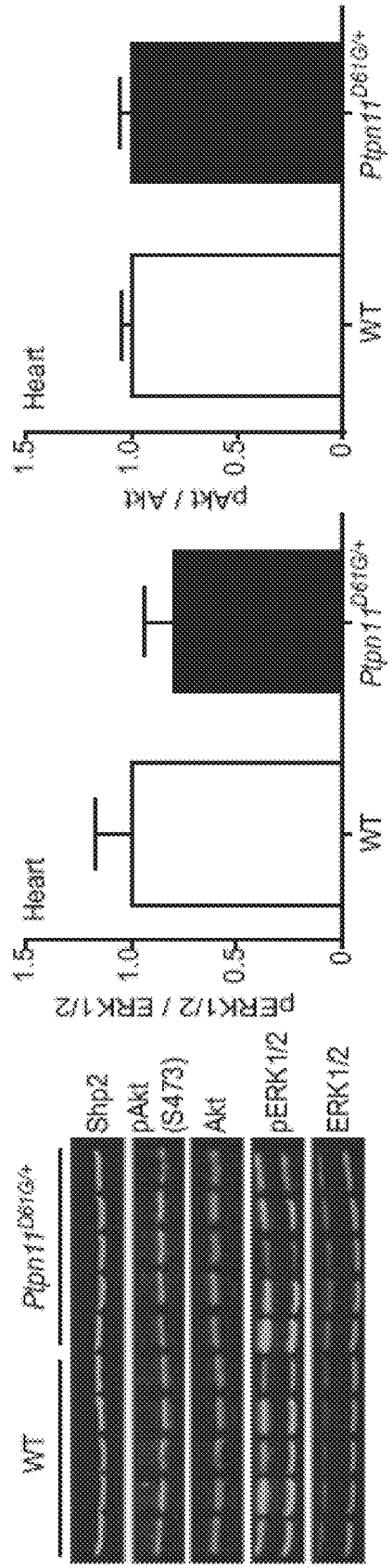
FIG. 5A is a panel of immunoblots showing ERK and Akt phosphorylation in the heart of Ptpn11$^{D61G/+}$ mice. The hearts were isolated from 5-week-old wild-type and Ptpn11$^{D61G/+}$ mice (A and B). Tissue lysates were subjected to immunoblotting with anti-Shp2, -pERK1/2, -total ERK1/2, -pAkt, and -Akt antibodies. The results represent densitometric analyses of the means±SEM for pERK1/2 and pAkt from 5 mice per genotype.
Figure 5B:
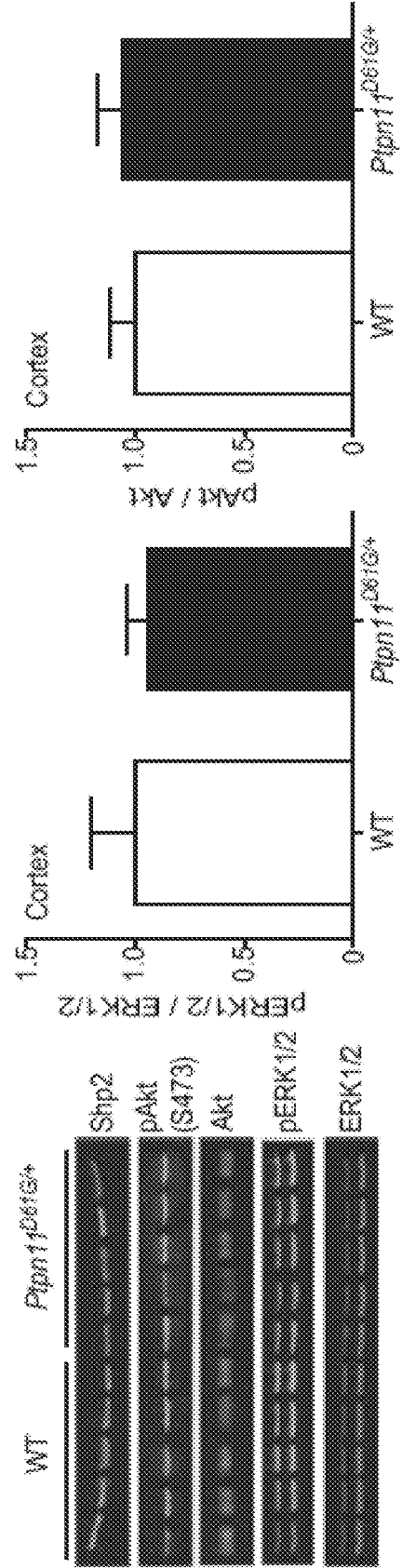
FIG. 5B is a panel of images showing ERK and Akt phosphorylation in the cortex of Ptpn11$^{D61G/+}$ mice. The cortex was isolated from 5-week-old wild-type and Ptpn11$^{D61G/+}$ mice. Tissue lysates were subjected to immunoblotting with anti-Shp2, -pERK1/2, -total ERK1/2, -pAkt, and -Akt antibodies. The results represent densitometric analyses of the means±SEM for pERK1/2 and pAkt from 5 mice per genotype.

FIGS. 3A-3D show PZR tyrosyl phosphorylation in the heart and the cortex of $Ptpn11^{D61G/+}$ and $Ptpn11^{Y279C/+}$ mice. Using site-specific phospho-PZR antibodies we show that mice expressing a knockin mutation of the $Shp2^{D61G/+}$ allele exhibit increased PZR tyrosyl phosphorylation in the heart and cortex. Similarly, mice expressing a knockin mutation of the $Shp2^{Y279C/+}$ allele exhibit increased PZR tyrosyl phosphorylation in the heart and cortex. These results demonstrate that both NS and NSML mutations, with enhanced and reduced phosphatase catalytic activity, respectively are capable of increasing PZR tyrosyl phosphorylation. These results demonstrate that PZR is a target for both NS and NSML and suggest that PZR represents a novel common signaling component of these RASopthies. The results showed that PZR hypertyrosyl phosphorylation in the heart and cortex of NS and NSML model mice. These in vivo data confirmed the in silico (FIGS. 1A-1E) and in vitro (FIGS. 2A-2E) experiments FIGS. 4A-4C show images and graphs of PZR tyrosyl phosphorylation in $Ptpn11^{D61G/+}$ mice liver, kidney and spleen. PZR is hypertyrosyl phosphorylated in the liver, kidney and spleen of $Ptpn11^{D61G/+}$ mice. These results showed PZR hypertyrosyl phosphorylation in the various tissues of NS mice.

FIGS. 5A-5D show images of ERK and Akt phosphorylation in the heart and the cortex of $Ptpn11^{D61G/+}$ and $Ptpn11^{Y279C/+}$ mice. Phosphorylation status of ERK and AKT in the heart and cortex of $Ptpn11^{D61G/+}$ mice indicates no substantive differences to that of wild type despite under similar conditions PZR is hypertyrosyl phosphorylated (see FIGS. 3A-3D). These results implicated no apparent differences were observed in the basal levels of Shp2, phospho-ERK1/2, or phospho-Akt between either NS or NSML mice. These results further indicated that the effects of these RASopathies on MAPK and AKT signaling in the heart and cortex were distinct from those that drove PZR hyper tyrosyl phosphorylation.

Figure 6A:
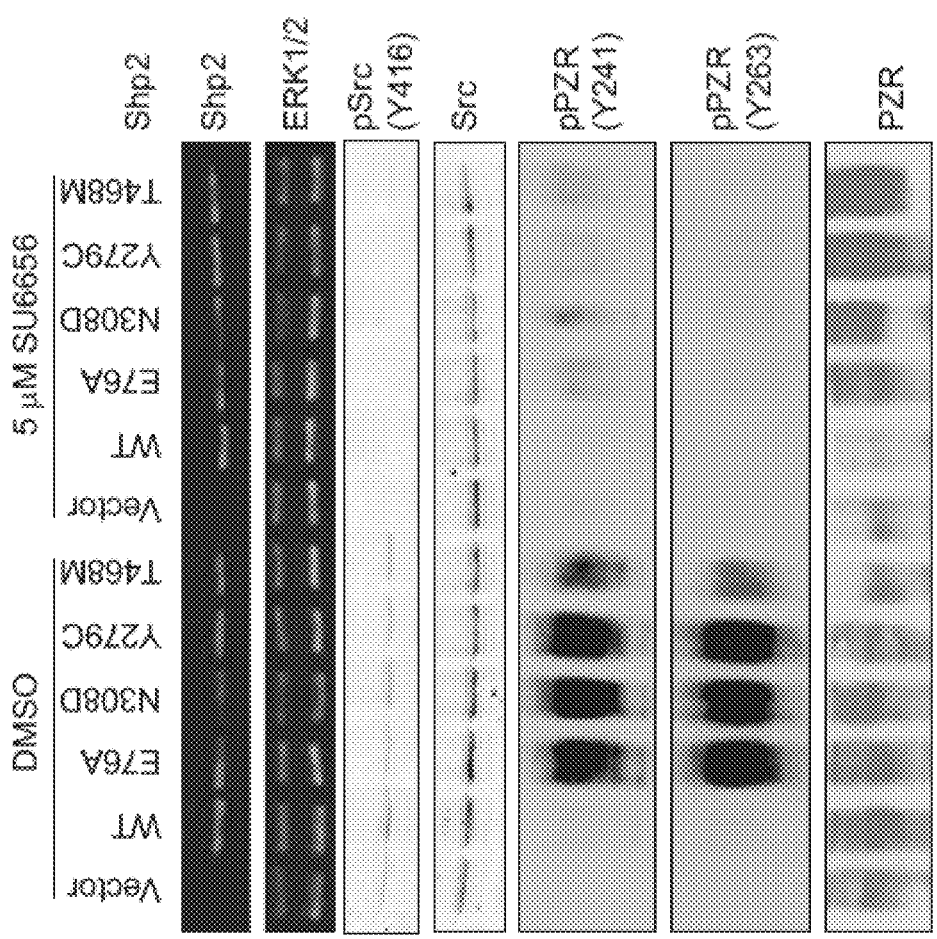
FIG. 6A is a panel of blots showing the effect of Src family kinases on PZR Y241 and Y263 phosphorylation. HEK-293 cells were transiently transfected with the indicated Shp2 mutants and treated with either dimethyl sulfoxide (DMSO) as a control or 5 µM SU6656. Cell lysates were immunoblotted with anti-Shp2, pSrc (Y416), Src, pPZR (Y241 or Y263), and total PZR antibodies. ERK1/2 was used as a loading control.
Figure 6B:
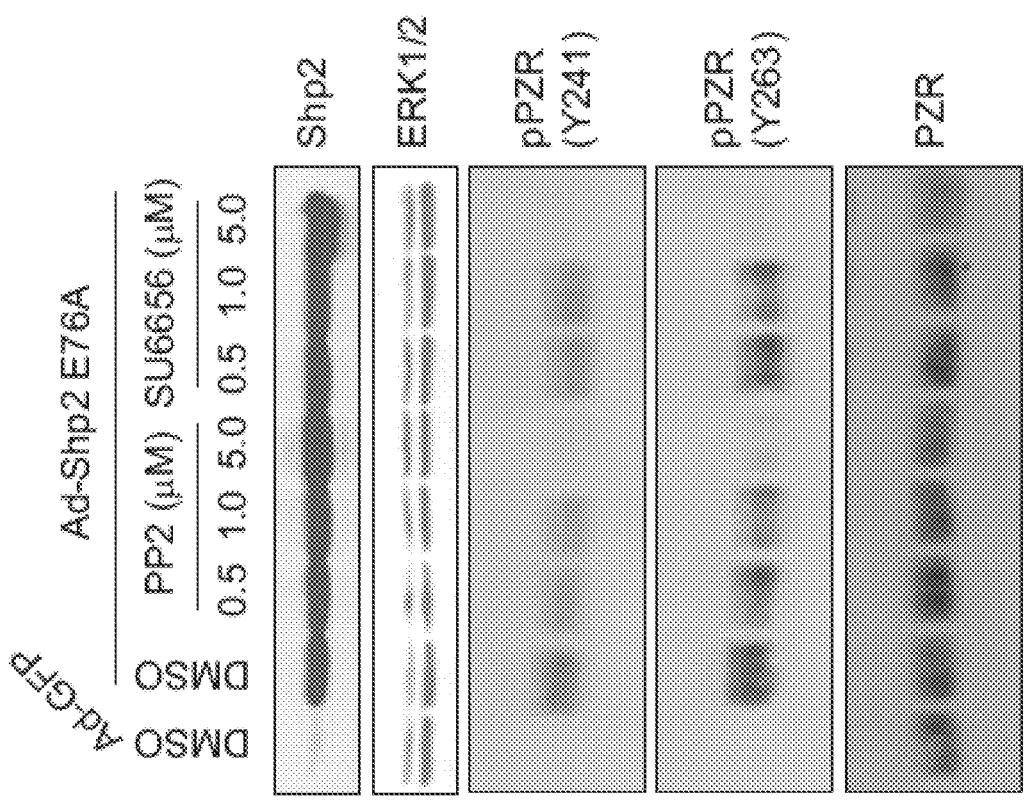
FIG. 6B is a panel of blots showing the effect of Src family kinases on PZR Y241 and Y263 phosphorylation. NIH 3T3 cells were infected with the adenoviruses expressing either GFP as a control or a constitutively active Shp2E76A, in the presence of DMSO, PP2, or SU6656 at the indicated concentration. Cell lysates were immunoblotted with anti-Shp2, pSrc (Y416), Src, pPZR (Y241 or Y263), and total PZR antibodies. ERK1/2 was used as a loading control.

FIGS. 6A-6B are blots showing the effect of Src family kinases on NS/NMLS-Shp2 mediated PZR Y241 and Y263 phosphorylation. NS and NMLS-associated mutants induce PZR hypertyrosyl which can be inhibited upon pre-treatment of cells with the SFK inhibitor SU6656. These results suggested that the SFK's were capable of phosphorylating PZR on both Y241 and Y263. These results further showed that NS and NSML-Shp2 mutants induced PZR hypertyrosyl phosphorylation is Src family kinase dependent.

Figures 7C, 7D:
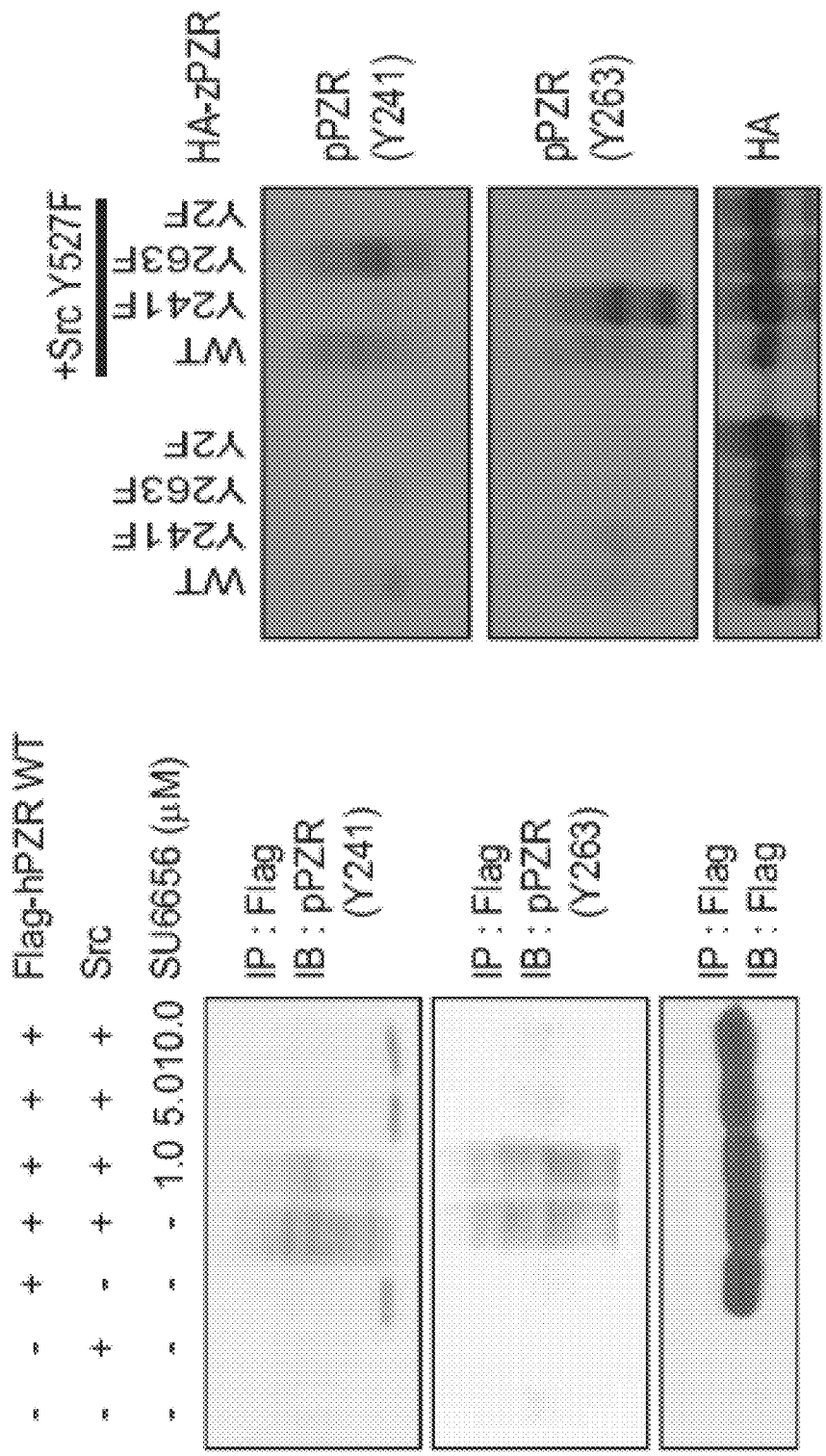
FIG. 7C is a blot showing that Src kinase induced PZR hyper-tyrosyl phosphorylation. HEK-293 cells were transfected with Flag-tagged human PZR. The cell lysates were immunoprecipitated with anti-Flag antibody. The immunoprecipitates were subjected to in vitro Src kinase assay with Src recombinant protein. The reaction products were immunoblotted with anti-pPZR (Y241 or Y263) antibodies.
FIG. 7D is a blot showing that Src family kinase induced PZR hyper-tyrosyl phosphorylation. HEK-293 cells were cotransfected with constitutively active Src mutant and either HA-tagged wild-type zebrafish PZR (WT), PZR mutated at tyrosine 236 (Y241F), tyrosine 258 (Y263F), or both (2YF). Cell lysates were immunoblotted with anti-pPZR (Y241 or Y263), and HA antibodies.

FIGS. 7A-7B are blots showing that Src kinase mediated NS/LS-Shp2 induced PZR hyper-tyrosyl phosphorylation. FIGS. 7C-7D are blots showing that Src kinase mediated PZR hyper-tyrosyl phosphorylation. The figures show the comparison of the effects of tyrosine kinase inhibitory potency on PZR tyrosyl phosphorylation. The tyrosine kinase inhibitors, PP2 and SU6656, were administered to cells expressing an activated Shp2 (Shp2-E76A) mutant. Although both PP2 and SU6656 were capable of inhibiting Shp2-E76A-induced PZR hypertyrosyl phosphorylation, SU6656 was more effective. PZR hyper tyrosyl phosphorylation was inhibited completely at 1 µM SU6656 as compared with PP2, which inhibited at 5 µM. These results supported the notion that the Src family kinases were responsible for the phosphorylation of PZR. Importantly, the phosphorylation of PZR by Src created a binding site (pY241/pY263) for Shp2 to interact with PZR. These results implicated c-Src as directly phosphorylating PZR at Shp2 binding sites.

In Noonan syndrome, the increased phosphorylation of Y241 and Y263 by Src resulted in deleteriously high levels of PZR/Shp2 complex which is proposed to be a mechanism that drives the development of congenital heart disease in these patients.

Figure 8B:
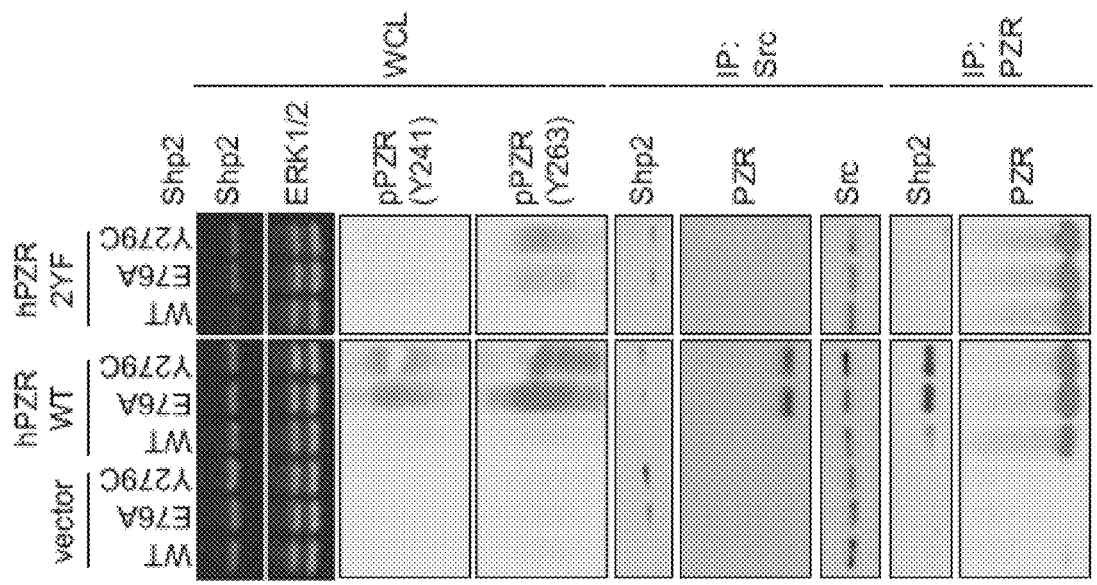
FIG. 8B is an image of a blot showing enhanced Src complex formation with NS/NSML-associated Shp2 mutants and PZR. HEK-293 cells were cotransfected with the Shp2 WT or E76A or Y279C mutant and either empty vector (vector), WT human PZR, or the PZR 2YF mutant.
Figure 8A:
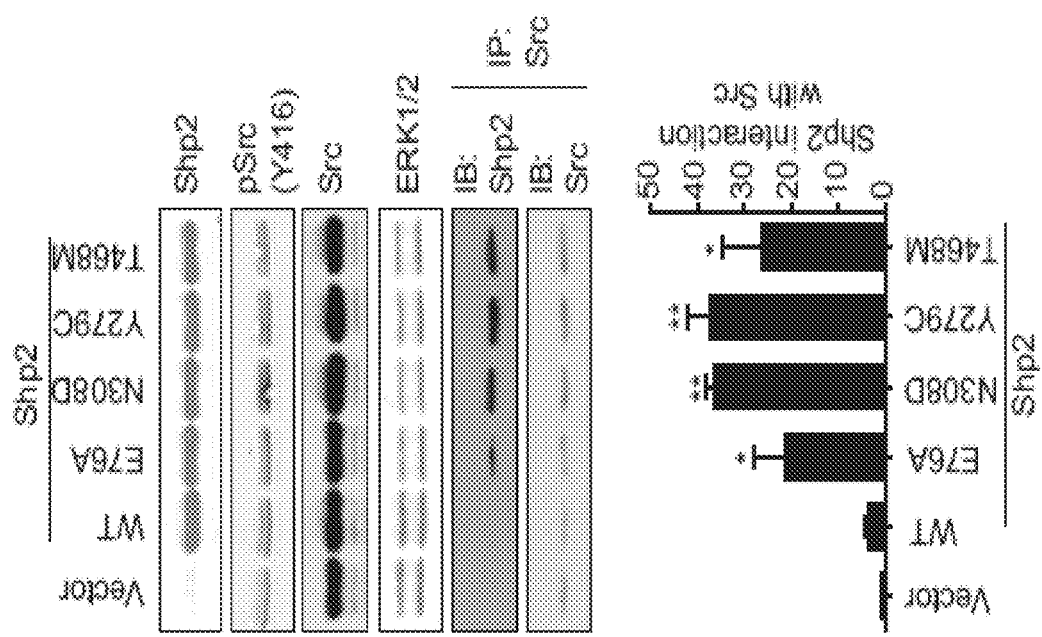
FIG. 8A is a blot and graph showing enhanced Src complex formation with NS/NSML-associated Shp2 mutants. HEK-293 cells were transiently transfected either with the Shp2 WT and the indicated Shp2 mutants. Cell lysates were immunoprecipitated (IP) with anti-c-Src antibodies, and immune complexes were immunoblotted (IB) with anti-Shp2 and -Src antibodies. The graph represents the means±SEM of the densitometric analysis from three independent experiments. Statistical significance was derived using a Dunnett's test comparing Shp2 mutants with the WT. *, P<0.05; **, P<0.01.

FIGS. 8A-8B show enhanced Src complex formation with NS/NSML-associated Shp2 mutants and PZR. FIG. 8A shows that mutant forms of Shp2 that are known to cause either NS or NSML can bind with increased affinity to c-Src as compared with wild type Shp2. These results further suggest that c-Src directly phosphorylated PZR at Shp2 binding sites.

FIG. 9 is an illustration of the model for the effects of NS- and NSML-Shp2 mutants on PZR tyrosyl phosphorylation. The model is based upon experimental data from which PZR was observed as hypertyrosyl phosphorylated on Shp2 binding sites in the heart of both NS and NSML mouse models. The increased PZR tyrosyl phosphorylation promoted increased Shp2 binding to PZR. The diagram proposes that enhanced PZR tyrosyl phosphorylation results in increase recruitment of Shp2 to PZR to promote further PZR tyrosyl phosphorylation, as well as other potential Src substrates that are in close proximity.

In addition, NS and NSML mutants interacted with the tyrosine kinase, Src, with increased affinity. Together, these promiscuous interactions resulted in dysfunctional downstream signaling from PZR which contributed to the development of congenital heart disease. It is proposed that by intervening with Src tyrosine kinase activity, PZR/Shp2 complexes are reduced and altered signaling from PZR, and possibly other targets, are corrected.

FIG. 10 is a panel of images showing dosing of dasatinib. Male Ptpn11D61G/+ mice were injected intrapertinoeally with dasatinib at the indicated dose or DMSO control. Twenty-four hours later, the mice were sacrificed and heart tissues were harvested and immunoblotted using total PZR and pY(263)-PZR antibodies. These results showed that injection of dasatinib in NS mice was effective at reducing PZR tyrosyl phosphorylation.

FIG. 11A is an illustration showing the pre-natal dosing regimen for dasatinib in NS mouse model. Dasatinib was administered daily to pregnant mothers between the time of when animals were in utero at E7.5 until 9 days after birth (P9). At 10 days after birth (P10), NS mice received dasatinib directly by daily injections (i.p.) for 6 weeks (P42) and 8 weeks (P56).

FIG. 11B is an illustration showing the post-natal dosing regimen for dasatinib in NS mouse model. Dasatinib was administered to NS mice starting at 10 days after birth (P10) daily for 6 weeks (P42) after 6 weeks treatment was stopped and heart function measured. This same group of mice was then evaluated after 2 weeks of being withdrawn from dasatinib treatment.

In FIGS. 11A and 11B, the mice were evaluated for cardiac function at 6 and 8 weeks. These illustrations described the pre- or post-natal Dasatinib treatment strategy into NS mice. The dosing regimens described herein were designed to test three aspects of the effectiveness of dasatinib for therapeutic intervention of NS-related cardiac disease. Because NS is a developmental disorder, the first dosing regimen shown in FIG. 11A tested the effectiveness of dasatinib in exerting a therapeutic effect when administered to the developing embryo. The second evaluation determined the effectiveness of dasatinib in treating NS-related cardiac disease when administered after birth. This strategy was linked more closely with cardiac disease outcomes as it has been realized that patients could be administered therapeutic doses of dasatinib after birth. This dosing strategy would mitigate risk of in utero complications. Finally, the third test was to establish that upon therapeutic cardiac function improvement, dasatinib administration was necessary to maintain treatment.

FIG. 12A is a panel of graphs showing dasatinib-treated pre-natally in NS mice improves cardiac function (P42, seen in FIG. 11A). FIG. 12B is a panel of graphs showing dasatinib-treated in post-natal NS mice improves cardiac function (P42). FIG. 12C is a panel of graphs showing preserved improvement of cardiac function after cessation of dasatinib treatment (P56, seen in FIG. 11B). These results provided evidence for the involvement of Src signaling in the pathogenesis of NS.

The results of these experiments demonstrated that a low dose of dasatinib—which is defined here as a dose that is below that found to be efficacious for the treatment of cancer—is effective in improving cardiac function in NS mice. In FIG. 12A, the results demonstrated that heart function, as measured by the ejection fraction (EF) and the fractional shortening (FS), were completely restored to wild type parameters when dasatinib was injected into pregnant mice. In FIG. 11B, dasatinib was shown to be effective even when administered post-developmentally. The treatment still exerted complete corrective functionality in cardiac function in NS mice. These results indicated that therapeutic administration of dasatinib for the treatment of congenital heart disease in RASopathy patients can occur with substantially less risk by post-development administration. Finally, FIG. 11C shows that cessation of dasatinib for 2 weeks after effective cardiac functionality has been achieved resulted in continued preservation of cardiac function. These results demonstrated that once effective therapy has been attained and heart functionality has returned, the need for continued exposure to dasatinib was unnecessary.

Example 2: Selective Rescue of Cardiac Defects in a Mouse Model of Noonan Syndrome (NS) by Dasatinib Shp2 is comprised of two Src homology 2 (SH2) domains, a protein tyrosine phosphatase (PTP) domain and a carboxy-terminal tail. NS-associated Shp2 (NS-Shp2) mutations often occur in amino acid residues that occupy the interface between the amino terminal SH2 and PTP domains. The resultant mutations disrupt the auto-inhibitory "closed" conformation that occurs between the SH2 and PTP domain, in favor of a more "open" configuration that facilitates catalysis.

The protein zero-related protein (PZR), a transmembrane glycoprotein which contains two immunoreceptor tyrosine-based inhibitory motifs (ITIMs) in its C-terminus, serves as a c-Src substrate and constitutes a major hyper-tyrosyl phosphorylated protein and Shp2 binding target in the heart of a mouse model of NS. NS-Shp2 mutants interact with enhanced affinity to c-Src endowing these mutants with the ability to promiscuously target c-Src through PZR complex formation. Using zebrafish as a model of NS-mediated CHD, it was proposed that PZR-Shp2-Src complex formation drives aberrant signaling in NS-mediated CHD.

Critical to this supposition is the ability of NS-Shp2 mutants to exhibit enhanced interactions with c-Src leading to increased c-Src-mediated signaling. The nature of the enhanced interaction between Shp2 and c-Src likely occurs as a result of increased exposure of binding surfaces within the PTP domain of Shp2 that are otherwise unexposed in the "closed" conformation. Although Shp2 has been shown to form a complex with c-Src through its SH3 domain, the region on Shp2 that c-Src interacts with is not yet defined.

To address this, a series of Shp2 deletion mutants were designed (FIG. 13a), co-transfected into HEK-293T cells, and complex formation was examined by co-immunoprecipitation (FIG. 23). As expected, full-length Shp2 was detected in a complex with c-Src, whereas a deletion mutant of Shp2 lacking the PTP domain failed to interact (FIG. 13b). In vitro binding assays further established that the PTP domain of Shp2 and the SH3 domain of c-Src interacted directly (FIG. 13c).

Since this interaction occurs within the PTP domain of Shp2, the "open" conformation of NS-Shp2 mutants are thought to be poised to establish more stable interactions with the SH3 domain of c-Src as compared with wild type Shp2. As such, NS-Shp2 mutants complex more stably with c-Src at the membrane through PZR, which has been proposed previously to be a putative mechanism of aberrant c-Src-mediated signaling. Importantly, these observations implicate c-Src, or a Src family kinase (SFK) member, as a candidate(s) in Shp2-mediated NS pathogenesis.

To test whether the SFKs are involved in NS pathogenesis, c-Src was inhibited pharmacologically in order to test whether its inhibition ameliorates Shp2-NS signaling. To inhibit c-Src dasatinib (SPRYCEL©), a dual Abl-Src kinase inhibitor, approved for the treatment of chronic myeloid leukemia, was used. Treatment of mouse embryonic fibroblasts (MEFs) isolated from NS mice with dasatinib blocked c-Src, ERK1/2 and PZR tyrosyl phosphorylation (FIGS. 13d-13h and 24).

Inhibition of PZR tyrosyl phosphorylation by dasatinib also resulted in disruption of PZR/Shp2 complex formation (FIG. 13d). Additionally, Raf-1, MEK1, JNK and Akt were inhibited in NS-derived MEFs by dasatinib (FIG. 17).

The BCR-Abl kinase inhibitor, STI-571 (Gleevec©), was ineffective at impairing PZR tyrosyl phosphorylation, indicating that inhibition of PZR tyrosyl phosphorylation and disruption of the PZR/Shp2 complex was likely a result of dasatinib's effect on c-Src rather than Abl (FIG. 17). Moreover, an Shp2 inhibitor did not block NS-Shp2-mediated PZR hypertyrosyl phosphorylation (FIG. 17), indicating that NS-Shp2-mediated c-Src PZR tyrosyl phosphorylation occurred independently of Shp2's phosphatase activity.

To examine the effects of dasatinib on NS-mediated c-Src and PZR tyrosyl phosphorylation in vivo, dasatinib was injected into mice containing a knockin mutation of Shp2 at Asp61 to Gly61 (D61G) (Araki et al Nat Med 10, 849-857 (2004)). Mice heterozygous for PtpN11$^{D61G/+}$, referred to herein as "NS mice," recapitulate many features of the human disease, including short stature, craniofacial abnormalities, myeloproliferative disease and CHD.

Dasatinib has been shown to be effective in preventing tumor incidence in mice at a dosage of ~20 mg/kg (Shah et al., Science 305, 399-401(2004)). The therapeutic effects of dasatinib in humans is reported to be ~2 mg/kg, an equivalent dose of ~24 mg/kg, in mice (Kantarjian et al., N Engl J Med 362, 2260-2270 (2010), Yu et al., Clinical Cancer Research 15, 7421-7428 (2009), Apperley J Clin Oncol 27, 3472-3479 (2009)). Doses of dasatinib as low as 0.5 mg/kg were sufficient to significantly inhibit both c-Src and PZR tyrosyl phosphorylation in the heart of 3-week-old NS mice (FIGS. 13i-13l). Notably, at these doses of dasatinib (0.1-0.5 mg/kg), neither ERK1/2 phosphorylation (FIGS. 13i-13l), Raf-1, MEK1, p38 MAPK, nor JNK were affected in the heart of 3-week-old NS mice (FIG. 18). These results indicate that dasatinib, at up to 250-fold lower doses than the effective chemotherapeutic doses (for chronic myelogous leukemia adult patient approx. 100-140 mg/day or approx. 1.4-2.0 mg/kg/day), can inhibit PZR tyrosyl phosphorylation in the heart of NS mice.

Moreover, in the hearts of NS mice, dasatinib-mediated inhibition of PZR tyrosyl phosphorylation was uncoupled from the inhibition of ERK1/2 phosphorylation (FIG. 13). Hence, low doses of dasatinib interfered with NS-Shp2 signaling independently of the ERK1/2 pathway.

Dasatinib was administered into pregnant mothers and amelioration of cardiac defects in NS mice was assessed. Dasatinib was administered at 0.1, 0.5 or 1.0 mg/kg daily interperitoneally into wild type pregnant mice intercrossed with NS mice, beginning at embryonic day 7 until postnatal day 9 (in nursing females). After postnatal day 10 (P10), dasatinib injections resumed directly into individual pups daily until 8-weeks (P56) after birth (FIG. 14a). Although dasatinib treatment at 0.5 and 1.0 mg/kg/per day showed embryonic lethality, dasatinib treatment at 0.1 mg/kg/per day had no observable adverse effects (Table 1).

Cardiac function of NS mice was examined at 6- and 8-weeks by echocardiography and invasive hemodynamics. The ejection fraction (EF) and fractional shortening (FS) in untreated NS mice was significantly reduced by 35% (P<0.01) as compared with vehicle-treated wild type mice. However, dasatinib-treated NS mice at P42 exhibited complete restoration of cardiac function as compared with vehicle-treated NS mice (FIGS. 14b and 14c and Table 2). However, continued administration of dasatinib for an additional 2 weeks induced cardiac failure in both wild type and dasatinib-treated NS mice (FIGS. 14d-14e and Table 3). These data suggest that dasatinib treatment in utero can rescue the impaired cardiac function observed in NS mice. Thus, c-Src activity contributes to the manifestation of Shp2-NS CHD.

TABLE 1

Progeny from prenatal dasatinib treated Ptpn11$^{D61G/+}$ X WT breeder.

|  | Ptpn11$^{+/+}$ | ptpn11$^{D61G/+}$ | Dead pups |
| --- | --- | --- | --- |
| Vehicle | 21 | 20 |  |
| Dasatinib (0.1 mg/kg) | 25 | 19 | 4 |

TABLE 2

Echocardiography parameters of prenatal vehicle- or dasatinib-treated WT and Ptpn11D$^{61G/+}$ mice at P42.

|  | Vehicle | | Dasantinib | |
| --- | --- | --- | --- | --- |
|  | WT (n = 8) | D61G/+ (n = 8) | WT (n = 8) | D61G/+ (n = 8) |
| IVS, d (mm) | 0.69 ± 0.06 | 0.57 ± 0.03 | 0.67 ± 0.04 | 0.65 ± 0.06 |
| IVS, s (mm) | 1.10 ± 0.06 | 1.01 ± 0.06 | 1.08 ± 0.09 | 0.97 ± 0.10 |
| LVID, d (mm) | 3.95 ± 0.15 | 3.55 ± 0.10 | 3.93 ± 0.08 | 3.61 ± 0.12 |
| LVID, s (mm) | 2.45 ± 0.19 | 3.01 ± 0.07** | 2.49 ± 0.09 | 2.32 ± 0.12†† |
| LVPW, d (mm) | 0.74 ± 0.03 | 0.78 ± 0.02 | 0.76 ± 0.05 | 0.70 ± 0.04 |
| LVPW, s (mm) | 1.23 ± 0.08 | 0.97 ± 0.06* | 1.13 ± 0.04 | 1.12 ± 0.07 |
| LV vol, d (mm$^3$) | 68.02 ± 4.23 | 55.82 ± 2.96 | 67.51 ± 2.54 | 60.93 ± 3.75 |
| LV vol, s (mm$^3$) | 20.15 ± 3.15 | 30.65 ± 1.18** | 22.26 ± 1.95 | 24.21 ± 1.56 |
| % EF | 66.84 ± 1.43 | 43.30 ± 3.38** | 64.24 ± 2.52 | 62.62 ± 2.75†† |
| % FS | 36.22 ± 1.21 | 25.84 ± 3.01** | 34.70 ± 1.82 | 34.29 ± 2.09†† |

Data represents the Mean ± SEM.
*p < 0.05;
**p < 0.01 denotes significance compared with the vehicle treated WT mice.
††p < 0.01 denotes significance compared with the vehicle treated Ptpn11$^{D61G/+}$ mice. All p values were derived using 2-way ANOVA (Tukey multiple comparison).
IVS, Intraventricular septum wall thickness;
LVID, left ventricular internal dimension;
LVPW, left ventricular posterior wall thickness;
LV vol, left ventricle volume;
EF, ejection fraction;
FS, fractional shortening;
d, diatole;
s, systole.

TABLE 3

Echocardiography parameters of prenatal vehicle- or dasatinib-treated WT and Ptpn11D$^{61G/+}$ mice at P56.

|  | Vehicle | | Dasantinib | |
| --- | --- | --- | --- | --- |
|  | WT (n = 8) | D61G/+ (n = 8) | WT (n = 8) | D61G/+ (n = 8) |
| IVS, d (mm) | 0.71 ± 0.03 | 0.72 ± 0.05 | 0.69 ± 0.04 | 0.70 ± 0.03 |
| IVS, s (mm) | 1.21 ± 0.10 | 1.04 ± 0.04 | 1.07 ± 0.05 | 1.02 ± 0.05 |
| LVID, d (mm) | 3.83 ± 0.09 | 3.85 ± 0.11 | 4.21 ± 0.07* | 4.06 ± 0.11 |
| LVID, s (mm) | 2.42 ± 0.07 | 2.92 ± 0.10*** | 3.04 ± 0.10*** | 3.08 ± 0.07 |
| LVPW, d (mm) | 0.80 ± 0.02 | 0.78 ± 0.04 | 0.71 ± 0.04 | 0.68 ± 0.02 |
| LVPW, s (mm) | 1.25 ± 0.04 | 0.95 ± 0.05*** | 0.95 ± 0.05*** | 0.93 ± 0.06 |
| LV vol, d (mm$^3$) | 67.13 ± 3.87 | 69.58 ± 5.82 | 79.32 ± 1.22 | 73.00 ± 3.42 |
| LV vol, s (mm$^3$) | 19.76 ± 1.25 | 31.76 ± 2.73*** | 40.34 ± 1.60*** | 37.43 ± 2.08 |
| % EF | 70.35 ± 1.23 | 49.79 ± 2.37*** | 50.96 ± 2.38*** | 51.83 ± 1.60 |
| % FS | 39.98 ± 1.26 | 26.53 ± 1.30*** | 25.84 ± 1.47*** | 26.22 ± 1.01 |

Data represents the Mean ± SEM.
*p < 0.05;
***p < 0.001 denotes significance compared with the vehicle treated WT mice. All p values were derived using 2-way ANOVA (Tukey multiple comparison).
IVS, Intraventricular septum wall thickness;
LVID, left ventricular internal dimension;
LVPW, left ventricular posterior wall thickness;
LV vol, left ventricle volume;
EF, ejection fraction;
FS, fractional shortening;
d, diatole;
s, systole.

Dasatinib was effective in curtailing NS-Shp2 effects on CHD post-developmentally. NS mice were treated with dasatinib (0.1 mg/kg/day) from P10 until P42 (FIG. 14f). In addition to the presentation of CHD, NS humans and mice show growth retardation, facial dimorphism and splenomegaly similar to that of the human disease. Although NS mice were found to exhibit reduced growth, facial dimorphism and splenomegaly, dasatinib treatment did not improve any of these NS-related pathologies (FIGS. 19-21). Moreover, no evidence of liver damage was detected in either wild type or NS mice treated with dasatinib (FIG. 22).

However, upon examination of cardiac parameters, dasatinib-treated NS mice (P42) had completely restored cardiac functionality as determined by measures of EF and FS (FIGS. 14g and 14h and Tables 4-5). Remarkably, when cardiac function was assessed in NS mice at a later timepoint, after which dasatinib treatment had been discontinued for 2 weeks, similar levels of cardiac functional improvements as compared with vehicle-treated wild type controls was observed (FIGS. 14i and 14j). Additional cardiac parameters were also assessed by invasive hemodynamics and these results showed that aortic blood pressure and left ventricular pressure were significantly restored in dasatinib-treated NS mice (FIGS. 14k-14n and Table 6).

Taken together, these data demonstrate that dasatinib, when administered to NS mice post-developmentally at a dose that is sub-therapeutic for its use as a treatment of CML, provides selective efficacy for preventing cardiac failure in NS mice. Interestingly, the improvement in cardiac function does not appear to be transient, since removal of dasatinib did not reverse the restoration of cardiac function in NS mice.

TABLE 4

Echocardiography parameters of postnatal vehicle- or dasatinib-treated WT and Ptpn11D$^{61G/+}$ mice at P42.

|  | Vehicle | | Dasantinib | |
| --- | --- | --- | --- | --- |
|  | WT (n = 7) | D61G/+ (n = 6) | WT (n = 6) | D61G/+ (n = 6) |
| IVS, d (mm) | 0.65 ± 0.06 | 0.54 ± 0.04 | 0.71 ± 0.05 | 0.66 ± 0.05 |
| IVS, s (mm) | 1.06 ± 0.06 | 1.02 ± 0.09 | 1.13 ± 0.06 | 1.04 ± 0.07 |
| LVID, d (mm) | 3.83 ± 0.17 | 3.55 ± 0.13 | 3.80 ± 0.11 | 3.63 ± 0.07 |
| LVID, s (mm) | 2.36 ± 0.18 | 2.96 ± 0.07** | 2.45 ± 0.05 | 2.50 ± 0.08† |
| LVPW, d (mm) | 0.72 ± 0.03 | 0.77 ± 0.02 | 0.81 ± 0.04 | 0.71 ± 0.03 |
| LVPW, s (mm) | 1.19 ± 0.07 | 0.95 ± 0.05* | 1.25 ± 0.07 | 1.09 ± 0.06 |
| LV vol, d (mm$^3$) | 68.43 ± 6.10 | 56.10 ± 4.28 | 65.87 ± 2.78 | 57.35 ± 2.19 |
| LV vol, s (mm$^3$) | 20.15 ± 3.73 | 30.90 ± 1.73** | 22.24 ± 0.63 | 24.67 ± 1.18 |
| % EF | 65.11 ± 2.42 | 46.44 ± 5.16** | 65.70 ± 0.82 | 60.93 ± 2.06† |
| % FS | 35.04 ± 1.69 | 24.39 ± 2.92** | 35.52 ± 0.69 | 33.08 ± 1.33† |

Data represents the Mean ± SEM.
*p < 0.05;
**p < 0.01 denotes significance compared with the vehicle treated WT mice.
†p < 0.05 denotes significance compared with the vehicle treated Ptpn11$^{D61G/+}$ mice. All p values were derived using 2-way ANOVA (Tukey multiple comparison).
IVS, Intraventricular septum wall thickness;
LVID, left ventricular internal dimension;
LVPW, left ventricular posterior wall thickness;
LV vol, left ventricle volume;
EF, ejection fraction;
FS, fractional shortening;
d, diatole;
s, systole.

TABLE 5

Echocardiography parameters of postnatal vehicle- or dasatinib-treated WT and Ptpn11D$^{61G/+}$ mice at P56.

|  | Vehicle | | Dasantinib | |
| --- | --- | --- | --- | --- |
|  | WT (n = 9) | D61G/+ (n = 9) | WT (n = 6) | D61G/+ (n = 6) |
| IVS, d (mm) | 0.71 ± 0.03 | 0.69 ± 0.05 | 0.69 ± 0.03 | 0.72 ± 0.04 |
| IVS, s (mm) | 1.17 ± 0.10 | 1.01 ± 0.04 | 1.19 ± 0.06 | 1.18 ± 0.05 |
| LVID, d (mm) | 3.86 ± 0.08 | 3.86 ± 0.10 | 3.92 ± 0.09 | 3.93 ± 0.08 |
| LVID, s (mm) | 2.43 ± 0.06 | 2.95 ± 0.10*** | 2.52 ± 0.10 | 2.60 ± 0.07† |
| LVPW, d (mm) | 0.78 ± 0.02 | 0.77 ± 0.04 | 0.80 ± 0.06 | 0.65 ± 0.03 |
| LVPW, s (mm) | 1.22 ± 0.05 | 0.96 ± 0.04*** | 1.18 ± 0.05 | 1.19 ± 0.05† |
| LV vol, d (mm$^3$) | 69.38 ± 3.40 | 69.22 ± 5.22 | 64.06 ± 2.65 | 65.60 ± 2.44 |
| LV vol, s (mm$^3$) | 20.21 ± 1.05 | 32.80 ± 2.76*** | 23.06 ± 2.21 | 24.85 ± 1.68† |
| % EF | 68.72 ± 2.09 | 50.92 ± 2.50*** | 65.89 ± 1.74 | 64.71 ± 1.67††† |
| % FS | 39.31 ± 1.13 | 25.64 ± 1.53*** | 36.63 ± 1.20 | 34.92 ± 1.23††† |

Data represents the Mean ± SEM.
***p < 0.001 denotes significance compared with the vehicle treated WT mice.
†p < 0.05;
†††p < 0.001 denotes significance compared with the vehicle treated Ptpn11$^{D61G/+}$ mice. All p values were derived using 2-way ANOVA (Tukey multiple comparison).
IVS, Intraventricular septum wall thickness;
LVID, left ventricular internal dimension;
LVPW, left ventricular posterior wall thickness;
LV vol, left ventricle volume;
EF, ejection fraction;
FS, fractional shortening;
d, diatole;
s, systole.

TABLE 6

Hemodynamic analysis parameters of postnatal vehicle- or dasatinib-treated WT and Ptpn11D$^{61G/+}$ mice at P56.

|  | Vehicle | | Dasantinib | |
| --- | --- | --- | --- | --- |
|  | WT (n = 8) | D61G/+ (n = 9) | WT (n = 8) | D61G/+ (n = 9) |
| Systolic pressure (mmHg) | 1.42 ± 9.3 | 102.8 ± 3.1*** | 146.2 ± 5.1 | 129.3 ± 6.2† |
| Diastolic pressure (mmHg) | 89.1 ± 5.0 | 61.8 ± 2.2*** | 95.1 ± 4.2 | 84.0 ± 3.5†† |
| Pulse pressure (mmHg) | 67.2 ± 5.3 | 53.0 ± 1.5 | 65.2 ± 4.6 | 63.7 ± 4.4 |
| Mean areterial pressure (mmHg) | 106.8 ± 6.3 | 75.5 ± 2.4*** | 112.1 ± 4.0 | 96.8 ± 4.2†† |
| Left ventricle pressure (mmHg) | 137.9 ± 8.0 | 105.6 ± 3.6** | 1.36 ± 2.5 | 127.9 ± 4.5† |
| End diastolic pressure (mmHg) | 7.8 ± 1.8 | 10.5 ± 0.9 | 8.7 ± 1.3 | 11.1 ± 0.7 |
| +dP/dt (mmHg/s) | 8497 ± 556 | 5850 ± 282** | 8626 ± 476 | 7718 ± 498† |
| −dP/dt (mmHg/s) | −6075 ± 235 | −5354 ± 538 | −6529 ± 847 | −6189 ± 6.26 |

Data represents the Mean ± SEM.
**$p < 0.01$;
***$p < 0.001$ denotes significance compared with the vehicle treated WT mice.
†$p < 0.05$;
††$p < 0.01$ denotes significance compared with the vehicle treated Ptpn11$^{D61G/+}$ mice. All p values were derived using 2-way ANOVA (Tukey multiple comparison).

To provide further insight into the nature of the cardiac phenotype exhibited in dasatinib-treated NS mice, gross morphological and histological examination of these hearts was undertaken. NS mice have lower heart weights as compared with wild type mice (FIG. 15a). Heart weight to body weight ratios were significantly increased in NS mice (FIG. 15b). Histological analysis also revealed that NS mice had dilated cardiomyopathy (DCM), shown by significantly reduced left ventricular septum wall thickness and increased left ventricular chamber dimension in systole (FIG. 15c and Table 4).

As expected, histological examination of cardiac tissue revealed disorganized myofibrillar structures in the left ventricle wall of vehicle-treated NS mice (FIG. 15d). In contrast, dasatinib-treated NS mice showed a profound reversal of all of these pathologic cardiac phenotypes to levels that were essentially similar to that of vehicle-treated wild type mice (FIGS. 15a-15d).

Another hallmark of the failing heart is the acquisition of cardiac fibrosis. Consistent with the notion that dasatinib treatment conferred protection against cardiac failure in the NS heart, fibrosis in dasatinib-treated NS mouse hearts was markedly reduced as compared with vehicle-treated wild type mice at the histological level consistent with the reduced mRNA expression levels of fibrotic genes Col1a2 and Col3a1 (FIGS. 15d-15f). The deposition of fibrotic components, such as collagens, encoded for by Col1a2 and Col3a1 genes, is associated with heart failure. Therefore, the reduction in the expression of Col1a2 and Col3a1 is consistent with the correction of heart failure by low-dose dasatinib treatment.

The re-expression of cardiac structural proteins, such as αMyosin Heavy Chain (MYH6) and βMyosin Heavy Chain (MYH7) genes, is indicative of cardiomyopathy. In particular, inactivation of MYH6 and activation of MYH7 represent features of cardiac reprogramming that support the development of cardiomyopathy (Morita et al., *J Clin Invest* 115 (2005)). MYH6 expression was significantly downregulated in vehicle-treated NS mice as compared with wild type mice. Dasatinib treatment resulted in an equivalent level of MYH6 expression in wild type and NS mice (FIG. 15g). MYH7 was prominently re-expressed in vehicle-treated NS mice and this was completely normalized back to vehicle wild-type treated levels following dasatinib treatment (FIG. 15h).

The effects of dasatinib to ameliorate cardiac failure in NS mice was further bolstered by the assessment of Atrial naturietic peptide (Anp) and Brain natriuetic peptide (Bnp). Both Anp and Bnp mRNA expression levels were significantly upregulated in NS mice as compared with vehicle-treated wild type controls (FIGS. 15i and 15j). In contrast, dasatinib-treated NS mice were completely rescued from the elevated mRNA expression levels of both Anp and Bnp (FIGS. 15i and 15j). Collectively, these results support the conclusion that Src family kinase activity plays an integral role in the development of NS-associated CHD.

In order to determine whether the effects of dasatinib on NS cardiac function were intrinsic to the myocardium, calcium ($Ca^{2+}$) mediated force dynamics were measured in isolated cardiomyocytes from vehicle- and dasatinib-treated wild type and NS mice. Isolated cardiomyocytes were characterized simultaneously for $Ca^{2+}$ handling and contraction kinetics under electrical pacing. Relative calcium release ($R_{mag}$ $Ca^{2+}$) was 55% higher in NS cardiomyocytes compared with wild type cardiomyocytes and this difference was substantially ameliorated in dasatinib-treated NS mice (FIGS. 16a and 16b).

Cardiomyoctyes from vehicle-treated NS mice showed deficits in contractility, with peak shortening that was 22% smaller than vehicle-treated wild type mice (FIGS. 16a and 16c). This result is striking in light of the highly significant increase in $Ca^{2+}$ release observed in these same cardiomyoctyes relative to wild type, and suggests a reduction in myofilament $Ca^{2+}$ sensitivity in vehicle-treated NS cells. However, the fractional shortening of sarcomeres in NS cardiomyocytes was significantly impaired and was 22% lower than that in wild type cardiomyocytes (FIGS. 16a-16c and Table 7). Importantly, these differences were completely restored in cardiomyocytes isolated from dasatinib-treated NS mice (FIGS. 16a-16c and Table 7).

The molecular mechanism for the changes in calcium handling and contractility was investigated by immunoblotting for the sarco(endo)plasmic reticulum $Ca^{2+}$-ATPase 2 (SERCA2A). In the myocardium, SERCA2A is the predominant isoform responsible for calcium delivery to the contractile machinery. A hallmark of heart failure is reduced SERCA2A expression, which compromises the delivery $Ca^{2+}$ to contractile proteins thus reducing contraction force.

Strikingly, vehicle-treated NS mice hearts showed significantly decreased SERCA2A protein expression and increased TnI and TnT expression compared with wild type (FIGS. 16d-16g). Consistent with the restoration of cardiac function in dasatinib-treated NS mice, cardiac tissue isolated from dasatinib-treated NS mice exhibited a completely normalized level of SERCA2A expression (FIGS. 16d and 16e).

The ongoing remodeling that occurs during heart failure as a result of compensatory mechanisms to preserve contractility results in the upregulation of contractile proteins, Troponin T (TnT) and Troponin I (TnI). Both TnT and TnI were significantly elevated in vehicle-treated NS mice as compared with vehicle-treated wild type mice (FIGS. 16d, 16f and 16g). Dasatinib-treated NS mice showed a complete reversal of the failing heart phenotype since both TnT and TnI expression levels returned to those equivalent to vehicle-treated wild type mice (FIGS. 16d, 16f and 16g). Collectively, these findings clearly demonstrate that post-developmental treatment with dasatinib to a NS mouse model alleviates the contractile dysfunction of the myocardium.

binding protein and SFK substrate. PZR hyper tyrosyl phosphorylation is a direct result of enhanced NS-mediated Src signaling. These data suggest that c-Src functions in the propagation of NS-related CHD.

The data presented in FIGS. 25a-25f represents dasatinib treatment starting at post-natal day 10 (P10) for 6 weeks (P42) in wild type (WT) and NSML (Ptpn11$^{Y279C/+}$) mice. Ptpn11$^{Y279C/+}$ were obtained from Dr. Kontaridis (Beth Israel Deaconess Hospital, Boston, Mass.) and bred as described (Marin, et al, J Clin. Invest., 121:1026-1043 (2011)). Mice were treated with either vehicle or dasatinib at a dose of 0.1 mg/kg/day for 6 weeks after which dasatinib treatment was discontinued and mice sacrificed two weeks later. At the completion of the study, wild type and Ptpn11$^{Y279C/+}$ mice were sacrificed and total RNA from the hearts was isolated and qPCR was performed for the detection of mRNA expression for genes involved in the development of cardiomyopathy, Myh6 and Myh7 and the development of cardiac fibrosis, col1a2 and Col3a1.

Figures 25A, 25B, 25C, 25D, 25E, 25F:
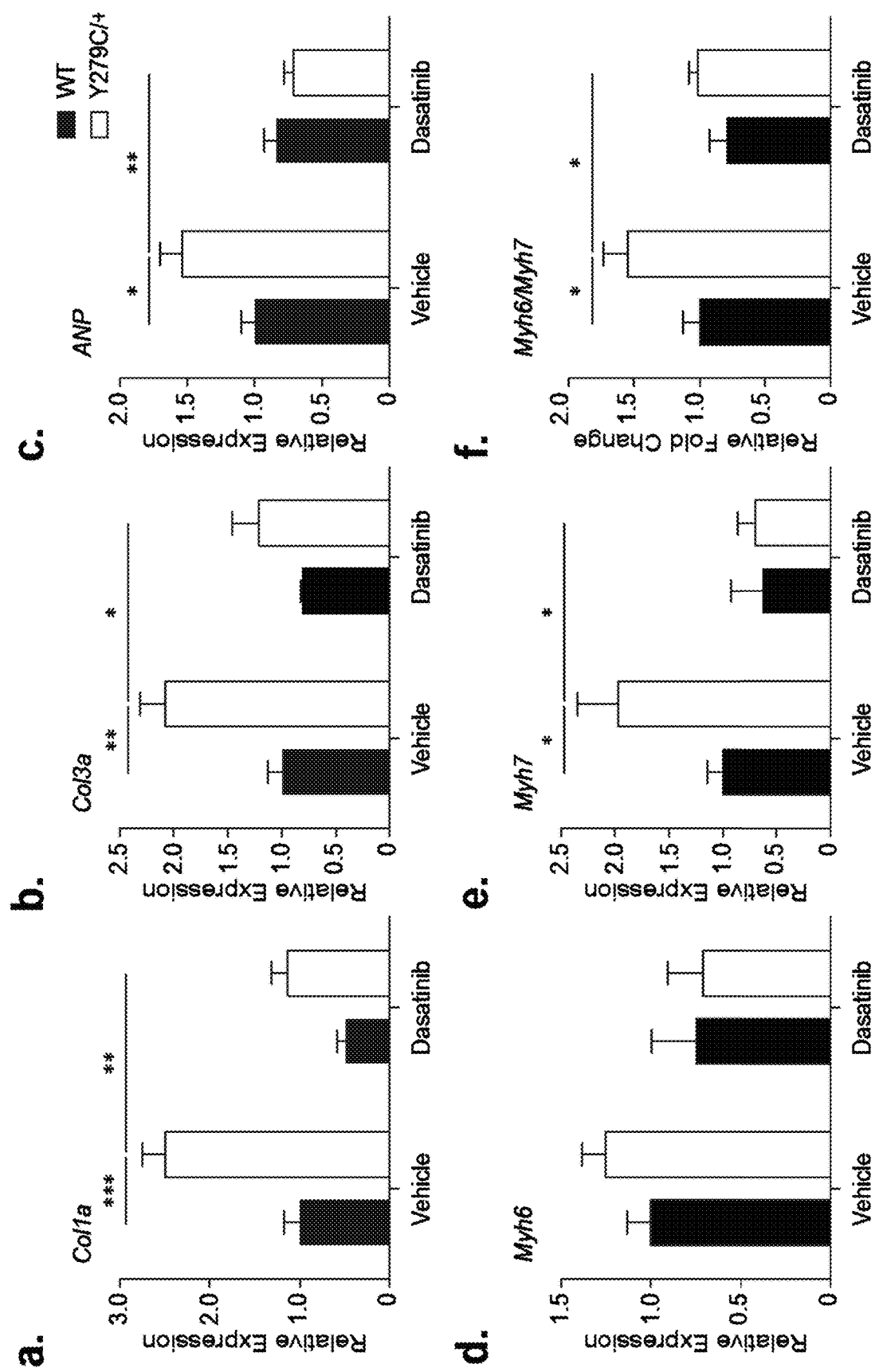

As shown, vehicle-treated Ptpn11$^{Y279C/+}$ mice, by 6 weeks of age, already began to show signs of tissue cardiomyopathy as evidenced by increased expression of ANP, Myh6 and Myh7 (FIGS. 25d and 25e). In addition, there was an accompanying increase in cardiac fibrosis in Ptpn11$^{Y279C/+}$ mice as compared with vehicle-treated-wild type mice (FIGS. 25a and 25b). However, dasatinib-treated Ptpn11$^{Y279C/+}$ mice showed complete restoration back to wild type levels of expression of ANP, Myh6 and Myh7. Significantly, the ratio of Myh6 Myh7, which represents the

TABLE 7

Ca2+ excitation-contraction coupling parameters of cardiomyocytes isolated from the heart of postnatal vehicle- or dasatinib-treated WT and Ptpn11D$^{61G/+}$ mice at P56.

| | Vehicle | | Dasatinib | |
|---|---|---|---|---|
| | WT (n = 131 cell, n = 3 mice) | D61G/+ (n = 128 cells, N = 3 mice) | WT (n = 111 cells, n = 3 mice) | D61G/+ (n = 162 cells, n = 3 mice) |
| Diastolic $Ca^{2+}$ (Min$_{F340/380}$) | 1.05 ± 0.01 | 1.00 ± 0.01*** | 0.94 ± 0.01*** | 0.98 ± 0.01 |
| Systolic $CA^{2+}$ (Max F$_{340/380}$) | 1.21 ± 0.01 | 1.24 ± 0.01 | 1.06 ± 0.01*** | 1.12 ± 0.01††† |
| R$_{mag}$ $Ca^{2+}$ (ΔF$_{340/380}$) | 0.16 ± 0.01 | 0.25 ± 0.01*** | 0.11 ± 0.01*** | 0.14 ± 0.01††† |
| $Ca^{2+}$ TTP (ms, F$_{340/380}$) | 42.99 ± 0.95 | 40.41 ± 0.76 | 42.75 ± 1.21 | 43.22 ± 0.90 |
| Tau $Ca^{2+}$ (ms) | 109.18 ± 2.67 | 123.13 ± 1.88*** | 105.85 ± 2.35 | 116.52 ± 2.36 |
| Peak Shortening (%) | 5.22 ± 0.19 | 4.09 ± 0.20*** | 6.04 ± 0.23* | 6.59 ± 0.18††† |
| Shortening TTP (ms) | 64.45 ± 0.82 | 67.75 ± 0.97* | 71.52 ± 0.90*** | 69.32 ± 0.79 |
| Shortening RT50 (ms) | 35.20 ± 0.70 | 38.74 ± 1.03* | 41.11 ± 0.96*** | 37.02 ± 0.62† |
| Shortening RT90 (ms) | 96.47 ± 3.60 | 112.16 ± 4.35* | 113.38 ± 4.18* | 99.24 ± 3.23 |

Data represents the Mean ± SEM.
*p < 0.05;
***p < 0.001 denotes significance compared with the vehicle treated WT cardiomyocytes.
†p < 0.05;
†††p < 0.001 denotes significance compared with the vehicle treated Ptpn11$^{D61G/+}$ cardiomyocytes. All p values were derived using 2-way ANOVA (Tukey multiple comparison).
TTP, Time to peak;
RT50, Time from peak tension to 50% relaxation;
RT90, Time from peak tension to 90% relaxation.

Previously, it was determined that the transmembrane glycoprotein PZR was the most aberrantly hypertyrosyl phosphorylated protein in the hearts of NS mice (Eminaga et al., J Biol Chem 283, 15328-15338 (2008). PZR is a Shp2 switch in fetal/adult myosin contractile genes, was also restored to wild type levels in dasatinib-treated Ptpn11$^{Y279C/+}$ mice (FIG. 25f). Together, these data demonstrate the effectiveness of low dose dasatinib treatment in correcting Noonan syndrome with multiple lentigines (NSML)-related cardiomyopathy at the molecular level.

This is the first evidence for the involvement of c-Src signaling in the pathogenesis of NS. Other groups have reported that Shp2 lies upstream of the SFKs in a phosphatase-dependent manner (Zhang et al., *Mol Cell* 13, 341-355 (2004)). Here a distinct mechanism that invokes the "open" conformation of NS-Shp2 mutants providing enhanced PTP-Shp2/Src-SH3 binding and localization to promote c-Src signaling is demonstrated. Post-development administration of dasatinib at sub-therapeutic doses required for the treatment of CML was sufficient to restore cardiac contractility and function. These data strongly implicate c-Src as a central mediator of NS-mediated pathogenesis. At the low doses of dasatinib, the Src pathway appeared to be selectively affected, whilst ERK1/2 signaling, at least in the myocardium, was negligibly inhibited. However, it is conceivable that ERK1/2 exists in a sub-set of specific cells in the heart that are affected by dasatinib treatment.

Importantly, analysis of calcium-mediated contraction coupling of cardiomyocytes isolated from dasatinib-treated NS mice clearly demonstrated that these cells were a site of action through which dasatinib inhibition of c-Src exerted its effect on the contractile machinery. Consistent with previous observations NS-Shp2 mutants increased $Ca^{2+}$ signaling in the myocardium (Uhlen, et al. *PNAS* 103, 2160-2165 (2006)). Interestingly, myocardium derived from NS mice exhibited reduced contractility, suggesting a reduced sensitivity at the level of $Ca^{2+}$-mediated force contraction which can be explained, at least in part, by the reduced levels of SERCA2A expression.

In summary, a novel and unanticipated therapeutic strategy for the treatment of PTPN11-mediated CHD is described herein. These data identify the Src family of kinases as a class of targets that mediate PTPN11-related CHD. A therapeutic strategy of "low dose" dasatinib, or other c-Src inhibitors, may open up new avenues for the treatment of heart disease.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a cardiovascular disease or condition having aberrant protein tyrosine phosphorylation in a subject, comprising administering a low-dosage of afatinib, axitinib, bosutinib, cabozantinib, cediranib, ceritinib, crizotinib, dabrafenib, dasatinib, erlotinib, everolimus, gefitinib, ibrutinib, imatinib, lapatinib, lenvatinib, lestaurtinib, nilotinib, nintedanib, palbociclib, pazopanib, ponatinib, regorafenib, ruxolitinib, semananib, sirolimus, sorafenib, sunitinib, temsirolimus, tofacitinib, trametinib, vandetanib, or vemurafenib to the subject in need thereof.

2. The method of claim 1, wherein the tyrosine kinase inhibitor decreases aberrant tyrosine phosphorylation of a transmembrane glycoprotein.

3. The method of claim 2, wherein the transmembrane glycoprotein is Protein Zero-Related (PZR).

4. The method of claim 1, wherein the dose of the tyrosine kinase inhibitor is in the range of about 175 fold to about 250 fold lower than a chemotherapeutic dosage of the tyrosine kinase inhibitor.

5. The method of claim 1, wherein the cardiac function is selected from the group consisting of myofibrilar organization, cardiomyocyte contractility, SERCA2A expression, and cardiac fibrosis.

6. The method of claim 1, wherein the tyrosine kinase inhibitor provides an anti-fibrotic effect in cardiac tissue.

7. The method according to claim 1, comprising administering a low dose of trametinib.

8. The method according to claim 1, comprising administering a low dose of dasatinib and a low dose of trametinib to the subject.

* * * * *